United States Patent
Elias et al.

(10) Patent No.: US 11,667,726 B2
(45) Date of Patent: *Jun. 6, 2023

(54) METHODS AND COMPOSITIONS RELATING TO BISPECIFIC ANTI-CHI3L1 ANTIBODY REAGENTS FOR THE TREATMENT OF CANCER

(71) Applicant: BROWN UNIVERSITY, Providence, RI (US)

(72) Inventors: Jack A. Elias, Providence, RI (US); Chun Geun Lee, Woodbridge, CT (US); Chuan Hua He, Madison, CT (US); Bing Ma, Branford, CT (US); Suchitra Kamle, Providence, RI (US); Chang-Min Lee, Warwick, RI (US)

(73) Assignee: Brown University, Providence, RI (US)

( * ) Notice: Subject to any disclaimer, the term of this patent is extended or adjusted under 35 U.S.C. 154(b) by 346 days.

This patent is subject to a terminal disclaimer.

(21) Appl. No.: 16/943,320

(22) Filed: Jul. 30, 2020

(65) Prior Publication Data

US 2021/0009712 A1    Jan. 14, 2021

Related U.S. Application Data

(63) Continuation of application No. 16/124,575, filed on Sep. 7, 2018, now Pat. No. 10,766,968, which is a continuation of application No. PCT/US2018/047633, filed on Aug. 23, 2018.

(60) Provisional application No. 62/650,374, filed on Mar. 30, 2018, provisional application No. 62/549,043, filed on Aug. 23, 2017.

(51) Int. Cl.
| *C07K 16/40* | (2006.01) |
| *A61P 35/04* | (2006.01) |
| *A61K 45/06* | (2006.01) |
| *C07K 16/28* | (2006.01) |
| *A61K 39/00* | (2006.01) |

(52) U.S. Cl.
CPC ............ *C07K 16/40* (2013.01); *A61K 45/06* (2013.01); *A61P 35/04* (2018.01); *C07K 16/2803* (2013.01); *C07K 16/2839* (2013.01); *A61K 2039/505* (2013.01); *A61K 2300/00* (2013.01); *C07K 2317/34* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| 6,808,710 B1 * | 10/2004 | Wood ................ A61P 1/16 424/139.1 |
| 8,673,301 B2 | 3/2014 | Bonnichsen et al. |
| 10,253,111 B2 | 4/2019 | Elias et al. |
| 10,766,968 B2 * | 9/2020 | Elias ................ A61K 45/06 |
| 2002/0058037 A1 | 5/2002 | Noelle et al. |
| 2007/0190599 A1 | 8/2007 | Nakano et al. |
| 2011/0027270 A1 | 2/2011 | Garcia-Sastre et al. |
| 2014/0127225 A1 | 5/2014 | Basi et al. |
| 2017/0037131 A1 | 2/2017 | Bernett et al. |
| 2018/0092989 A1 | 4/2018 | Lyerly et al. |
| 2019/0119405 A1 | 4/2019 | Elias et al. |

FOREIGN PATENT DOCUMENTS

| CN | 105092855 A | 11/2015 |
| WO | 1996/023071 A2 | 8/1996 |
| WO | 1997/040068 A1 | 10/1997 |
| WO | 2007/027748 A2 | 3/2007 |
| WO | 2018/129261 A1 | 7/2018 |

OTHER PUBLICATIONS

Cheon et al., "Suppression of Metastasis Through Inhibition of Chitinase 3-like 1 Expression by Mir-125a-3p-mediated upregulation of USFI", Theranostics, vol. 8, Issue 16, pp. 4409-4428, Aug. 7, 2018.
Faibish et al., "A YKL-40-Neutralizing Antibody Blocks Tumor Angiogenesis and Progression: A Potential Therapeutic Agent in Cancers", Molecular Cancer Therapeutics, vol. 10, Issue 5, pp. 742-751, May 2011.
Kzhyshkowska, et al. "Role of Chitinase-like Proteins in Cancer", Biological Chemistry, vol. 397, Issue 3, pp. 231-247, Mar. 1, 2016. (English Abstract Submitted).
Yanqi, et al. "Synergistic Transcutaneous Immunotherapy Enhances Antitumor Immune Responses through Delivery of Checkpoint Inhibitors" ACS NANO, vol. 10, Issue 9, pp. 8956-8963, Sep. 27, 2016. (English Abstract Submitted).
Extended European Search Report received in European Application No. 18848101.4 dated Apr. 13, 2021, 10 pages.
Ma, et al. "Role of Chitinase 3-Like-1 and Semaphorin 7a in Pulmonary Melanoma Metastasis" Cancer Research, vol. 75, Issue 3, pp. 487-496, Feb. 1, 2015.
Choi et al., "High serum YKL-40 is a poor prognostic marker in patients with advanced non-small cell lung cancer", Acta Oncologica, vol. 49, No. 6, 2010, pp. 861-864.
Chupp et al., "A chitinase-like protein in the lung and circulation of patients with severe asthma", New England Journal of Medicine, vol. 357, No. 20, 2007, pp. 2016-2027.

(Continued)

*Primary Examiner* — Brad Duffy
(74) *Attorney, Agent, or Firm* — Adler Pollock & Sheehan P.C.; Michel Morency

(57) ABSTRACT

It is demonstrated herein that inhibitors of immune checkpoints and CHI3L1 are synergistic. Accordingly, described herein are methods and compositions relating to combinatorial therapies for cancer, e.g., comprising an inhibitor of CHI3L1; and an inhibitor of an immune checkpoint protein. In some embodiments, the CHI3L1 inhibitor can be an antibody or antibody reagent as described herein.

16 Claims, 10 Drawing Sheets

Specification includes a Sequence Listing.

(56) References Cited

OTHER PUBLICATIONS

Junker et al., "Expression of YKL-40 by peritumoral macrophages in human small cell lung cancer", Lung Cancer, vol. 48, No. 2, 2005, pp. 223-231.

Ma et al., "RIG-like Helicase Regulation of Chitinase 3-like 1 Axis and Pulmonary Metastasis", Scientific Reports, DOI:10 1038/srep26299, May 20, 2016, 63 pages.

Steenbakkers et al., "Localization of MHC class II/human cartilage glycoprotein-39 complexes in synovia of rheumatoid arthritis patients using complex-specific monoclonal antibodies", The Journal of Immunology, vol. 170, No. 11, 2003, pp. 5719-5727.

Thom et al., "Elevated pretreatment serum concentration of YKL-40—An independent prognostic biomarker for poor survival in patients with metastatic non small cell lung cancer", Cancer vol. 116, No. 17, 2010, pp. 4114-4121.

Gussow et al., "Humanization of monoclonal antibodies", Methods in Enzymology, vol. 203, 1991, pp. 99-121.

Mariuzza et al., "The structural basis of antigen-antibody recognition", Annual review of biophysics and biophysical Chemistry, vol. 16, No. 1, 1987, pp. 139-159.

Winkler et al., "Changing the antigen binding specificity by single point mutations of an anti-p24 {HIV-1) antibody", The Journal of Immunology, vol. 165, No. 8, 2000, pp. 4505-4514.

Pitt et al., "Resistance Mechanisms to Immune-Checkpoint Blockade in Cancer: Tumor-Intrinsic and -Extrinsic Factors", Immunity 44, Jun. 21, 2016, pp. 1255-1269.

Tame, Jeremy R.H., "Scoring functions: A view from the bench", Journal of Computer-Aided Molecular Design, vol. 13, 1999, pp. 99-108.

Dixon, J. Scott., "Evaluation of the CASP2 Docking Section", Proteins: Structure, Function, and Genetics, Suppl. 1, 1997, pp. 198-204.

Lensink et al., "Docking and Scoring protein Complexes: CAPRI 3rd Edition", DOI: 10.1002/prot.21804, Oct. 5, 2007, pp. 704-718.

International Search Report and Written Opinion received in PCT application No. PCT/US2018/047633, dated Dec. 13, 2018, 13 pages.

\* cited by examiner

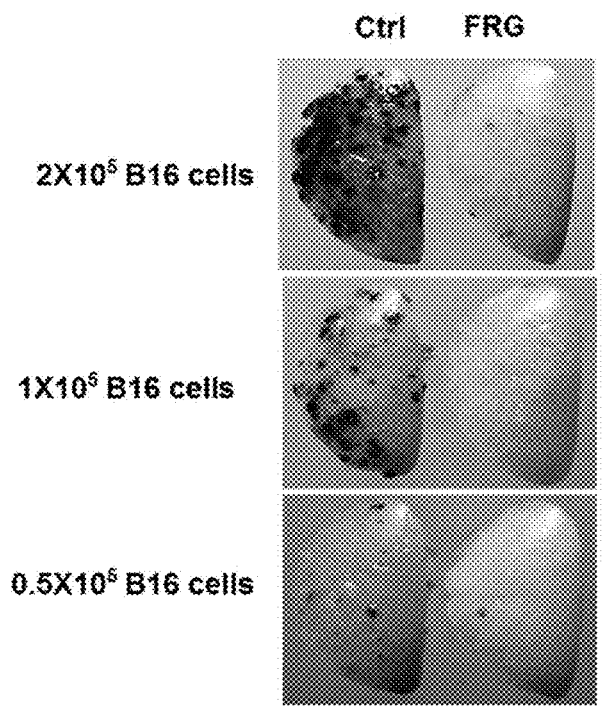
Fig. 4
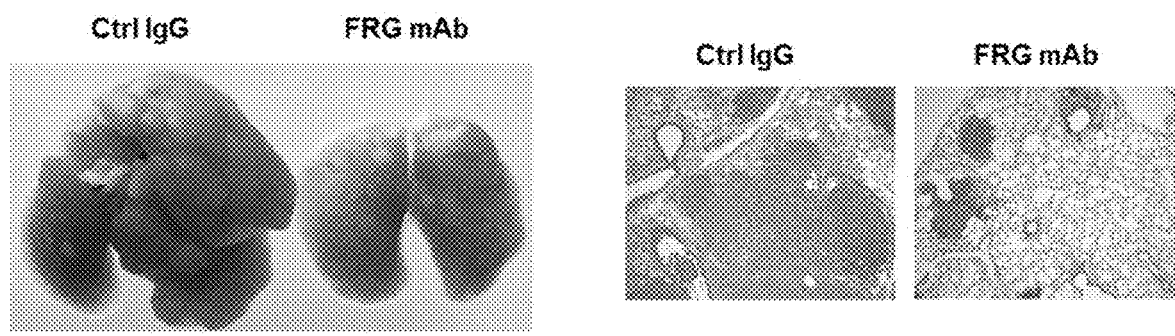
Fig. 5A
Fig. 5B

FRG Light Chain IMGTS-CDRs showing KABAT NUMBERS: BETWEEN AMINO ACID SEQUENCE AND NUCLEOTIDE SEQUENCE

```
<----------------------------------FR1-IMGT---------------------------------><-----
  D   V   V   M   T   Q   T   P   L   S   L   P   V   S   L   G   D   Q   A   S   I   S   C   R   S   S   Q   S   L   V
  L1  L2  L3  L4  L5  L6  L7  L8  L9  L10 L11 L12 L13 L14 L15 L16 L17 L18 L19 L20 L21 L22 L23 L24 L25 L26 L27 L27A L27B L27C
GATGTTGTGATGACCCAAACTCCACTCTCCCTGCCTGTCAGTCTTGGAGATCAAGCCTCCATCTCTTGCAGATCTAGTCAGAGCCTTGTA  406

<------CDR1-IMGT------><-------------------FR2-IMGT--------------------><-CDR2-IM>
  H   S   N   G   N   T   Y   L   H   W   Y   L   Q   K   P   G   Q   S   P   K   L   L   I   Y   K   V   S   N   R   F
 L27D L28 L29 L30 L31 L32 L33 L34 L35 L36 L37 L38 L39 L40 L41 L42 L43 L44 L45 L46 L47 L48 L49 L50 L51 L52 L53 L54 L55
CACAGTAATGGAAACACCTATTTACATTGGTACCTGCAGAAGCCAGGCCAGTCTCCAAAGCTCCTGATCTACAAAGTTTCCAACCGATTT  496

<------------------------------------FR3-IMGT------------------------------------>
  S   G   V   P   D   R   F   S   G   S   G   S   G   T   D   F   T   L   K   I   S   R   V   E   A   E   D   L   G   V
  L56 L57 L58 L59 L60 L61 L62 L63 L64 L65 L66 L67 L68 L69 L70 L71 L72 L73 L74 L75 L76 L77 L78 L79 L80 L81 L82 L83 L84 L85
TCTGGGGTCCCAGACAGGTTCAGTGGCAGTGGATCAGGGACAGATTTCACACTCAAGATCAGCAGAGTGGAGGCTGAGGATCTGGGAGTT  586

<-------CDR3-IMGT-------->
  Y   F   C   S   Q   S   T   H   V   T   W   T   F   G   G   G   T   K   L   E   I   K   R   A
  L86 L87 L88 L89 L90 L91 L92 L93 L94 L95 L96 L97 L98 L99 L100 L101 L102 L103 L104 L105 L106 L107 L108 L109
TATTTCTGCTCTCAAAGTACACATGTTACGTGGACGTTCGGTGGAGGCACCAAGCTGGAAATCAAACGGGCT  658
```

Fig. 7

FRG heavy Chain IMGTS-CDRs showing KABAT NUMBERS: BETWEEN
AMINO ACID SEQUENCE AND NUCLEOTIDE SEQUENCE

Fig. 8

SEQUENCE LISTING

<160> NUMBER OF SEQ ID NOS: 59

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Tyr Thr Phe Thr Asn Tyr Gly
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ile Asn Thr Tyr Thr Gly Glu Pro
1               5

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Arg Leu Gly Tyr Gly Lys Phe Tyr Val Met Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Ser Leu Val His Ser Asn Gly Asn Thr Tyr
1               5                   10

<210> SEQ ID NO 5
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Val Ser
1

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

Ser Gln Ser Thr His Val Thr Trp Thr
1               5

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gggtatacct tcacaaacta tgga                                          24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ataaatacct acactggaga gcca                                          24

<210> SEQ ID NO 9
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gcaagattgg gatatggtaa attctatgtt atggactac                          39

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cagagccttg tacacagtaa tggaaacacc tat                                33

<210> SEQ ID NO 11
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11 aaagtttcc                                                            9

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 12
tctcaaagta cacatgttac gtggacg                                        27

<210> SEQ ID NO 13
<211> LENGTH: 12
<212> TYPE: PRT
<213> ORGANISM: Homo sapiens

<400> SEQUENCE: 13

Phe Arg Gly Gln Glu Asp Ala Ser Pro Asp Arg Phe
1               5                   10

<210> SEQ ID NO 14
<211> LENGTH: 12
<212> TYPE: PRT
<213> ORGANISM: Homo sapiens

<400> SEQUENCE: 14

Arg Gly Ala Thr Val His Arg Ile Leu Gly Gln Gln
1               5                   10

<210> SEQ ID NO 15
<211> LENGTH: 12
<212> TYPE: PRT
<213> ORGANISM: Homo sapiens

<400> SEQUENCE: 15

Ala Ser Ser Glu Thr Gly Val Gly Ala Pro Ile Ser
1               5                   10

<210> SEQ ID NO 16
<211> LENGTH: 12
<212> TYPE: PRT
<213> ORGANISM: Homo sapiens

<400> SEQUENCE: 16

Ile Lys Glu Ala Gln Pro Gly Lys Lys Gln Leu Leu
1               5                   10

<210> SEQ ID NO 17
<211> LENGTH: 12
<212> TYPE: PRT
<213> ORGANISM: Homo sapiens

<400> SEQUENCE: 17

Ser Asn Asp His Ile Asp Thr Trp Glu Trp Asn Asp
1               5                   10

<210> SEQ ID NO 18
<211> LENGTH: 12
<212> TYPE: PRT
<213> ORGANISM: Homo sapiens

<400> SEQUENCE: 18

Tyr Pro Gly Arg Arg Asp Lys Gln His Phe Thr Thr
1               5                   10

<210> SEQ ID NO 19
<211> LENGTH: 12
<212> TYPE: PRT
<213> ORGANISM: Homo sapiens

<400> SEQUENCE: 19

```
Leu Arg Leu Gly Ala Pro Ala Ser Lys Leu Val Met
1               5                   10
```

<210> SEQ ID NO 20
<211> LENGTH: 12
<212> TYPE: PRT
<213> ORGANISM: Homo sapiens

<400> SEQUENCE: 20

```
Pro Gly Ile Pro Gly Arg Phe Thr Lys Glu Ala Gly
1               5                   10
```

<210> SEQ ID NO 21
<211> LENGTH: 12
<212> TYPE: PRT
<213> ORGANISM: Homo sapiens

<400> SEQUENCE: 21

```
Gly Ser Gln Arg Phe Ser Lys Ile Ala Ser Asn Thr
1               5                   10
```

<210> SEQ ID NO 22
<211> LENGTH: 12
<212> TYPE: PRT
<213> ORGANISM: Homo sapiens

<400> SEQUENCE: 22

```
Gly Lys Val Thr Ile Asp Ser Ser Tyr Asp Ile Ala
1               5                   10
```

<210> SEQ ID NO 23
<211> LENGTH: 12
<212> TYPE: PRT
<213> ORGANISM: Homo sapiens

<400> SEQUENCE: 23

```
Gly Met Leu Asn Thr Leu Lys Asn Arg Asn Pro Asn
1               5                   10
```

<210> SEQ ID NO 24
<211> LENGTH: 12
<212> TYPE: PRT
<213> ORGANISM: Homo sapiens

<400> SEQUENCE: 24

```
Ser Asn Thr Gln Ser Arg Arg Thr Phe Ile Lys Ser
1               5                   10
```

<210> SEQ ID NO 25
<211> LENGTH: 383
<212> TYPE: PRT
<213> ORGANISM: Homo sapiens

<400> SEQUENCE: 25

```
Met Gly Val Lys Ala Ser Gln Thr Gly Phe Val Leu Val Leu Leu
1               5                   10                  15

Gln Cys Cys Ser Ala Tyr Lys Leu Val Cys Tyr Tyr Thr Ser Trp Ser
                20                  25                  30

Gln Tyr Arg Glu Gly Asp Gly Ser Cys Phe Pro Asp Ala Leu Asp Arg
            35                  40                  45

Phe Leu Cys Thr His Ile Ile Tyr Ser Phe Ala Asn Ile Ser Asn Asp
        50                  55                  60
```

His Ile Asp Thr Trp Glu Trp Asn Asp Val Thr Leu Tyr Gly Met Leu
 65                  70                  75                  80

Asn Thr Leu Lys Asn Arg Asn Pro Asn Leu Lys Thr Leu Leu Ser Val
                 85                  90                  95

Gly Gly Trp Asn Phe Gly Ser Gln Arg Phe Ser Lys Ile Ala Ser Asn
            100                 105                 110

Thr Gln Ser Arg Arg Thr Phe Ile Lys Ser Val Pro Pro Phe Leu Arg
        115                 120                 125

Thr His Gly Phe Asp Gly Leu Asp Leu Ala Trp Leu Tyr Pro Gly Arg
    130                 135                 140

Arg Asp Lys Gln His Phe Thr Thr Leu Ile Lys Glu Met Lys Ala Glu
145                 150                 155                 160

Phe Ile Lys Glu Ala Gln Pro Gly Lys Lys Gln Leu Leu Leu Ser Ala
                165                 170                 175

Ala Leu Ser Ala Gly Lys Val Thr Ile Asp Ser Ser Tyr Asp Ile Ala
            180                 185                 190

Lys Ile Ser Gln His Leu Asp Phe Ile Ser Ile Met Thr Tyr Asp Phe
        195                 200                 205

His Gly Ala Trp Arg Gly Thr Thr Gly His His Ser Pro Leu Phe Arg
    210                 215                 220

Gly Gln Glu Asp Ala Ser Pro Asp Arg Phe Ser Asn Thr Asp Tyr Ala
225                 230                 235                 240

Val Gly Tyr Met Leu Arg Leu Gly Ala Pro Ala Ser Lys Leu Val Met
                245                 250                 255

Gly Ile Pro Thr Phe Gly Arg Ser Phe Thr Leu Ala Ser Ser Glu Thr
            260                 265                 270

Gly Val Gly Ala Pro Ile Ser Gly Pro Gly Ile Pro Gly Arg Phe Thr
        275                 280                 285

Lys Glu Ala Gly Thr Leu Ala Tyr Tyr Glu Ile Cys Asp Phe Leu Arg
    290                 295                 300

Gly Ala Thr Val His Arg Ile Leu Gly Gln Gln Val Pro Tyr Ala Thr
305                 310                 315                 320

Lys Gly Asn Gln Trp Val Gly Tyr Asp Asp Gln Glu Ser Val Lys Ser
                325                 330                 335

Lys Val Gln Tyr Leu Lys Asp Arg Gln Leu Ala Gly Ala Met Val Trp
            340                 345                 350

Ala Leu Asp Leu Asp Asp Phe Gln Gly Ser Phe Cys Gly Gln Asp Leu
        355                 360                 365

Arg Phe Pro Leu Thr Asn Ala Ile Lys Asp Ala Leu Ala Ala Thr
    370                 375                 380

<210> SEQ ID NO 26
<211> LENGTH: 1867
<212> TYPE: DNA
<213> ORGANISM: Homo sapiens

<400> SEQUENCE: 26
cacatagctc agttcccata aaagggctgg tttgccgcgt cggggagtgg agtgggacag      60
gtatataaag gaagtacagg gcctggggaa gaggccctgt ctaggtagct ggcaccagga     120
gccgtgggca agggaagagg ccacaccctg ccctgctctg ctgcagccag aatgggtgtg     180
aaggcgtctc aaacaggctt tgtggtcctg gtgctgctcc agtgctgctc tgcatacaaa     240
ctggtctgct actacaccag ctggtcccag taccgggaag gcgatgggag ctgcttccca     300
gatgcccttg accgcttcct ctgtacccac atcatctaca gctttgccaa tataagcaac     360

```
gatcacatcg acacctggga gtggaatgat gtgacgctct acggcatgct caacacactc    420
aagaacagga accccaacct gaagactctc ttgtctgtcg gaggatggaa ctttgggtct    480
caaagatttt ccaagatagc ctccaacacc cagagtcgcc ggactttcat caagtcagta    540
ccgccatttc tgcgcaccca tggctttgat gggctggacc ttgcctggct ctaccctgga    600
cggagagaca acagcatttt taccacccta atcaaggaaa tgaaggccga atttataaag    660
gaagcccagc cagggaaaaa gcagctcctg ctcagcgcag cactgtctgc ggggaaggtc    720
accattgaca gcagctatga cattgccaag atatcccaac acctggattt cattagcatc    780
atgacctacg attttcatgg agcctggcgt gggaccacag ccatcacag tcccctgttc     840 cgaggtcagg aggatgcaag tcctgacaga ttcagcaaca ctgactatgc tgtggggtac    900
atgttgagcc tgggggctcc tgccagtaag ctggtgatgg catcccac  cttcggggag    960 agcttcactc tggcttcttc tgagactggt gttggagccc caatctcagg accgggaatt   1020
ccaggccggt tcaccaagga ggcagggacc cttgcctact atgagatctg tgacttcctc   1080
cgcggagcca cagtccatag aatcctcggc cagcaggtcc cctatgccac caagggcaac   1140
cagtgggtag atacgacga ccaggaaagc gtcaaaagca aggtgcagta cctgaaggac    1200
aggcagctgg cgggcgccat ggtatgggcc ctggacctgg atgacttcca gggctccttc   1260
tgcggccagg atctgcgctt ccctctcacc aatgccatca aggatgcact cgctgcaacg   1320
tagccctctg ttctgcacac agcacggggg ccaaggatgc cccgtccccc tctggctcca   1380
gctggccggg agcctgatca cctgccctgc tgagtcccag gctgagcctc agtctccctc   1440
ccttggggcc tatgcagagg tccacaacac acagatttga gctcagccct ggtgggcaga   1500
gaggtaggga tggggctgtg gggatagtga ggcatcgcaa tgtaagactc gggattagta   1560
cacacttgtt gattaatgga aatgtttaca gatccccaag cctggcaagg gaatttcttc   1620
aactccctgc cccccagccc tccttatcaa aggacaccat tttggcaagc tctatcacca   1680
aggagccaaa catcctacaa gacacagtga ccatactaat tatacccct gcaaagccca    1740 gcttgaaacc ttcacttagg aacgtaatcg tgtcccctat cctacttccc cttcctaatt   1800
ccacagctgc tcaataaagt acaagagctt aacagtgaaa aaaaaaaaa aaaaaaaaa     1860 aaaaaaa                                                             1867
```

<210> SEQ ID NO 27
<211> LENGTH: 383
<212> TYPE: PRT
<213> ORGANISM: Homo sapiens

<400> SEQUENCE: 27

```
Met Gly Val Lys Ala Ser Gln Thr Gly Phe Val Val Leu Val Leu Leu
1               5                   10                  15

Gln Cys Cys Ser Ala Tyr Lys Leu Val Cys Tyr Tyr Thr Ser Trp Ser
            20                  25                  30

Gln Tyr Arg Glu Gly Asp Gly Ser Cys Phe Pro Asp Ala Leu Asp Arg
        35                  40                  45

Phe Leu Cys Thr His Ile Ile Tyr Ser Phe Ala Asn Ile Ser Asn Asp
    50                  55                  60

His Ile Asp Thr Trp Glu Trp Asn Asp Val Thr Leu Tyr Gly Met Leu
65                  70                  75                  80

Asn Thr Leu Lys Asn Arg Asn Pro Asn Leu Lys Thr Leu Leu Ser Val
                85                  90                  95
```

Gly Gly Trp Asn Phe Gly Ser Gln Arg Phe Ser Lys Ile Ala Ser Asn
            100                 105                 110

Thr Gln Ser Arg Arg Thr Phe Ile Lys Ser Val Pro Pro Phe Leu Arg
        115                 120                 125

Thr His Gly Phe Asp Gly Leu Asp Leu Ala Trp Leu Tyr Pro Gly Arg
    130                 135                 140

Arg Asp Lys Gln His Phe Thr Thr Leu Ile Lys Glu Met Lys Ala Glu
145                 150                 155                 160

Phe Ile Lys Glu Ala Gln Pro Gly Lys Lys Gln Leu Leu Leu Ser Ala
                165                 170                 175

Ala Leu Ser Ala Gly Lys Val Thr Ile Asp Ser Ser Tyr Asp Ile Ala
            180                 185                 190

Lys Ile Ser Gln His Leu Asp Phe Ile Ser Ile Met Thr Tyr Asp Phe
        195                 200                 205

His Gly Ala Trp Arg Gly Thr Thr Gly His His Ser Pro Leu Phe Arg
    210                 215                 220

Gly Gln Glu Asp Ala Ser Pro Asp Arg Phe Ser Asn Thr Asp Tyr Ala
225                 230                 235                 240

Val Gly Tyr Met Leu Arg Leu Gly Ala Pro Ala Ser Lys Leu Val Met
                245                 250                 255

Gly Ile Pro Thr Phe Gly Arg Ser Phe Thr Leu Ala Ser Ser Glu Thr
            260                 265                 270

Gly Val Gly Ala Pro Ile Ser Gly Pro Gly Ile Pro Gly Arg Phe Thr
        275                 280                 285

Lys Glu Ala Gly Thr Leu Ala Tyr Tyr Glu Ile Cys Asp Phe Leu Arg
    290                 295                 300

Gly Ala Thr Val His Arg Thr Leu Gly Gln Gln Val Pro Tyr Ala Thr
305                 310                 315                 320

Lys Gly Asn Gln Trp Val Gly Tyr Asp Asp Gln Glu Ser Val Lys Ser
                325                 330                 335

Lys Val Gln Tyr Leu Lys Asp Arg Gln Leu Ala Gly Ala Met Val Trp
            340                 345                 350

Ala Leu Asp Leu Asp Asp Phe Gln Gly Ser Phe Cys Gly Gln Asp Leu
        355                 360                 365

Arg Phe Pro Leu Thr Asn Ala Ile Lys Asp Ala Leu Ala Ala Thr
    370                 375                 380

<210> SEQ ID NO 28
<211> LENGTH: 383
<212> TYPE: PRT
<213> ORGANISM: Homo sapiens

<400> SEQUENCE: 28

Met Gly Val Lys Ala Ser Gln Thr Gly Phe Val Val Leu Val Leu Leu
1               5                   10                  15

Gln Cys Cys Ser Ala Tyr Lys Leu Val Cys Tyr Tyr Thr Ser Trp Ser
            20                  25                  30

Gln Tyr Arg Glu Gly Asp Gly Ser Cys Phe Pro Asp Ala Leu Asp Arg
        35                  40                  45

Phe Leu Cys Thr His Ile Ile Tyr Ser Phe Ala Asn Ile Ser Asn Asp
    50                  55                  60

His Ile Asp Thr Trp Glu Trp Asn Asp Val Thr Leu Tyr Gly Met Leu
65                  70                  75                  80

Asn Thr Leu Lys Asn Arg Asn Pro Asn Leu Lys Thr Leu Leu Ser Val
                85                  90                  95

```
Gly Gly Trp Asn Phe Gly Ser Gln Arg Phe Ser Lys Ile Ala Ser Asn
            100                 105                 110

Thr Gln Ser Arg Arg Thr Phe Ile Lys Ser Val Pro Pro Phe Leu Arg
            115                 120                 125

Thr His Gly Phe Asp Gly Leu Asp Leu Ala Trp Leu Tyr Pro Gly Arg
            130                 135                 140

Arg Asp Lys Gln His Phe Thr Thr Leu Ile Lys Glu Met Lys Ala Glu
145                 150                 155                 160

Phe Ile Lys Glu Ala Gln Pro Gly Lys Lys Gln Leu Leu Ser Ala
                165                 170                 175

Ala Leu Ser Ala Gly Lys Val Thr Ile Asp Ser Ser Tyr Asp Ile Ala
            180                 185                 190

Lys Ile Ser Gln His Leu Asp Phe Ile Ser Ile Met Thr Tyr Asp Phe
            195                 200                 205

His Gly Ala Trp Arg Gly Thr Thr Gly His His Ser Pro Leu Phe Arg
            210                 215                 220

Gly Gln Glu Asp Ala Ser Pro Asp Arg Phe Ser Asn Thr Asp Tyr Ala
225                 230                 235                 240

Val Gly Tyr Met Leu Arg Leu Gly Ala Pro Ala Ser Lys Leu Val Met
            245                 250                 255

Gly Ile Pro Thr Phe Gly Arg Ser Phe Thr Leu Ala Ser Ser Glu Thr
            260                 265                 270

Gly Val Gly Ala Pro Ile Ser Gly Pro Gly Ile Pro Gly Arg Phe Thr
            275                 280                 285

Lys Glu Ala Gly Thr Leu Ala Tyr Tyr Glu Ile Cys Asp Phe Leu Arg
            290                 295                 300

Gly Ala Thr Val His Arg Ile Leu Gly Gln Gln Val Pro Tyr Ala Thr
305                 310                 315                 320

Lys Gly Asn Gln Trp Val Gly Tyr Asp Asp Gln Glu Ser Val Lys Ser
            325                 330                 335

Lys Val Gln Tyr Leu Lys Asp Arg Gln Leu Ala Gly Ala Met Val Trp
            340                 345                 350

Ala Leu Asp Leu Asp Asp Phe Gln Gly Ser Phe Cys Gly Gln Asp Leu
            355                 360                 365

Arg Phe Pro Leu Thr Asn Ala Ile Lys Asp Ala Leu Ala Ala Thr
            370                 375                 380

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Gly Gly Gly Ser
1               5

<210> SEQ ID NO 30

<400> SEQUENCE: 30

000

<210> SEQ ID NO 31
```

<400> SEQUENCE: 31

000

<210> SEQ ID NO 32

<400> SEQUENCE: 32

000

<210> SEQ ID NO 33

<400> SEQUENCE: 33

000

<210> SEQ ID NO 34

<400> SEQUENCE: 34

000

<210> SEQ ID NO 35

<400> SEQUENCE: 35

000

<210> SEQ ID NO 36
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Arg Asn Glu Asp Met Ser Thr Tyr Phe Cys
                85                  90                  95

Ala Arg Leu Gly Tyr Gly Lys Phe Tyr Val Met Asp Tyr Trp Gly Gln
            100                 105                 110

Gly Thr Ser Val Thr Val Ser Ser
        115                 120

<210> SEQ ID NO 37
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
cagatccagt tggtgcagtc tggacctgag ctgaagaagc ctggagagac agtcaagatc      60

```
tcctgcaagg cttctgggta taccttcaca aactatggaa tgaactgggt gaagcaggct    120
ccaggaaagg gtttaaagtg gatgggctgg ataaatacct acactggaga gccaacatat    180
gctgatgact tcaagggacg gtttgccttc tctttggaaa cctctgccag cactgcctat    240
ttgcagatca caaccctcag aaatgaggac atgtctacat atttctgtgc aagattggga    300
tatggtaaat tctatgttat ggactactgg ggtcagggaa cgtcagtcac cgtctcctca    360
```

<210> SEQ ID NO 38
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Thr Trp Thr Phe Gly Gly Gly Thr Lys Leu Glu Ile Lys
            100                 105                 110
```

<210> SEQ ID NO 39
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39

```
gatgttgtga tgacccaaac tccactctcc ctgcctgtca gtcttggaga tcaagcctcc    60
atctcttgca gatctagtca gagccttgta cacagtaatg gaaacaccta tttacattgg    120
tacctgcaga agccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tatttctgct ctcaaagtac acatgttacg    300
tggacgttcg gtggaggcac caagctggaa atcaaa                              336
```

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 40

```
His His His His His His
1               5
```

<210> SEQ ID NO 41
<211> LENGTH: 3347
<212> TYPE: DNA
<213> ORGANISM: Homo sapiens

<400> SEQUENCE: 41

| | |
|---|---|
| cagtctcggc tgattgccgc tgtcgctccc ggggccacgg gatgacgcct cctccgcccg | 60 |
| gacgtgccgc cccagcgca ccgcgcgccc gcgtccctgg cccgccggct cggttggggc | 120 |
| ttccgctgcg gctgcggctg ctgctgctgc tctgggcggc cgccgcctcc gcccagggcc | 180 |
| acctaaggag cggaccccgc atcttcgccg tctggaaagg ccatgtaggg caggaccggg | 240 |
| tggactttgg ccagactgag ccgcacacgg tgcttttcca cgagccaggc agctcctctg | 300 |
| tgtgggtggg aggacgtggc aaggtctacc tctttgactt ccccgagggc aagaacgcat | 360 |
| ctgtgcgcac ggactgcgag aactacatca ctctcctgga gaggcggagt gaggggctgc | 420 |
| tggcctgtgg caccaacgcc cggcacccca gctgctggaa cctggtgaat ggcactgtgg | 480 |
| tgccacttgg cgagatgaga ggctacgccc ccttcagccc ggacgagaac tccctggttc | 540 |
| tgtttgaagg ggacgaggtg tattccacca tccggaagca ggaatacaat gggaagatcc | 600 |
| ctcggttccg ccgcatccgg ggcgagagtg agctgtacac cagtgatact gtcatgcaga | 660 |
| acccacagtt catcaaagcc accatcgtgc accaagacca ggcttacgat gacaagatct | 720 |
| actacttctt ccgagaggac aatcctgaca gaatcctga ggctcctctc aatgtgtccc | 780 |
| gtgtggccca gttgtgcagg ggggaccagg gtggggaaag ttcactgtca gtctccaagt | 840 |
| ggaacacttt tctgaaagcc atgctggtat gcagtgatgc tgccaccaac aagaacttca | 900 |
| acaggctgca agacgtcttc ctgctccctg accccagcgg ccagtggagg acaccaggg | 960 |
| tctatggtgt tttctccaac ccctggaact actcagccgt ctgtgtgtat tccctcggtg | 1020 |
| acattgacaa ggtcttccgt acctcctcac tcaagggcta ccactcaagc cttcccaacc | 1080 |
| cgcggcctgg caagtgcctc ccagaccagc agccgatacc cacagagacc ttccaggtgg | 1140 |
| ctgaccgtca cccagaggtg gcgcagaggg tggagcccat ggggcctctg aagacgccat | 1200 |
| tgttccactc taaataccac taccagaaag tggccgtcca ccgcatgcaa gccagccacg | 1260 |
| gggagacctt tcatgtgctt tacctaacta cagacagggg cactatccac aaggtggtgg | 1320 |
| aaccggggga gcaggagcac agcttcgcct tcaacatcat ggagatccag cccttccgcc | 1380 |
| gcgcggctgc catccagacc atgtcgctgg atgctgagcg gaggaagctg tatgtgagct | 1440 |
| cccagtggga ggtgagccag gtgccctgg acctgtgtga ggtctatggc ggggctgcc | 1500 |
| acggttgcct catgtcccga gacccctact gcggctggga ccaaggccgc tgcatctcca | 1560 |
| tctacagctc cgaacggtca gtgctgcaat ccattaatcc agccgagcca cacaaggagt | 1620 |
| gtcccaaccc caaaccagac aaggccccac tgcagaaggt ttccctggcc ccaaactctc | 1680 |
| gctactacct gagctgcccc atggaatccc gccacgccac ctactcatgg cgccacaagg | 1740 |
| agaacgtgga gcagagctgc gaacctggtc accagagccc caactgcatc ctgttcatcg | 1800 |
| agaacctcac ggcgcagcag tacgccact acttctgcga gcccaggag ggctcctact | 1860 |
| tccgcgaggc tcagcactgg cagctgctgc ccgaggacgc atcatggcc gagcacctgc | 1920 |
| tgggtcatgc ctgtgccctg gccgcctccc tctggctggg ggtgctgccc acactcactc | 1980 |
| ttggcttgct ggtccactag ggcctcccga ggctgggcat gcctcaggct tctgcagccc | 2040 |
| agggcactag aacgtctcac actcagagcc ggctggcccg ggagctcctt gcctgccact | 2100 |

```
tcttccaggg gacagaataa cccagtggag gatgccaggc ctggagacgt ccagccgcag    2160
gcggctgctg ggccccaggt ggcgcacgga tggtgagggg ctgagaatga gggcaccgac    2220
tgtgaagctg gggcatcgat gacccaagac tttatcttct ggaaaatatt tttcagactc    2280
ctcaaacttg actaaatgca gcgatgctcc cagcccaaga gcccatgggt cggggagtgg    2340
gtttggatag gagagctggg actccatctc gaccctgggg ctgaggcctg agtccttctg    2400
gactcttggt acccacattg cctccttccc ctccctctct catggctggg tggctggtgt    2460
tcctgaagac ccagggctac cctctgtcca gccctgtcct ctgcagctcc ctctctggtc    2520
ctgggtccca caggacagcc gccttgcatg tttattgaag gatgtttgct ttccggacgg    2580
aaggacggaa aaagctctat ttttatgtta ggcttatttc atgtatagct acttccgact    2640
gcatctgtat gaaaatacca aaactacatg cgggggggtg ggtgggaaag ggaggggctg    2700
ggaagggatg ggttggggag cggggggtgat cccagtctga ggctcccggg gatgagataa    2760
gagtctggag acgggcatgg gttcttggag agtggcatga gctggctctg ccctgggagc    2820
ccggtctgag ggggacgttg ttggagcccc tagtgttggg ggtggttatg ggagggggtg    2880
gggtgaggga acgggagaa tgaaggagaa aactgagccc tagtttcacc gtgttcattt    2940
ggaaggacga gccgggtcct caggggggagg ttccaggact ctgcccttgg cgttgagggt    3000 tgggggggcgg ggggcctcct cccttcctct cagcccccctt ccccaggggc tgtgcttcca    3060
tgctcctagc ctcccacctt cgctcaggac atgttataac ttaggctaaa ctgtgaaaat    3120
tccggtgggg atggcctggg ccgagctctc caggcaggcg gccctgcccc cagccctgtc    3180
catccatttc agggggggagc tgggcccttc tccggctgtg tctggccacc cagggcagtg    3240
gctggggcca gtggccttcc agctttggcc cctgcacctc ttctcaatgc actttaataa    3300
tgtaacatat tactaataaa caagctattt atttacctgc aaaaaaa           3347

<210> SEQ ID NO 42
<211> LENGTH: 3285
<212> TYPE: DNA
<213> ORGANISM: Homo sapiens

<400> SEQUENCE: 42
agacgctgcg cggggcgggt gcggagtgtg ctgcacccgg agggagtgcg tgcgcgcagc      60
tctgcgggtc ccgggctgtc cccgcgctgt ccccgcgtgg agcgtgtggg tttgggccat    120
gtagggcagg accgggtgga ctttggccag actgagccgc acacggtgct tttccacgag    180
ccaggcagct cctctgtgtg ggtgggagga cgtggcaagg tctacctctt tgacttcccc    240
gagggcaaga acgcatctgt gcgcacggtg aatatcggct ccacaaaggg gtcctgtctg    300
gataagcggg actgcgagaa ctacatcact ctccctggaga ggcggagtga ggggctgctg    360
gcctgtggca ccaacgcccg gcaccccagc tgctggaacc tggtgaatgg cactgtggtg    420
ccacttggcg agatgagagg ctacgccccc ttcagcccgg acgagaactc cctggttctg    480
tttgaagggg acgaggtgta ttccaccatc cggaagcagg aatacaatgg gaagatccct    540
cggttccgcc gcatccgggg cgagagtgag ctgtacacca gtgatactgt catgcagaac    600
ccacagttca tcaaagccac catcgtgcac caagaccagg cttacgatga caagatctac    660
tacttcttcc gagaggacaa tcctgacaag aatcctgagg ctcctctcaa tgtgtcccgt    720
gtggcccagt gtgcaggggg gaccagggt ggggaaagtt cactgtcagt ctccaagtgg    780
aacacttttc tgaaagccat gctggtatgc agtgatgctg ccaccaacaa gaacttcaac    840
aggctgcaag acgtcttcct gctccctgac cccagcggcc agtggaggga caccagggtc    900
```

-continued

```
tatggtgttt tctccaaccc ctggaactac tcagccgtct gtgtgtattc cctcggtgac   960
attgacaagg tcttccgtac ctcctcactc aagggctacc actcaagcct tcccaacccg  1020
cggcctggca agtgcctccc agaccagcag ccgatacccc agagaccttc caggtggct   1080 gaccgtcacc cagaggtggc gcagagggtg agcccatgg ggcctctgaa gacgccattg   1140
ttccactcta ataccacta ccagaaagtg gccgtccacc gcatgcaagc cagccacggg   1200
gagacctttc atgtgcttta cctaactaca gacaggggca ctatccacaa ggtggtggaa   1260
ccgggggagc aggagcacag cttcgccttc aacatcatgg agatccagcc cttccgccgc   1320
gcggctgcca tccagaccat gtcgctggat gctgagcgga ggaagctgta tgtgagctcc   1380
cagtgggagg tgagccaggt gcccctggac ctgtgtgagg tctatggcgg gggctgccac   1440
ggttgcctca tgtcccgaga cccctactgc ggctgggacc aaggccgctg catctccatc   1500
tacagctccg aacggtcagt gctgcaatcc attaatccag ccgagccaca caaggagtgt   1560 cccaaccccca aaccagacaa ggccccactg cagaaggttt ccctggcccc aaactctcgc   1620
tactacctga gctgccccat ggaatcccgc cacgccacct actcatggcg ccacaaggag   1680
aacgtggagc agagctgcga acctggtcac cagagcccca actgcatcct gttcatcgag   1740
aacctcacgg cgcagcagta cggccactac ttctgcgagg cccaggaggg ctcctacttc   1800
cgcgaggctc agcactggca gctgctgccc gaggacggca tcatggccga gcacctgctg   1860
ggtcatgcct gtgccctggc cgcctccctc tggctggggg tgctgcccac actcactctt   1920
ggcttgctgg tccactaggg cctcccgagg ctgggcatgc ctcaggcttc tgcagcccag   1980
ggcactagaa cgtctcacac tcagagccgg ctggcccggg agctccttgc ctgccacttc   2040
ttccagggga cagaataacc cagtggagga tgccaggcct ggagacgtcc agccgcaggc   2100
ggctgctggg ccccaggtgg cgcacggatg gtgaggggct gagaatgagg gcaccgactg   2160
tgaagctggg gcatcgatga cccaagactt tatcttctgg aaaatatttt tcagactcct   2220
caaacttgac taaatgcagc gatgctccca gcccaagagc ccatgggtcg gggagtgggt   2280
ttggatagga gagctgggac tccatctcga ccctggggct gaggcctgag tccttctgga   2340
ctcttggtac ccacattgcc tccttcccct ccctctctca tggctgggtg gctggtgttc   2400
ctgaagaccc agggctaccc tctgtccagc cctgtcctct gcagctccct ctctggtcct   2460
gggtcccaca ggacagccgc cttgcatgtt tattgaagga tgtttgcttt ccggacggaa   2520
ggacggaaaa agctctattt ttatgttagg cttatttcat gtatagctac ttccgactgc   2580
atctgtatga aaataccaaa actacatgcg gggggtggg tgggaaaggg aggggctggg   2640
aagggatggg ttggggagcg ggggtgatcc cagtctgagg ctcccgggga tgagataaga   2700
gtctggagac gggcatgggt tcttggagag tggcatgagc tggctctgcc ctgggagccc   2760
ggtctgaggg ggacgttgtt ggagccccta gtgttggggg tggttatggg aggggtggg   2820 gtgagggaaa cgggagaatg aaggagaaaa ctgagcccta gtttcaccgt gttcatttgg   2880
aaggacgagc cgggtcctca gggggaggtt ccaggactct gcccttggcg ttagggttg    2940 gggggcgggg ggcctcctcc cttcctctca gcccccttcc ccaggggctg tgcttccatg   3000
ctcctagcct cccaccttcg ctcaggacat gttataactt aggctaaact gtgaaaattc   3060
cggtggggat ggcctgggcc gagctctcca ggcaggcggc cctgccccca gccctgtcca   3120
tccatttcag gggggagctg ggcccttctc cggctgtgtc tggccaccca gggcagtggc   3180
tggggccagt ggccttccag ctttggcccc tgcacctctt ctcaatgcac tttaataatg   3240
```
taacatatta ctaataaaca agctatttat ttacctgcaa aaaaa        3285

<210> SEQ ID NO 43
<211> LENGTH: 3389
<212> TYPE: DNA
<213> ORGANISM: Homo sapiens

<400> SEQUENCE: 43
cagtctcggc tgattgccgc tgtcgctccc ggggccacgg gatgacgcct cctccgcccg    60
gacgtgccgc ccccagcgca ccgcgcgccc gcgtccctgg cccgccggct cggttggggc   120
ttccgctgcg gctgcggctg ctgctgctgc tctgggcggc cgccgcctcc gcccagggcc   180
acctaaggag cggaccccgc atcttcgccg tctggaaagg ccatgtaggg caggaccggg   240
tggactttgg ccagactgag ccgcacacgg tgcttttcca cgagccaggc agctcctctg   300
tgtgggtggg aggacgtggc aaggtctacc tctttgactt ccccgagggc aagaacgcat   360
ctgtgcgcac ggtgaatatc ggctccacaa aggggtcctg tctggataag cgggactgcg   420
agaactacat cactctcctg gagaggcgga gtgaggggct gctggcctgt ggcaccaacg   480
cccggcaccc cagctgctgg aacctggtga atggcactgt ggtgccactt ggcgagatga   540
gaggctacgc ccccttcagc ccggacgaga actccctggt tctgtttgaa ggggacgagg   600
tgtattccac catccggaag caggaataca atgggaagat ccctcggttc cgccgcatcc   660
ggggcgagag tgagctgtac accagtgata ctgtcatgca gaacccacag ttcatcaaag   720
ccaccatcgt gcaccaagac caggcttacg atgacaagat ctactacttc ttccgagagg   780
acaatcctga caagaatcct gaggctcctc tcaatgtgtc ccgtgtggcc cagttgtgca   840
ggggggacca gggtgggaa agttcactgt cagtctccaa gtggaacact tttctgaaag   900
ccatgctggt atgcagtgat gctgccacca acaagaactt caacaggctg caagacgtct   960
tcctgctccc tgaccccagc ggccagtgga gggacaccag ggtctatggt gttttctcca  1020
accccctggaa ctactcagcc gtctgtgtgt attcccgcgg tgacattgac aaggtcttcc  1080
gtacctcctc actcaagggc taccactcaa gccttcccaa cccgcggcct ggcaagtgcc  1140
tcccagacca gcagccgata cccacagaga ccttccaggt ggctgaccgt cacccagagg  1200
tggcgcagag ggtggagccc atggggcctc tgaagacgcc attgttccac tctaaatacc  1260
actaccagaa agtggccgtc caccgcatgc aagccagcca cggggagacc tttcatgtgc  1320
tttacctaac tacagacagg ggcactatcc acaaggtggt ggaaccgggg gagcaggagc  1380
acagcttcgc cttcaacatc atggagatcc agccttccg ccgcgcggct gccatccaga  1440
ccatgtcgct ggatgctgag cggaggaagc tgtatgtgag ctcccagtgg gaggtgagcc  1500
aggtgcccct ggacctgtgt gaggtctatg gcggggctg ccacggttgc ctcatgtccc  1560
gagacccta ctgcggctgg gaccaaggcc gctgcatctc catctacagc tccgaacggt  1620
cagtgctgca atccattaat ccagccgagc acacaaagga gtgtcccaac cccaaaccag  1680
acaaggcccc actgcagaag gtttccctgg ccccaaaactc tcgctactac ctgagctgcc  1740
ccatggaatc ccgccacgcc acctactcat ggcgccacaa ggagaacgtg gagcagagct  1800
gcgaacctgg tcaccagagc cccaactgca tcctgttcat cgagaacctc acggcgcagc  1860
agtacggcca ctacttctgc gaggcccagg agggctccta cttccgcgag gctcagcact  1920
ggcagctgct gcccgaggac ggcatcatgg ccgagcacct gctgggtcat gcctgtgccc  1980
tggccgcctc cctctggctg ggggtgctgc ccacactcac tcttggcttg ctggtccact  2040
agggcctccc gaggctgggc atgcctcagg cttctgcagc ccagggcact agaacgtctc  2100

```
acactcagag ccggctggcc cgggagctcc ttgcctgcca cttcttccag gggacagaat    2160
aacccagtgg aggatgccag gcctggagac gtccagccgc aggcggctgc tgggccccag    2220
gtggcgcacg gatggtgagg ggctgagaat gagggcaccg actgtgaagc tggggcatcg    2280
atgacccaag actttatctt ctggaaaata tttttcagac tcctcaaact tgactaaatg    2340
cagcgatgct cccagcccaa gagcccatgg gtcggggagt gggtttggat aggagagctg    2400
ggactccatc tcgaccctgg ggctgaggcc tgagtccttc tggactcttg gtacccacat    2460
tgcctccttc ccctcccctct ctcatggctg ggtggctggt gttcctgaag acccagggct    2520
accctctgtc cagccctgtc ctctgcagct ccctctctgg tcctgggtcc cacaggacag    2580
ccgccttgca tgtttattga aggatgtttg ctttccggac ggaaggacgg aaaaagctct    2640
atttttatgt taggcttatt tcatgtatag ctacttccga ctgcatctgt atgaaaatac    2700
caaaactaca tgcggggggg tgggtgggaa agggaggggc tgggaaggga tgggttgggg    2760
agcgggggtg atcccagtct gaggctcccg gggatgagat aagagtctgg agacgggcat    2820
gggttcttgg agagtggcat gagctggctc tgccctggga gcccggtctg aggggacgt     2880 tgttggagcc cctagtgttg ggggtggtta tgggaggggg tggggtgagg gaaacgggag    2940
aatgaaggag aaaactgagc cctagtttca ccgtgttcat ttggaaggac gagccgggtc    3000
ctcaggggga ggttccagga ctctgcccctt ggcgttgagg gttgggggc ggggggcctc    3060 ctcccttcct ctcagccccc ttcccaggg gctgtgcttc catgctccta gcctcccacc    3120
ttcgctcagg acatgttata acttaggcta aactgtgaaa attccggtgg ggatggcctg    3180
ggccgagctc tccaggcagg cggccctgcc cccagccctg tccatccatt tcagggggga    3240
gctgggccct tctccggctg tgtctggcca cccagggcag tggctggggc cagtggcctt    3300
ccagctttgg cccctgcacc tcttctcaat gcactttaat aatgtaacat attactaata    3360
aacaagctat ttatttacct gcaaaaaaa                                      3389
```

<210> SEQ ID NO 44
<211> LENGTH: 652
<212> TYPE: PRT
<213> ORGANISM: Homo sapiens

<400> SEQUENCE: 44

```
Met Thr Pro Pro Pro Gly Arg Ala Ala Pro Ser Ala Pro Arg Ala
1               5                   10                  15

Arg Val Pro Gly Pro Pro Ala Arg Leu Gly Leu Pro Leu Arg Leu Arg
            20                  25                  30

Leu Leu Leu Leu Leu Trp Ala Ala Ala Ser Ala Gln Gly His Leu
        35                  40                  45

Arg Ser Gly Pro Arg Ile Phe Ala Val Trp Lys Gly His Val Gly Gln
    50                  55                  60

Asp Arg Val Asp Phe Gly Gln Thr Glu Pro His Thr Val Leu Phe His
65                  70                  75                  80

Glu Pro Gly Ser Ser Ser Val Trp Val Gly Arg Gly Lys Val Tyr
                85                  90                  95

Leu Phe Asp Phe Pro Glu Gly Lys Asn Ala Ser Val Arg Thr Asp Cys
            100                 105                 110

Glu Asn Tyr Ile Thr Leu Leu Glu Arg Arg Ser Glu Gly Leu Leu Ala
        115                 120                 125

Cys Gly Thr Asn Ala Arg His Pro Ser Cys Trp Asn Leu Val Asn Gly
    130                 135                 140
```

```
Thr Val Val Pro Leu Gly Glu Met Arg Gly Tyr Ala Pro Phe Ser Pro
145                 150                 155                 160

Asp Glu Asn Ser Leu Val Leu Phe Glu Gly Asp Glu Val Tyr Ser Thr
                165                 170                 175

Ile Arg Lys Gln Glu Tyr Asn Gly Lys Ile Pro Arg Phe Arg Arg Ile
            180                 185                 190

Arg Gly Glu Ser Glu Leu Tyr Thr Ser Asp Thr Val Met Gln Asn Pro
            195                 200                 205

Gln Phe Ile Lys Ala Thr Ile Val His Gln Asp Gln Ala Tyr Asp Asp
            210                 215                 220

Lys Ile Tyr Tyr Phe Phe Arg Glu Asp Asn Pro Asp Lys Asn Pro Glu
225                 230                 235                 240

Ala Pro Leu Asn Val Ser Arg Val Ala Gln Leu Cys Arg Gly Asp Gln
                245                 250                 255

Gly Gly Glu Ser Ser Leu Ser Val Ser Lys Trp Asn Thr Phe Leu Lys
            260                 265                 270

Ala Met Leu Val Cys Ser Asp Ala Ala Thr Asn Lys Asn Phe Asn Arg
            275                 280                 285

Leu Gln Asp Val Phe Leu Leu Pro Asp Pro Ser Gly Gln Trp Arg Asp
    290                 295                 300

Thr Arg Val Tyr Gly Val Phe Ser Asn Pro Trp Asn Tyr Ser Ala Val
305                 310                 315                 320

Cys Val Tyr Ser Leu Gly Asp Ile Asp Lys Val Phe Arg Thr Ser Ser
                325                 330                 335

Leu Lys Gly Tyr His Ser Ser Leu Pro Asn Pro Arg Pro Gly Lys Cys
            340                 345                 350

Leu Pro Asp Gln Gln Pro Ile Pro Thr Glu Thr Phe Gln Val Ala Asp
            355                 360                 365

Arg His Pro Glu Val Ala Gln Arg Val Glu Pro Met Gly Pro Leu Lys
            370                 375                 380

Thr Pro Leu Phe His Ser Lys Tyr His Tyr Gln Lys Val Ala Val His
385                 390                 395                 400

Arg Met Gln Ala Ser His Gly Glu Thr Phe His Val Leu Tyr Leu Thr
                405                 410                 415

Thr Asp Arg Gly Thr Ile His Lys Val Val Glu Pro Gly Glu Gln Glu
            420                 425                 430

His Ser Phe Ala Phe Asn Ile Met Glu Ile Gln Pro Phe Arg Arg Ala
            435                 440                 445

Ala Ala Ile Gln Thr Met Ser Leu Asp Ala Glu Arg Arg Lys Leu Tyr
            450                 455                 460

Val Ser Ser Gln Trp Glu Val Ser Gln Val Pro Leu Asp Leu Cys Glu
465                 470                 475                 480

Val Tyr Gly Gly Gly Cys His Gly Cys Leu Met Ser Arg Asp Pro Tyr
                485                 490                 495

Cys Gly Trp Asp Gln Gly Arg Cys Ile Ser Ile Tyr Ser Ser Glu Arg
            500                 505                 510

Ser Val Leu Gln Ser Ile Asn Pro Ala Glu Pro His Lys Glu Cys Pro
            515                 520                 525

Asn Pro Lys Pro Asp Lys Ala Pro Leu Gln Lys Val Ser Leu Ala Pro
            530                 535                 540

Asn Ser Arg Tyr Tyr Leu Ser Cys Pro Met Glu Ser Arg His Ala Thr
545                 550                 555                 560
```

-continued

```
Tyr Ser Trp Arg His Lys Glu Asn Val Glu Gln Ser Cys Glu Pro Gly
            565                 570                 575

His Gln Ser Pro Asn Cys Ile Leu Phe Ile Glu Asn Leu Thr Ala Gln
        580                 585                 590

Gln Tyr Gly His Tyr Phe Cys Glu Ala Gln Glu Gly Ser Tyr Phe Arg
        595                 600                 605

Glu Ala Gln His Trp Gln Leu Leu Pro Glu Asp Gly Ile Met Ala Glu
        610                 615                 620

His Leu Leu Gly His Ala Cys Ala Leu Ala Ala Ser Leu Trp Leu Gly
625                 630                 635                 640

Val Leu Pro Thr Leu Thr Leu Gly Leu Leu Val His
            645                 650

<210> SEQ ID NO 45
<211> LENGTH: 501
<212> TYPE: PRT
<213> ORGANISM: Homo sapiens

<400> SEQUENCE: 45

Met Arg Gly Tyr Ala Pro Phe Ser Pro Asp Glu Asn Ser Leu Val Leu
1               5                   10                  15

Phe Glu Gly Asp Glu Val Tyr Ser Thr Ile Arg Lys Gln Glu Tyr Asn
            20                  25                  30

Gly Lys Ile Pro Arg Phe Arg Ile Arg Gly Glu Ser Glu Leu Tyr
        35                  40                  45

Thr Ser Asp Thr Val Met Gln Asn Pro Gln Phe Ile Lys Ala Thr Ile
    50                  55                  60

Val His Gln Asp Gln Ala Tyr Asp Asp Lys Ile Tyr Tyr Phe Phe Arg
65                  70                  75                  80

Glu Asp Asn Pro Asp Lys Asn Pro Glu Ala Pro Leu Asn Val Ser Arg
                85                  90                  95

Val Ala Gln Leu Cys Arg Gly Asp Gln Gly Gly Glu Ser Ser Leu Ser
            100                 105                 110

Val Ser Lys Trp Asn Thr Phe Leu Lys Ala Met Leu Val Cys Ser Asp
        115                 120                 125

Ala Ala Thr Asn Lys Asn Phe Asn Arg Leu Gln Asp Val Phe Leu Leu
    130                 135                 140

Pro Asp Pro Ser Gly Gln Trp Arg Asp Thr Arg Val Tyr Gly Val Phe
145                 150                 155                 160

Ser Asn Pro Trp Asn Tyr Ser Ala Val Cys Val Tyr Ser Leu Gly Asp
                165                 170                 175

Ile Asp Lys Val Phe Arg Thr Ser Ser Leu Lys Gly Tyr His Ser Ser
            180                 185                 190

Leu Pro Asn Pro Arg Pro Gly Lys Cys Leu Pro Asp Gln Gln Pro Ile
        195                 200                 205

Pro Thr Glu Thr Phe Gln Val Ala Asp Arg His Pro Glu Val Ala Gln
    210                 215                 220

Arg Val Glu Pro Met Gly Pro Leu Lys Thr Pro Leu Phe His Ser Lys
225                 230                 235                 240

Tyr His Tyr Gln Lys Val Ala Val His Arg Met Gln Ala Ser His Gly
                245                 250                 255

Glu Thr Phe His Val Leu Tyr Leu Thr Thr Asp Arg Gly Thr Ile His
            260                 265                 270

Lys Val Val Glu Pro Gly Glu Gln Glu His Ser Phe Ala Phe Asn Ile
        275                 280                 285
```

```
Met Glu Ile Gln Pro Phe Arg Arg Ala Ala Ile Gln Thr Met Ser
    290                 295                 300

Leu Asp Ala Glu Arg Arg Lys Leu Tyr Val Ser Ser Gln Trp Glu Val
305                 310                 315                 320

Ser Gln Val Pro Leu Asp Leu Cys Glu Val Tyr Gly Gly Gly Cys His
                325                 330                 335

Gly Cys Leu Met Ser Arg Asp Pro Tyr Cys Gly Trp Asp Gln Gly Arg
                340                 345                 350

Cys Ile Ser Ile Tyr Ser Ser Glu Arg Ser Val Leu Gln Ser Ile Asn
                355                 360                 365

Pro Ala Glu Pro His Lys Glu Cys Pro Asn Pro Lys Pro Asp Lys Ala
    370                 375                 380

Pro Leu Gln Lys Val Ser Leu Ala Pro Asn Ser Arg Tyr Tyr Leu Ser
385                 390                 395                 400

Cys Pro Met Glu Ser Arg His Ala Thr Tyr Ser Trp Arg His Lys Glu
                405                 410                 415

Asn Val Glu Gln Ser Cys Glu Pro Gly His Gln Ser Pro Asn Cys Ile
                420                 425                 430

Leu Phe Ile Glu Asn Leu Thr Ala Gln Tyr Gly His Tyr Phe Cys
                435                 440                 445

Glu Ala Gln Glu Gly Ser Tyr Phe Arg Glu Ala Gln His Trp Gln Leu
    450                 455                 460

Leu Pro Glu Asp Gly Ile Met Ala Glu His Leu Leu Gly His Ala Cys
465                 470                 475                 480

Ala Leu Ala Ala Ser Leu Trp Leu Gly Val Leu Pro Thr Leu Thr Leu
                485                 490                 495

Gly Leu Leu Val His
            500

<210> SEQ ID NO 46
<211> LENGTH: 666
<212> TYPE: PRT
<213> ORGANISM: Homo sapiens

<400> SEQUENCE: 46

Met Thr Pro Pro Pro Gly Arg Ala Ala Pro Ser Ala Pro Arg Ala
1               5                   10                  15

Arg Val Pro Gly Pro Pro Ala Arg Leu Gly Leu Pro Leu Arg Leu Arg
                20                  25                  30

Leu Leu Leu Leu Leu Trp Ala Ala Ala Ser Ala Gln Gly His Leu
            35                  40                  45

Arg Ser Gly Pro Arg Ile Phe Ala Val Trp Lys Gly His Val Gly Gln
    50                  55                  60

Asp Arg Val Asp Phe Gly Gln Thr Glu Pro His Thr Val Leu Phe His
65                  70                  75                  80

Glu Pro Gly Ser Ser Ser Val Trp Val Gly Arg Gly Lys Val Tyr
                85                  90                  95

Leu Phe Asp Phe Pro Glu Gly Lys Asn Ala Ser Val Arg Thr Val Asn
                100                 105                 110

Ile Gly Ser Thr Lys Gly Ser Cys Leu Asp Lys Arg Asp Cys Glu Asn
            115                 120                 125

Tyr Ile Thr Leu Leu Glu Arg Arg Ser Glu Gly Leu Leu Ala Cys Gly
    130                 135                 140

Thr Asn Ala Arg His Pro Ser Cys Trp Asn Leu Val Asn Gly Thr Val
```

```
                145                 150                 155                 160
        Val Pro Leu Gly Glu Met Arg Gly Tyr Ala Pro Phe Ser Pro Asp Glu
                        165                 170                 175

Asn Ser Leu Val Leu Phe Glu Gly Asp Glu Val Tyr Ser Thr Ile Arg
                        180                 185                 190

Lys Gln Glu Tyr Asn Gly Lys Ile Pro Arg Phe Arg Ile Arg Gly
                        195                 200                 205

Glu Ser Glu Leu Tyr Thr Ser Asp Thr Val Met Gln Asn Pro Gln Phe
                        210                 215                 220

Ile Lys Ala Thr Ile Val His Gln Asp Gln Ala Tyr Asp Asp Lys Ile
        225                 230                 235                 240

Tyr Tyr Phe Phe Arg Glu Asp Asn Pro Asp Lys Asn Pro Glu Ala Pro
                        245                 250                 255

Leu Asn Val Ser Arg Val Ala Gln Leu Cys Arg Gly Asp Gln Gly Gly
                        260                 265                 270

Glu Ser Ser Leu Ser Val Ser Lys Trp Asn Thr Phe Leu Lys Ala Met
                        275                 280                 285

Leu Val Cys Ser Asp Ala Ala Thr Asn Lys Asn Phe Asn Arg Leu Gln
                        290                 295                 300

Asp Val Phe Leu Leu Pro Asp Pro Ser Gly Gln Trp Arg Asp Thr Arg
        305                 310                 315                 320

Val Tyr Gly Val Phe Ser Asn Pro Trp Asn Tyr Ser Ala Val Cys Val
                        325                 330                 335

Tyr Ser Leu Gly Asp Ile Asp Lys Val Phe Arg Thr Ser Ser Leu Lys
                        340                 345                 350

Gly Tyr His Ser Ser Leu Pro Asn Pro Arg Pro Gly Lys Cys Leu Pro
                        355                 360                 365

Asp Gln Gln Pro Ile Pro Thr Glu Thr Phe Gln Val Ala Asp Arg His
                        370                 375                 380

Pro Glu Val Ala Gln Arg Val Glu Pro Met Gly Pro Leu Lys Thr Pro
        385                 390                 395                 400

Leu Phe His Ser Lys Tyr His Tyr Gln Lys Val Ala Val His Arg Met
                        405                 410                 415

Gln Ala Ser His Gly Glu Thr Phe His Val Leu Tyr Leu Thr Thr Asp
                        420                 425                 430

Arg Gly Thr Ile His Lys Val Val Glu Pro Gly Glu Gln Glu His Ser
                        435                 440                 445

Phe Ala Phe Asn Ile Met Glu Ile Gln Pro Phe Arg Arg Ala Ala Ala
                        450                 455                 460

Ile Gln Thr Met Ser Leu Asp Ala Glu Arg Arg Lys Leu Tyr Val Ser
        465                 470                 475                 480

Ser Gln Trp Glu Val Ser Gln Val Pro Leu Asp Leu Cys Glu Val Tyr
                        485                 490                 495

Gly Gly Gly Cys His Gly Cys Leu Met Ser Arg Asp Pro Tyr Cys Gly
                        500                 505                 510

Trp Asp Gln Gly Arg Cys Ile Ser Ile Tyr Ser Ser Glu Arg Ser Val
                        515                 520                 525

Leu Gln Ser Ile Asn Pro Ala Glu Pro His Lys Glu Cys Pro Asn Pro
                        530                 535                 540

Lys Pro Asp Lys Ala Pro Leu Gln Lys Val Ser Leu Ala Pro Asn Ser
        545                 550                 555                 560

Arg Tyr Tyr Leu Ser Cys Pro Met Glu Ser Arg His Ala Thr Tyr Ser
                        565                 570                 575
```

```
Trp Arg His Lys Glu Asn Val Glu Gln Ser Cys Glu Pro Gly His Gln
            580                 585                 590

Ser Pro Asn Cys Ile Leu Phe Ile Glu Asn Leu Thr Ala Gln Gln Tyr
        595                 600                 605

Gly His Tyr Phe Cys Glu Ala Gln Glu Gly Ser Tyr Phe Arg Glu Ala
    610                 615                 620

Gln His Trp Gln Leu Leu Pro Glu Asp Gly Ile Met Ala Glu His Leu
625                 630                 635                 640

Leu Gly His Ala Cys Ala Leu Ala Ala Ser Leu Trp Leu Gly Val Leu
                645                 650                 655

Pro Thr Leu Thr Leu Gly Leu Leu Val His
            660                 665

<210> SEQ ID NO 47
<211> LENGTH: 3879
<212> TYPE: DNA
<213> ORGANISM: Homo sapiens

<400> SEQUENCE: 47
```

| | | | | | |
|---|---|---|---|---|---|
| atcagacgcg | cagaggaggc | ggggccgcgg | ctggtttcct | gccgggggc | ggctctgggc | 60 |
| cgccgagtcc | cctcctcccg | cccctgagga | ggaggagccg | ccgccacccg | ccgcgcccga | 120 |
| cacccgggag | gccccgccag | cccgcgggag | aggcccagcg | ggagtcgcgg | aacagcaggc | 180 |
| ccgagcccac | cgcgccgggc | cccggacgcc | gcgcggaaaa | gatgaattta | caaccaattt | 240 |
| tctggattgg | actgatcagt | tcagtttgct | gtgtgtttgc | tcaaacagat | gaaaatagat | 300 |
| gtttaaaagc | aaatgccaaa | tcatgtggag | aatgtataca | agcagggcca | aattgtgggt | 360 |
| ggtgcacaaa | ttcaacattt | ttacaggaag | gaatgcctac | ttctgcacga | tgtgatgatt | 420 |
| tagaagcctt | aaaaaagaag | ggttgccctc | cagatgacat | agaaaatccc | agaggctcca | 480 |
| aagatataaa | gaaaaataaa | aatgtaacca | accgtagcaa | aggaacagca | gagaagctca | 540 |
| agccagagga | tattactcag | atccaaccac | agcagttggt | tttgcgatta | agatcagggg | 600 |
| agccacagac | atttacatta | aaattcaaga | gagctgaaga | ctatcccatt | gacctctact | 660 |
| accttatgga | cctgtcttac | tcaatgaaag | acgatttgga | gaatgtaaaa | agtcttggaa | 720 |
| cagatctgat | gaatgaaatg | aggaggatta | cttcggactt | cagaattgga | tttggctcat | 780 |
| ttgtggaaaa | gactgtgatg | ccttacatta | gcacaacacc | agctaagctc | aggaaccctt | 840 |
| gcacaagtga | acagaactgc | accagcccat | ttagctacaa | aaatgtgctc | agtcttacta | 900 |
| ataaaggaga | agtatttaat | gaacttgttg | gaaaacagcg | catatctgga | aatttggatt | 960 |
| ctccagaagg | tggtttcgat | gccatcatgc | aagttgcagt | ttgtggatca | ctgattggct | 1020 |
| ggaggaatgt | tacacggctg | ctggtgtttt | ccacagatgc | cgggtttcac | tttgctggag | 1080 |
| atgggaaact | tggtggcatt | gttttaccaa | atgatggaca | atgtcacctg | gaaaataata | 1140 |
| tgtacacaat | gagccattat | tatgattatc | cttctattgc | tcaccttgtc | agaaactga | 1200 |
| gtgaaaataa | tattcagaca | atttttgcag | ttactgaaga | atttcagcct | gtttacaagg | 1260 |
| agctgaaaaa | cttgatccct | aagtcagcag | taggaacatt | atctgcaaat | tctagcaatg | 1320 |
| taattcagtt | gatcattgat | gcatacaatt | cccttttcct | agaagtcatt | ttggaaaacg | 1380 |
| gcaaattgtc | agaaggcgta | acaataagtt | acaaatctta | ctgcaagaac | ggggtgaatg | 1440 |
| gaacagggga | aaatggaaga | aaatgttcca | atatttccat | ggagatgag | gttcaatttg | 1500 |
| aaattagcat | aacttcaaat | aagtgtccaa | aaaaggattc | tgacagcttt | aaaattaggc | 1560 |

```
ctctgggctt tacggaggaa gtagaggtta ttcttcagta catctgtgaa tgtgaatgcc    1620
aaagcgaagg catccctgaa agtcccaagt gtcatgaagg aaatgggaca tttgagtgtg    1680
gcgcgtgcag gtgcaatgaa gggcgtgttg gtagacattg tgaatgcagc acagatgaag    1740
ttaacagtga agacatggat gcttactgca ggaaagaaaa cagttcagaa atctgcagta    1800
acaatggaga gtgcgtctgc ggacagtgtg tttgtaggaa gagggataat acaaatgaaa    1860
tttattctgg caaattctgc gagtgtgata atttcaactg tgatagatcc aatggcttaa    1920
tttgtggagg aaatggtgtt tgcaagtgtc gtgtgtgtga gtgcaacccc aactacactg    1980
gcagtgcatg tgactgttct ttggatacta gtacttgtga agccagcaac ggacagatct    2040
gcaatggccg gggcatctgc gagtgtggtg tctgtaagtg tacagatccg aagtttcaag    2100
ggcaaacgtg tgagatgtgt cagacctgcc ttggtgtctg tgctgagcat aaagaatgtg    2160
ttcagtgcag agccttcaat aaaggagaaa agaaagacac atgcacacag gaatgttcct    2220
attttaacat taccaaggta gaaagtcggg acaaattacc ccagccggtc caacctgatc    2280
ctgtgtccca ttgtaaggag aaggatgttg acgactgttg gttctatttt acgtattcag    2340
tgaatgggaa caacgaggtc atggttcatg ttgtggagaa tccagagtgt cccactggtc    2400
cagacatcat tccaattgta gctggtgtgg ttgctgaat tgttcttatt ggccttgcat    2460
tactgctgat atggaagctt ttaatgataa ttcatgacag aagggagttt gctaaatttg    2520
aaaaggagaa aatgaatgcc aaatgggaca cgggtgaaaa tcctatttat aagagtgccg    2580
taacaactgt ggtcaatccg aagtatgagg gaaaatgagt actgcccgtg caaatcccac    2640
aacactgaat gcaaagtagc aatttccata gtcacagtta ggtagcttta gggcaatatt    2700
gccatggttt tactcatgtg caggttttga aaatgtacaa tatgtataat ttttaaaatg    2760
ttttattatt ttgaaaataa tgttgtaatt catgccaggg actgacaaaa gacttgagac    2820
aggatggtta ctcttgtcag ctaaggtcac attgtgcctt tttgaccttt tcttcctgga    2880
ctattgaaat caagcttatt ggattaagtg atatttctat agcgattgaa agggcaatag    2940
ttaaagtaat gagcatgatg agagtttctg ttaatcatgt attaaaactg attttagct    3000 ttacaaatat gtcagtttgc agttatgcag aatccaaagt aaatgtcctg ctagctagtt    3060
aaggattgtt ttaaatctgt tattttgcta tttgcctgtt agacatgact gatgacatat    3120
ctgaaagaca agtatgttga gagttgctgg tgtaaaatac gtttgaaata gttgatctac    3180
aaaggccatg ggaaaaattc agagagttag gaaggaaaaa ccaatagctt taaaacctgt    3240
gtgccatttt aagagttact taatgtttgg taacttttat gccttcactt tacaaattca    3300
agccttagat aaaagaaccg agcaattttc tgctaaaaag tccttgattt agcactattt    3360
acatacaggc catactttac aaagtatttg ctgaatgggg acctttgag ttgaatttat    3420 tttattattt ttattttgtt taatgtctgg tgctttctgt cacctcttct aatctttaa    3480 tgtatttgtt tgcaatttg gggtaagact tttttatga gtacttttc tttgaagttt    3540 tagcggtcaa tttgccttt taatgaacat gtgaagttat actgtggcta tgcaacagct    3600
ctcacctacg cgagtcttac tttgagttag tgccataaca gaccactgta tgtttacttc    3660
tcaccatttg agttgcccat cttgtttcac actagtcaca ttcttgtttt aagtgccttt    3720
agttttaaca gttcactttt tacagtgcta tttactgaag ttatttatta aatatgccta    3780
aaatacttaa atcggatgtc ttgactctga tgtatttat caggttgtgt gcatgaaatt    3840
tttatagatt aaagaagttg aggaaaagca aaaaaaaa                            3879
```

<210> SEQ ID NO 48
<211> LENGTH: 3739
<212> TYPE: DNA
<213> ORGANISM: Homo sapiens

<400> SEQUENCE: 48

| | | | | | |
|---|---|---|---|---|---|
| atgaatttac | aaccaattt | ctggattgga | ctgatcagtt | cagtttgctg | tgtgtttgct | 60 |
| caaacagatg | aaaatagatg | tttaaaagca | aatgccaaat | catgtggaga | atgtatacaa | 120 |
| gcagggccaa | attgtgggtg | gtgcacaaat | tcaacatttt | tacaggaagg | aatgcctact | 180 |
| tctgcacgat | gtgatgattt | agaagcctta | aaaagaagg | gttgccctcc | agatgacata | 240 |
| gaaaatccca | gaggctccaa | agatataaag | aaaaataaaa | atgtaaccaa | ccgtagcaaa | 300 |
| ggaacagcag | agaagctcaa | gccagaggat | attactcaga | tccaaccaca | gcagttggtt | 360 |
| ttgcgattaa | gatcagggga | gccacagaca | tttacattaa | aattcaagag | agctgaagac | 420 |
| tatcccattg | acctctacta | ccttatggac | ctgtcttact | caatgaaaga | cgatttggag | 480 |
| aatgtaaaaa | gtcttggaac | agatctgatg | aatgaaatga | ggaggattac | ttcggacttc | 540 |
| agaattggat | ttggctcatt | tgtggaaaag | actgtgatgc | cttacattag | cacaacacca | 600 |
| gctaagctca | ggaacccttg | cacaagtgaa | cagaactgca | ccagcccatt | tagctacaaa | 660 |
| aatgtgctca | gtcttactaa | taaggagaa | gtatttaatg | aacttgttgg | aaaacagcgc | 720 |
| atatctggaa | atttggattc | tccagaaggt | ggtttcgatg | ccatcatgca | agttgcagtt | 780 |
| tgtggatcac | tgattggctg | aggaatgtt | acacggctgc | tggtgttttc | cacagatgcc | 840 |
| gggtttcact | tgctggaga | tgggaaactt | ggtggcattg | ttttaccaaa | tgatggacaa | 900 |
| tgtcacctgg | aaaataatat | gtacacaatg | agccattatt | atgattatcc | ttctattgct | 960 |
| caccttgtcc | agaaactgag | tgaaaataat | attcagacaa | tttttgcagt | tactgaagaa | 1020 |
| tttcagcctg | tttacaagga | gctgaaaaac | ttgatcccta | gtcagcagt | aggaacatta | 1080 |
| tctgcaaatt | ctagcaatgt | aattcagttg | atcattgatg | catacaattc | cctttcctca | 1140 |
| gaagtcattt | tggaaaacgg | caaattgtca | gaaggcgtaa | caataagtta | caaatcttac | 1200 |
| tgcaagaacg | gggtgaatgg | aacaggggaa | aatggaagaa | aatgttccaa | tatttccatt | 1260 |
| ggagatgagg | ttcaatttga | aattagcata | acttcaaata | agtgtccaaa | aaaggattct | 1320 |
| gacagcttta | aaattaggcc | tctgggcttt | acggaggaag | tagaggttat | tcttcagtac | 1380 |
| atctgtgaat | gtgaatgcca | aagcgaaggc | atccctgaaa | gtcccaagtg | tcatgaagga | 1440 |
| aatgggacat | ttgagtgtgg | cgcgtgcagg | tgcaatgaag | ggcgtgttgg | tagacattgt | 1500 |
| gaatgcagca | cagatgaagt | taacagtgaa | gacatggatg | cttactgcag | gaaagaaaac | 1560 |
| agttcagaaa | tctgcagtaa | caatggagag | tgcgtctgcg | acagtgtgt | ttgtaggaag | 1620 |
| agggataata | caaatgaaat | ttattctggc | aaattctgcg | agtgtgataa | tttcaactgt | 1680 |
| gatagatcca | atggcttaat | ttgtggagga | aatggtgttt | gcaagtgtcg | tgtgtgtgag | 1740 |
| tgcaaccca | actacactgg | cagtgcatgt | gactgttctt | tggatactag | tacttgtgaa | 1800 |
| gccagcaacg | gacagatctg | caatggccgg | ggcatctgcg | agtgtggtgt | ctgtaagtgt | 1860 |
| acagatccga | gtttcaagg | gcaaacgtgt | gagatgtgtc | agacctgcct | tggtgtctgt | 1920 |
| gctgagcata | agaatgtgt | tcagtgcaga | gccttcaata | aggagaaaa | gaaagacaca | 1980 |
| tgcacacagg | aatgttccta | ttttaacatt | accaaggtag | aaagtcggga | caaattaccc | 2040 |
| cagccggtcc | aacctgatcc | tgtgtcccat | tgtaaggaga | aggatgttga | cgactgttgg | 2100 |
| ttctatttta | cgtattcagt | gaatgggaac | aacgaggtca | tggttcatgt | tgtggagaat | 2160 |

```
ccagagtgtc ccactggtcc agacatcatt ccaattgtag ctggtgtggt tgctggaatt      2220
gttcttattg gccttgcatt actgctgata tggaagcttt taatgataat tcatgacaga      2280
agggagtttg ctaaatttga aaggagaaa atgaatgcca aatgggacac gcaagaaaat       2340
ccgatttaca agagtcctat taataatttc aagaatccaa actacggacg taaagctggt      2400
ctctaaattg ccggtgaaaa tcctatttat aagagtgccg taacaactgt ggtcaatccg      2460
aagtatgagg gaaaatgagt actgcccgtg caaatcccac aacactgaat gcaaagtagc      2520
aatttccata gtcacagtta ggtagcttta gggcaatatt gccatggttt tactcatgtg      2580
caggttttga aaatgtacaa tatgtataat ttttaaaatg ttttattatt ttgaaaataa      2640
tgttgtaatt catgccaggg actgacaaaa gacttgagac aggatggtta ctcttgtcag      2700
ctaaggtcac attgtgcctt tttgaccttt tcttcctgga ctattgaaat caagcttatt      2760
ggattaagtg atatttctat agcgattgaa agggcaatag ttaaagtaat gagcatgatg      2820
agagtttctg ttaatcatgt attaaaactg attttttagct ttacaaatat gtcagtttgc      2880
agttatgcag aatccaaagt aaatgtcctg ctagctagtt aaggattgtt ttaaatctgt      2940
tattttgcta tttgcctgtt agacatgact gatgacatat ctgaaagaca agtatgttga      3000
gagttgctgg tgtaaaatac gtttgaaata gttgatctac aaaggccatg ggaaaaattc      3060
agagagttag gaaggaaaaa ccaatagctt taaaacctgt gtgccatttt aagagttact      3120
taatgtttgg taacttttat gccttcactt tacaaattca agccttagat aaaagaaccg      3180
agcaattttc tgctaaaaag tccttgattt agcactattt acatacaggc catactttac      3240
aaagtatttg ctgaatgggg acctttttgag ttgaattat tttattattt ttattttgtt       3300
taatgtctgg tgctttctgt cacctcttct aatctttta tgtatttgtt tgcaattttg        3360
gggtaagact tttttatga gtactttttc tttgaagttt tagcggtcaa tttgccttt         3420 taatgaacat gtgaagttat actgtggcta tgcaacagct ctcacctacg cgagtcttac      3480
tttgagttag tgccataaca gaccactgta tgtttacttc tcaccatttg agttgcccat      3540
cttgtttcac actagtcaca ttcttgtttt aagtgccttt agttttaaca gttcacttttt     3600 tacagtgcta tttactgaag ttatttatta aatatgccta aaatacttaa atcggatgtc      3660
ttgactctga tgtattttat caggttgtgt gcatgaaatt tttatagatt aaagaagttg      3720
aggaaaagca aaaaaaaa                                                     3739
```

<210> SEQ ID NO 49
<211> LENGTH: 3794
<212> TYPE: DNA
<213> ORGANISM: Homo sapiens

<400> SEQUENCE: 49

```
gagccagccc agccgcgttc cgaacgtgag ggtcgccggc ctgggcgctg tcacgtcggg        60
gctgccggag ctgcggggga ccgggcccga acggcccctg acacctgcgg tctcccgccg      120
ggctgggcaa gcgcagatga atttacaacc aattttctgg attggactga tcagttcagt      180
ttgctgtgtg tttgctcaaa cagatgaaaa tagatgttta aaagcaaatg ccaaatcatg      240
tggagaatgt atacaagcag ggccaaattg tgggtggtgc acaaattcaa cattttaca       300 ggaaggaatg cctacttctg cacgatgtga tgatttagaa gccttaaaaa agaagggttg      360
ccctccagat gacatagaaa atcccagagg ctccaaagat ataagaaaa ataaaaatgt       420 aaccaaccgt agcaaaggaa cagcagagaa gctcaagcca gaggatatta ctcagatcca      480
accacagcag ttggttttgc gattaagatc aggggagcca cagacattta cattaaaatt      540
```

```
caagagagct gaagactatc ccattgacct ctactacctt atggacctgt cttactcaat      600
gaaagacgat ttggagaatg taaaaagtct tggaacagat ctgatgaatg aaatgaggag      660
gattacttcg gacttcagaa ttggatttgg ctcatttgtg aaaagactg tgatgcctta       720 cattagcaca acaccagcta agctcaggaa cccttgcaca agtgaacaga actgcaccag      780
cccatttagc tacaaaaatg tgctcagtct tactaataaa ggagaagtat ttaatgaact      840
tgttggaaaa cagcgcatat ctggaaattt ggattctcca gaaggtggtt tcgatgccat      900
catgcaagtt gcagtttgtg gatcactgat tggctggagg aatgttacac ggctgctggt      960
gttttccaca gatgccgggt ttcactttgc tggagatggg aaacttggtg gcattgtttt     1020
accaaatgat ggacaatgtc acctggaaaa taatatgtac acaatgagcc attattatga     1080
ttatccttct attgctcacc ttgtccagaa actgagtgaa aataatattc agacaatttt     1140
tgcagttact gaagaatttc agcctgttta caaggagctg aaaaacttga tccctaagtc     1200
agcagtagga acattatctg caaattctag caatgtaatt cagttgatca ttgatgcata     1260
caattccctt tcctcagaag tcattttgga aaacggcaaa ttgtcagaag gcgtaacaat     1320
aagttacaaa tcttactgca agaacggggt gaatggaaca ggggaaaatg gaagaaaatg     1380
ttccaatatt tccattggag atgaggttca atttgaaatt agcataactt caaataagtg     1440
tccaaaaaag gattctgaca gctttaaaat taggcctctg ggcttacgg aggaagtaga      1500 ggttattctt cagtacatct gtgaatgtga atgccaaagc gaaggcatcc ctgaaagtcc     1560
caagtgtcat gaaggaaatg ggacatttga gtgtggcgcg tgcaggtgca atgaagggcg     1620
tgttggtaga cattgtgaat gcagcacaga tgaagttaac agtgaagaca tggatgctta     1680
ctgcaggaaa gaaacagtt cagaaatctg cagtaacaat ggagagtgcg tctgcggaca      1740
gtgtgtttgt aggaagaggg ataatacaaa tgaaatttat tctggcaaat tctgcgagtg     1800
tgataatttc aactgtgata gatccaatgg cttaatttgt ggaggaaatg gtgtttgcaa     1860
gtgtcgtgtg tgtgagtgca accccaacta cactggcagt gcatgtgact gttctttgga     1920
tactagtact tgtgaagcca gcaacggaca gatctgcaat ggccggggca tctgcgagtg     1980
tggtgtctgt aagtgtacag atccgaagtt tcaagggcaa acgtgtgaga tgtgtcagac     2040
ctgccttggt gtctgtgctg agcataaaga atgtgttcag tgcagagcct tcaataaagg     2100
agaaaagaaa gacacatgca cacaggaatg ttcctatttt aacattacca aggtagaaag     2160
tcgggacaaa ttaccccagc cggtccaacc tgatcctgtg tcccattgta aggagaagga     2220
tgttgacgac tgttggttct atttacgta ttcagtgaat gggaacaacg aggtcatggt      2280
tcatgttgtg gagaatccag agtgtcccac tggtccagac atcattccaa ttgtagctgg     2340
tgtggttgct ggaattgttc ttattggcct tgcattactg ctgatatgga gctttttaat     2400
gataattcat gacagaaggg agtttgctaa atttgaaaag gagaaaatga atgccaaatg     2460
ggacacgggt gaaaatccta tttataagag tgccgtaaca actgtggtca atccgaagta     2520
tgagggaaaa tgagtactgc ccgtgcaaat cccacaacac tgaatgcaaa gtagcaattt     2580
ccatagtcac agttaggtag ctttagggca atattgccat ggttttactc atgtgcaggt     2640
tttgaaaatg tacaatatgt ataatttta aaatgtttta ttattttgaa aataatgttg      2700
taattcatgc cagggactga caaaagactt gagacaggat ggttactctt gtcagctaag     2760
gtcacattgt gccttttga ccttttcttc ctggactatt gaaatcaagc ttattggatt      2820
aagtgatatt tctatagcga ttgaaagggc aatagttaaa gtaatgagca tgatgagagt     2880
```

-continued

```
ttctgttaat catgtattaa aactgatttt tagctttaca aatatgtcag tttgcagtta   2940
tgcagaatcc aaagtaaatg tcctgctagc tagttaagga ttgttttaaa tctgttattt   3000
tgctatttgc ctgttagaca tgactgatga catatctgaa agacaagtat gttgagagtt   3060
gctggtgtaa aatacgtttg aaatagttga tctacaaagg ccatgggaaa aattcagaga   3120
gttaggaagg aaaaaccaat agctttaaaa cctgtgtgcc attttaagag ttacttaatg   3180
tttggtaact tttatgcctt cactttacaa attcaagcct tagataaaag aaccgagcaa   3240
ttttctgcta aaaagtcctt gatttagcac tatttacata caggccatac tttacaaagt   3300
atttgctgaa tggggacctt ttgagttgaa tttattttat tatttttatt ttgtttaatg   3360
tctggtgctt tctgtcacct cttctaatct tttaatgtat ttgtttgcaa ttttggggta   3420
agactttttt tatgagtact ttttctttga agttttagcg gtcaatttgc ctttttaatg   3480
aacatgtgaa gttatactgt ggctatgcaa cagctctcac ctacgcgagt cttactttga   3540
gttagtgcca taacagacca ctgtatgttt acttctcacc atttgagttg cccatcttgt   3600
ttcacactag tcacattctt gttttaagtg cctttagttt taacagttca ctttttacag   3660
tgctatttac tgaagttatt tattaaatat gcctaaaata cttaaatcgg atgtcttgac   3720
tctgatgtat tttatcaggt tgtgtgcatg aaatttttat agattaaaga agttgaggaa   3780
aagcaaaaaa aaaa                                                     3794

<210> SEQ ID NO 50
<211> LENGTH: 798
<212> TYPE: PRT
<213> ORGANISM: Homo sapiens

<400> SEQUENCE: 50

Met Asn Leu Gln Pro Ile Phe Trp Ile Gly Leu Ile Ser Ser Val Cys
1               5                   10                  15

Cys Val Phe Ala Gln Thr Asp Glu Asn Arg Cys Leu Lys Ala Asn Ala
            20                  25                  30

Lys Ser Cys Gly Glu Cys Ile Gln Ala Gly Pro Asn Cys Gly Trp Cys
        35                  40                  45

Thr Asn Ser Thr Phe Leu Gln Glu Gly Met Pro Thr Ser Ala Arg Cys
    50                  55                  60

Asp Asp Leu Glu Ala Leu Lys Lys Lys Gly Cys Pro Pro Asp Asp Ile
65                  70                  75                  80

Glu Asn Pro Arg Gly Ser Lys Asp Ile Lys Lys Asn Lys Asn Val Thr
                85                  90                  95

Asn Arg Ser Lys Gly Thr Ala Glu Lys Leu Lys Pro Glu Asp Ile Thr
            100                 105                 110

Gln Ile Gln Pro Gln Gln Leu Val Leu Arg Leu Arg Ser Gly Glu Pro
        115                 120                 125

Gln Thr Phe Thr Leu Lys Phe Lys Arg Ala Glu Asp Tyr Pro Ile Asp
    130                 135                 140

Leu Tyr Tyr Leu Met Asp Leu Ser Tyr Ser Met Lys Asp Asp Leu Glu
145                 150                 155                 160

Asn Val Lys Ser Leu Gly Thr Asp Leu Met Asn Glu Met Arg Arg Ile
                165                 170                 175

Thr Ser Asp Phe Arg Ile Gly Phe Gly Ser Phe Val Glu Lys Thr Val
            180                 185                 190

Met Pro Tyr Ile Ser Thr Thr Pro Ala Lys Leu Arg Asn Pro Cys Thr
        195                 200                 205
```

-continued

```
Ser Glu Gln Asn Cys Thr Ser Pro Phe Ser Tyr Lys Asn Val Leu Ser
    210                 215                 220

Leu Thr Asn Lys Gly Glu Val Phe Asn Glu Leu Val Gly Lys Gln Arg
225                 230                 235                 240

Ile Ser Gly Asn Leu Asp Ser Pro Gly Gly Phe Asp Ala Ile Met
                245                 250                 255

Gln Val Ala Val Cys Gly Ser Leu Ile Gly Trp Arg Asn Val Thr Arg
                260                 265                 270

Leu Leu Val Phe Ser Thr Asp Ala Gly Phe His Phe Ala Gly Asp Gly
                275                 280                 285

Lys Leu Gly Gly Ile Val Leu Pro Asn Asp Gly Gln Cys His Leu Glu
    290                 295                 300

Asn Asn Met Tyr Thr Met Ser His Tyr Tyr Asp Tyr Pro Ser Ile Ala
305                 310                 315                 320

His Leu Val Gln Lys Leu Ser Glu Asn Asn Ile Gln Thr Ile Phe Ala
                325                 330                 335

Val Thr Glu Glu Phe Gln Pro Val Tyr Lys Glu Leu Lys Asn Leu Ile
                340                 345                 350

Pro Lys Ser Ala Val Gly Thr Leu Ser Ala Asn Ser Ser Asn Val Ile
    355                 360                 365

Gln Leu Ile Ile Asp Ala Tyr Asn Ser Leu Ser Ser Glu Val Ile Leu
    370                 375                 380

Glu Asn Gly Lys Leu Ser Glu Gly Val Thr Ile Ser Tyr Lys Ser Tyr
385                 390                 395                 400

Cys Lys Asn Gly Val Asn Gly Thr Gly Glu Asn Gly Arg Lys Cys Ser
                405                 410                 415

Asn Ile Ser Ile Gly Asp Glu Val Gln Phe Glu Ile Ser Ile Thr Ser
                420                 425                 430

Asn Lys Cys Pro Lys Lys Asp Ser Asp Ser Phe Lys Ile Arg Pro Leu
    435                 440                 445

Gly Phe Thr Glu Glu Val Glu Val Ile Leu Gln Tyr Ile Cys Glu Cys
    450                 455                 460

Glu Cys Gln Ser Glu Gly Ile Pro Glu Ser Pro Lys Cys His Glu Gly
465                 470                 475                 480

Asn Gly Thr Phe Glu Cys Gly Ala Cys Arg Cys Asn Glu Gly Arg Val
                485                 490                 495

Gly Arg His Cys Glu Cys Ser Thr Asp Glu Val Asn Ser Glu Asp Met
                500                 505                 510

Asp Ala Tyr Cys Arg Lys Glu Asn Ser Ser Glu Ile Cys Ser Asn Asn
    515                 520                 525

Gly Glu Cys Val Cys Gly Gln Cys Val Cys Arg Lys Arg Asp Asn Thr
    530                 535                 540

Asn Glu Ile Tyr Ser Gly Lys Phe Cys Glu Cys Asp Asn Phe Asn Cys
545                 550                 555                 560

Asp Arg Ser Asn Gly Leu Ile Cys Gly Gly Asn Gly Val Cys Lys Cys
                565                 570                 575

Arg Val Cys Glu Cys Asn Pro Asn Tyr Thr Gly Ser Ala Cys Asp Cys
                580                 585                 590

Ser Leu Asp Thr Ser Thr Cys Glu Ala Ser Asn Gly Gln Ile Cys Asn
                595                 600                 605

Gly Arg Gly Ile Cys Glu Cys Gly Val Cys Lys Cys Thr Asp Pro Lys
    610                 615                 620

Phe Gln Gly Gln Thr Cys Glu Met Cys Gln Thr Cys Leu Gly Val Cys
```

```
625                 630                 635                 640
Ala Glu His Lys Glu Cys Val Gln Cys Arg Ala Phe Asn Lys Gly Glu
                645                 650                 655

Lys Lys Asp Thr Cys Thr Gln Glu Cys Ser Tyr Phe Asn Ile Thr Lys
                660                 665                 670

Val Glu Ser Arg Asp Lys Leu Pro Gln Pro Val Gln Pro Asp Pro Val
                675                 680                 685

Ser His Cys Lys Glu Lys Asp Val Asp Asp Cys Trp Phe Tyr Phe Thr
                690                 695                 700

Tyr Ser Val Asn Gly Asn Asn Glu Val Met Val His Val Val Glu Asn
705                 710                 715                 720

Pro Glu Cys Pro Thr Gly Pro Asp Ile Ile Pro Ile Val Ala Gly Val
                725                 730                 735

Val Ala Gly Ile Val Leu Ile Gly Leu Ala Leu Leu Leu Ile Trp Lys
                740                 745                 750

Leu Leu Met Ile Ile His Asp Arg Arg Glu Phe Ala Lys Phe Glu Lys
                755                 760                 765

Glu Lys Met Asn Ala Lys Trp Asp Thr Gly Glu Asn Pro Ile Tyr Lys
                770                 775                 780

Ser Ala Val Thr Thr Val Val Asn Pro Lys Tyr Glu Gly Lys
785                 790                 795

<210> SEQ ID NO 51
<211> LENGTH: 801
<212> TYPE: PRT
<213> ORGANISM: Homo sapiens

<400> SEQUENCE: 51

Met Asn Leu Gln Pro Ile Phe Trp Ile Gly Leu Ile Ser Ser Val Cys
1               5                   10                  15

Cys Val Phe Ala Gln Thr Asp Glu Asn Arg Cys Leu Lys Ala Asn Ala
                20                  25                  30

Lys Ser Cys Gly Glu Cys Ile Gln Ala Gly Pro Asn Cys Gly Trp Cys
                35                  40                  45

Thr Asn Ser Thr Phe Leu Gln Glu Gly Met Pro Thr Ser Ala Arg Cys
                50                  55                  60

Asp Asp Leu Glu Ala Leu Lys Lys Lys Gly Cys Pro Pro Asp Asp Ile
65                  70                  75                  80

Glu Asn Pro Arg Gly Ser Lys Asp Ile Lys Lys Asn Lys Asn Val Thr
                85                  90                  95

Asn Arg Ser Lys Gly Thr Ala Glu Lys Leu Lys Pro Glu Asp Ile Thr
                100                 105                 110

Gln Ile Gln Pro Gln Gln Leu Val Leu Arg Leu Arg Ser Gly Glu Pro
                115                 120                 125

Gln Thr Phe Thr Leu Lys Phe Lys Arg Ala Glu Asp Tyr Pro Ile Asp
                130                 135                 140

Leu Tyr Tyr Leu Met Asp Leu Ser Tyr Ser Met Lys Asp Asp Leu Glu
145                 150                 155                 160

Asn Val Lys Ser Leu Gly Thr Asp Leu Met Asn Glu Met Arg Arg Ile
                165                 170                 175

Thr Ser Asp Phe Arg Ile Gly Phe Gly Ser Phe Val Glu Lys Thr Val
                180                 185                 190

Met Pro Tyr Ile Ser Thr Thr Pro Ala Lys Leu Arg Asn Pro Cys Thr
                195                 200                 205
```

```
Ser Glu Gln Asn Cys Thr Ser Pro Phe Ser Tyr Lys Asn Val Leu Ser
    210                 215                 220

Leu Thr Asn Lys Gly Glu Val Phe Asn Glu Leu Val Gly Lys Gln Arg
225                 230                 235                 240

Ile Ser Gly Asn Leu Asp Ser Pro Gly Gly Phe Asp Ala Ile Met
                245                 250                 255

Gln Val Ala Val Cys Gly Ser Leu Ile Gly Trp Arg Asn Val Thr Arg
                260                 265                 270

Leu Leu Val Phe Ser Thr Asp Ala Gly Phe His Phe Ala Gly Asp Gly
            275                 280                 285

Lys Leu Gly Gly Ile Val Leu Pro Asn Asp Gly Gln Cys His Leu Glu
290                 295                 300

Asn Asn Met Tyr Thr Met Ser His Tyr Tyr Asp Tyr Pro Ser Ile Ala
305                 310                 315                 320

His Leu Val Gln Lys Leu Ser Glu Asn Asn Ile Gln Thr Ile Phe Ala
                325                 330                 335

Val Thr Glu Glu Phe Gln Pro Val Tyr Lys Glu Leu Lys Asn Leu Ile
                340                 345                 350

Pro Lys Ser Ala Val Gly Thr Leu Ser Ala Asn Ser Ser Asn Val Ile
                355                 360                 365

Gln Leu Ile Ile Asp Ala Tyr Asn Ser Leu Ser Ser Glu Val Ile Leu
370                 375                 380

Glu Asn Gly Lys Leu Ser Glu Gly Val Thr Ile Ser Tyr Lys Ser Tyr
385                 390                 395                 400

Cys Lys Asn Gly Val Asn Gly Thr Gly Glu Asn Gly Arg Lys Cys Ser
                405                 410                 415

Asn Ile Ser Ile Gly Asp Glu Val Gln Phe Glu Ile Ser Ile Thr Ser
                420                 425                 430

Asn Lys Cys Pro Lys Lys Asp Ser Asp Ser Phe Lys Ile Arg Pro Leu
                435                 440                 445

Gly Phe Thr Glu Glu Val Glu Val Ile Leu Gln Tyr Ile Cys Glu Cys
                450                 455                 460

Glu Cys Gln Ser Glu Gly Ile Pro Glu Ser Pro Lys Cys His Glu Gly
465                 470                 475                 480

Asn Gly Thr Phe Glu Cys Gly Ala Cys Arg Cys Asn Glu Gly Arg Val
                485                 490                 495

Gly Arg His Cys Glu Cys Ser Thr Asp Glu Val Asn Ser Glu Asp Met
                500                 505                 510

Asp Ala Tyr Cys Arg Lys Glu Asn Ser Ser Glu Ile Cys Ser Asn Asn
                515                 520                 525

Gly Glu Cys Val Cys Gly Gln Cys Val Cys Arg Lys Arg Asp Asn Thr
                530                 535                 540

Asn Glu Ile Tyr Ser Gly Lys Phe Cys Glu Cys Asp Asn Phe Asn Cys
545                 550                 555                 560

Asp Arg Ser Asn Gly Leu Ile Cys Gly Gly Asn Gly Val Cys Lys Cys
                565                 570                 575

Arg Val Cys Glu Cys Asn Pro Asn Tyr Thr Gly Ser Ala Cys Asp Cys
                580                 585                 590

Ser Leu Asp Thr Ser Thr Cys Glu Ala Ser Asn Gly Gln Ile Cys Asn
                595                 600                 605

Gly Arg Gly Ile Cys Glu Cys Gly Val Cys Lys Cys Thr Asp Pro Lys
                610                 615                 620

Phe Gln Gly Gln Thr Cys Glu Met Cys Gln Thr Cys Leu Gly Val Cys
```

```
                625                 630                 635                 640
Ala Glu His Lys Glu Cys Val Gln Cys Arg Ala Phe Asn Lys Gly Glu
                    645                 650                 655
Lys Lys Asp Thr Cys Thr Gln Glu Cys Ser Tyr Phe Asn Ile Thr Lys
                    660                 665                 670
Val Glu Ser Arg Asp Lys Leu Pro Gln Pro Val Gln Pro Asp Pro Val
                    675                 680                 685
Ser His Cys Lys Glu Lys Asp Val Asp Cys Trp Phe Tyr Phe Thr
                    690                 695                 700
Tyr Ser Val Asn Gly Asn Asn Glu Val Met Val His Val Val Glu Asn
705                 710                 715                 720
Pro Glu Cys Pro Thr Gly Pro Asp Ile Ile Pro Ile Val Ala Gly Val
                    725                 730                 735
Val Ala Gly Ile Val Leu Ile Gly Leu Ala Leu Leu Leu Ile Trp Lys
                    740                 745                 750
Leu Leu Met Ile Ile His Asp Arg Arg Glu Phe Ala Lys Phe Glu Lys
                    755                 760                 765
Glu Lys Met Asn Ala Lys Trp Asp Thr Gln Glu Asn Pro Ile Tyr Lys
                    770                 775                 780
Ser Pro Ile Asn Asn Phe Lys Asn Pro Asn Tyr Gly Arg Lys Ala Gly
785                 790                 795                 800
Leu

<210> SEQ ID NO 52
<211> LENGTH: 798
<212> TYPE: PRT
<213> ORGANISM: Homo sapiens

<400> SEQUENCE: 52

Met Asn Leu Gln Pro Ile Phe Trp Ile Gly Leu Ile Ser Ser Val Cys
1                   5                   10                  15
Cys Val Phe Ala Gln Thr Asp Glu Asn Arg Cys Leu Lys Ala Asn Ala
                    20                  25                  30
Lys Ser Cys Gly Glu Cys Ile Gln Ala Gly Pro Asn Cys Gly Trp Cys
                    35                  40                  45
Thr Asn Ser Thr Phe Leu Gln Glu Gly Met Pro Thr Ser Ala Arg Cys
                    50                  55                  60
Asp Asp Leu Glu Ala Leu Lys Lys Lys Gly Cys Pro Pro Asp Asp Ile
65                  70                  75                  80
Glu Asn Pro Arg Gly Ser Lys Asp Ile Lys Lys Asn Lys Asn Val Thr
                    85                  90                  95
Asn Arg Ser Lys Gly Thr Ala Glu Lys Leu Lys Pro Glu Asp Ile Thr
                    100                 105                 110
Gln Ile Gln Pro Gln Gln Leu Val Leu Arg Leu Arg Ser Gly Glu Pro
                    115                 120                 125
Gln Thr Phe Thr Leu Lys Phe Lys Arg Ala Glu Asp Tyr Pro Ile Asp
                    130                 135                 140
Leu Tyr Tyr Leu Met Asp Leu Ser Tyr Ser Met Lys Asp Asp Leu Glu
145                 150                 155                 160
Asn Val Lys Ser Leu Gly Thr Asp Leu Met Asn Glu Met Arg Arg Ile
                    165                 170                 175
Thr Ser Asp Phe Arg Ile Gly Phe Gly Ser Phe Val Glu Lys Thr Val
                    180                 185                 190
Met Pro Tyr Ile Ser Thr Thr Pro Ala Lys Leu Arg Asn Pro Cys Thr
```

```
            195                 200                 205
Ser Glu Gln Asn Cys Thr Ser Pro Phe Ser Tyr Lys Asn Val Leu Ser
210                 215                 220

Leu Thr Asn Lys Gly Glu Val Phe Asn Glu Leu Val Gly Lys Gln Arg
225                 230                 235                 240

Ile Ser Gly Asn Leu Asp Ser Pro Glu Gly Phe Asp Ala Ile Met
                245                 250                 255

Gln Val Ala Val Cys Gly Ser Leu Ile Gly Trp Arg Asn Val Thr Arg
                260                 265                 270

Leu Leu Val Phe Ser Thr Asp Ala Gly Phe His Phe Ala Gly Asp Gly
                275                 280                 285

Lys Leu Gly Gly Ile Val Leu Pro Asn Asp Gly Gln Cys His Leu Glu
290                 295                 300

Asn Asn Met Tyr Thr Met Ser His Tyr Tyr Asp Tyr Pro Ser Ile Ala
305                 310                 315                 320

His Leu Val Gln Lys Leu Ser Glu Asn Asn Ile Gln Thr Ile Phe Ala
                325                 330                 335

Val Thr Glu Glu Phe Gln Pro Val Tyr Lys Glu Leu Lys Asn Leu Ile
                340                 345                 350

Pro Lys Ser Ala Val Gly Thr Leu Ser Ala Asn Ser Ser Asn Val Ile
                355                 360                 365

Gln Leu Ile Ile Asp Ala Tyr Asn Ser Leu Ser Ser Glu Val Ile Leu
370                 375                 380

Glu Asn Gly Lys Leu Ser Glu Gly Val Thr Ile Ser Tyr Lys Ser Tyr
385                 390                 395                 400

Cys Lys Asn Gly Val Asn Gly Thr Gly Glu Asn Gly Arg Lys Cys Ser
                405                 410                 415

Asn Ile Ser Ile Gly Asp Glu Val Gln Phe Glu Ile Ser Ile Thr Ser
                420                 425                 430

Asn Lys Cys Pro Lys Lys Asp Ser Asp Ser Phe Lys Ile Arg Pro Leu
                435                 440                 445

Gly Phe Thr Glu Glu Val Glu Val Ile Leu Gln Tyr Ile Cys Glu Cys
450                 455                 460

Glu Cys Gln Ser Glu Gly Ile Pro Glu Ser Pro Lys Cys His Glu Gly
465                 470                 475                 480

Asn Gly Thr Phe Glu Cys Gly Ala Cys Arg Cys Asn Glu Gly Arg Val
                485                 490                 495

Gly Arg His Cys Glu Cys Ser Thr Asp Glu Val Asn Ser Glu Asp Met
                500                 505                 510

Asp Ala Tyr Cys Arg Lys Glu Asn Ser Ser Glu Ile Cys Ser Asn Asn
                515                 520                 525

Gly Glu Cys Val Cys Gly Gln Cys Val Cys Arg Lys Arg Asp Asn Thr
                530                 535                 540

Asn Glu Ile Tyr Ser Gly Lys Phe Cys Glu Cys Asp Asn Phe Asn Cys
545                 550                 555                 560

Asp Arg Ser Asn Gly Leu Ile Cys Gly Gly Asn Gly Val Cys Lys Cys
                565                 570                 575

Arg Val Cys Glu Cys Asn Pro Asn Tyr Thr Gly Ser Ala Cys Asp Cys
                580                 585                 590

Ser Leu Asp Thr Ser Thr Cys Glu Ala Ser Asn Gly Gln Ile Cys Asn
                595                 600                 605

Gly Arg Gly Ile Cys Glu Cys Gly Val Cys Lys Cys Thr Asp Pro Lys
610                 615                 620
```

```
Phe Gln Gly Gln Thr Cys Glu Met Cys Gln Thr Cys Leu Gly Val Cys
625                 630                 635                 640

Ala Glu His Lys Glu Cys Val Gln Cys Arg Ala Phe Asn Lys Gly Glu
            645                 650                 655

Lys Lys Asp Thr Cys Thr Gln Glu Cys Ser Tyr Phe Asn Ile Thr Lys
            660                 665                 670

Val Glu Ser Arg Asp Lys Leu Pro Gln Pro Val Gln Pro Asp Pro Val
        675                 680                 685

Ser His Cys Lys Glu Lys Asp Val Asp Cys Trp Phe Tyr Phe Thr
    690                 695                 700

Tyr Ser Val Asn Gly Asn Asn Glu Val Met His Val Val Glu Asn
705                 710                 715                 720

Pro Glu Cys Pro Thr Gly Pro Asp Ile Ile Pro Ile Val Ala Gly Val
                725                 730                 735

Val Ala Gly Ile Val Leu Ile Gly Leu Ala Leu Leu Leu Ile Trp Lys
            740                 745                 750

Leu Leu Met Ile Ile His Asp Arg Arg Glu Phe Ala Lys Phe Glu Lys
        755                 760                 765

Glu Lys Met Asn Ala Lys Trp Asp Thr Gly Glu Asn Pro Ile Tyr Lys
    770                 775                 780

Ser Ala Val Thr Thr Val Val Asn Pro Lys Tyr Glu Gly Lys
785                 790                 795

<210> SEQ ID NO 53
<211> LENGTH: 7346
<212> TYPE: DNA
<213> ORGANISM: Homo sapiens

<400> SEQUENCE: 53
gcgaggagga aacggtgccg gagcgcgcag ggcttgctgc cgccaccgcc gctgcacagg     60
ctgccggagc gagcctgccg cgcgccgccc tcccgctctc ccttcctggg cgagctgcgg    120
ggatggggcg gccgcgggag cccgagcgcg cgcaggaacc gccgccgccg ccgcccgcgt    180
ctccgttgcc gcgcgcctga ccgccgtcg ccgccgcgcg ccctgcccgg gggcggcccc    240
cccagcccca tggaggtctc ccggaggaag gcgccgccgc gccccccgcg ccccgcagcg    300
ccactgcccc tgctcgccta tctgctggca ctggcggctc ccggccgggg cgcggacgag    360
cccgtgtggc ggtcggagca agccatcgga gccatcgcgg cgagccagga ggacggcgtg    420
tttgtggcga gcggcagctg cctggaccag ctggactaca gcctggagca cagcctctcg    480
cgcctgtacc gggaccaagc gggcaactgc acagagccgg tctcgctggc gccccccgcg    540
cggcccccggc ccgggagcag cttcagcaag ctgctgctgc cctaccgcga ggggcggcc    600
ggcctcgggg gctgctgct caccggctgg accttcgacc ggggcgcctg cgaggtgcgg    660
cccctgggca acctgagccg caactccctg cgcaacggca ccgaggtggt gtcgtgccac    720
cgcagggct cgacggccgg cgtggtgtac gcgcgcgggc ggaacaaccg ctggtacctg    780
gcggtggccg ccacctacgt gctgcctgag ccggagacgg cgagccgctg caaccccgcg    840
gcatccgacc acgacacggc catcgcgctc aaggacacgg aggggcgcag cctggccacg    900
caggagctgg gcgcctcaa gctgtgcgag ggcgcgggca cctgcactt cgtggacgcc    960
tttctctgga acggcagcat ctacttcccc tactacccct acaactacac gagcggcgct   1020
gccaccggct ggcccagcat ggcgcgcatc gcgcagagca ccgaggtgct gttccagggc   1080
caggcatccc tcgactgcgg ccacggccac cccgacggcc gccgctgct cctctcctcc   1140
```

```
agcctagtgg aggccctgga cgtctgggcg ggagtgttca gcgcggccgc tggagagggc    1200
caggagcggc gctcccccac caccacggcg ctctgcctct tcagaatgag tgagatccag    1260
gcgcgcgcca agagggtcag ctgggacttc aagacggccg agagccactg caaagaaggg    1320
gatcaacctg aaagagtcca accaatcgca tcatctacct tgatccattc cgacctgaca    1380
tccgtttatg gcaccgtggt aatgaacagg actgttttat tcttggggac tggagatggc    1440
cagttactta aggttattct tggtgagaat ttgacttcaa attgtccaga ggttatctat    1500
gaaattaaag aagagacacc tgttttctac aaactcgttc ctgatcctgt gaagaatatc    1560
tacatttatc taacagctgg gaagaggtg aggagaattc gtgttgcaaa ctgcaataaa    1620
cataaatcct gttcggagtg tttaacagcc acagaccctc actgcggttg gtgccattcg    1680
ctacaaaggt gcacttttca aggagattgt gtacattcag agaacttaga aaactggctg    1740
gatatttcgt ctggagcaaa aaagtgccct aaaattcaga taattcgaag cagtaaagaa    1800
aagactacag tgactatggt gggaagcttc tctccaagac actcaaagtg catggtgaag    1860
aatgtggact ctagcaggga gctctgccag aataaaagtc agcccaaccg gacctgcacc    1920
tgtagcatcc caaccagagc aacctacaaa gatgtttcag ttgtcaacgt gatgttctcc    1980
ttcggttctt ggaatttatc agacagattc aactttacca actgctcatc attaaaagaa    2040
tgcccagcat gcgtagaaac tggctgcgcg tggtgtaaaa gtgcaagaag gtgtatccac    2100
cccttcacag cttgcgaccc ttctgattat gagagaaacc aggaacagtg tccagtggct    2160
gtcgagaaga catcaggagg aggaagaccc aaggagaaca aggggaacag aaccaaccag    2220
gctttacagg tcttctacat taagtccatt gagccacaga agtatcgac attagggaaa    2280 agcaacgtga tagtaacggg agcaaacttt acccgggcat cgaacatcac aatgatcctg    2340
aaaggaacca gtacctgtga taaggatgtg atacaggtta gccatgtgct aaatgacacc    2400
cacatgaaat tctctcttcc atcaagccgg aaagaaatga aggatgtgtg tatccagttt    2460
gatggtggga actgctcttc tgtgggatcc ttatcctaca ttgctctgcc acattgttcc    2520
cttatatttc ctgctaccac ctggatcagt ggtggtcaaa atataaccat gatgggcaga    2580
aattttgatg taattgacaa cttaatcatt tcacatgaat taaaaggaaa cataaatgtc    2640
tctgaatatt gtgtggcgac ttactgcggg ttttttagccc ccagtttaaa gagttcaaaa    2700
gtgcgcacga atgtcactgt gaagctgaga gtacaagaca cctacttgga ttgtggaacc    2760
ctgcagtatc gggaggaccc cagattcacg gggtatcggg tggaatccga ggtggacaca    2820
gaactggaag tgaaaattca aaagaaaat gacaacttca acatttccaa aaagacatt    2880 gaaattactc tcttccatgg ggaaaatggg caattaaatt gcagttttga aaatattact    2940
agaaatcaag atcttaccac catcctttgc aaaattaaag gcatcaagac tgcaagcacc    3000
attgccaact cttctaagaa agttcgggtc aagctgggaa acctggagct ctacgtcgag    3060
caggagtcag ttccttccac atggtatttt ctgattgtgc tccctgtctt gctagtgatt    3120
gtcatttttg cggccgtggg ggtgaccagg cacaaatcga aggagctgag tcgcaaacag    3180
agtcaacaac tagaattgct ggaaagcgag ctccggaaag agatacgtga cggctttgct    3240
gagctgcaga tggataaatt ggatgtggtt gatagttttg gaactgttcc cttccttgac    3300
tacaaacatt ttgctctgag aactttcttc cctgagtcag gtggcttcac ccacatcttc    3360
actgaagata tgcataacag agacgccaac gacaagaatg aaagtctcac agctttggat    3420
gccctaatct gtaataaaag ctttcttgtt actgtcatcc acaccttga aaagcagaag    3480
```

```
aacttttctg tgaaggacag gtgtctgttt gcctccttcc taaccattgc actgcaaacc    3540
aagctggtct acctgaccag catcctagag gtgctgacca gggacttgat ggaacagtgt    3600
agtaacatgc agccgaaact catgctgaga cgcacggagt ccgtcgtcga aaaactcctc    3660
acaaactgga tgtccgtctg cctttctgga tttctccggg agactgtcgg agagcccttc    3720
tatttgctgg tgacgactct gaaccagaaa attaacaagg gtcccgtgga tgtaatcact    3780
tgcaaagccc tgtacacact taatgaagac tggctgttgt ggcaggttcc ggaattcagt    3840
actgtggcat taaacgtcgt ctttgaaaaa atcccggaaa acgagagtgc agatgtctgt    3900
cggaatattt cagtcaatgt tctcgactgt gacaccattg gccaagccaa agaaaagatt    3960
ttccaagcat tcttaagcaa aaatggctct ccttatggac ttcagcttaa tgaaattggt    4020
cttgagcttc aaatgggcac acgacagaaa gaacttctgg acatcgacag ttcctccgtg    4080
attcttgaag atggaatcac caagctaaac accattggcc actatgagat atcaaatgga    4140
tccactataa aagtctttaa gaagatagca aattttactt cagatgtgga gtactcggat    4200
gaccactgcc atttgatttt accagattcg gaagcattcc aagatgtgca aggaaagaga    4260
catcgaggga agcacaagtt caaagtaaaa gaaatgtatc tgacaaagct gctgtcgacc    4320
aaggtggcaa ttcattctgt gcttgaaaaa ctttttagaa gcatttggag tttacccaac    4380
agcagagctc catttgctat aaaatacttt tttgactttt tggacgccca ggctgaaaac    4440
aaaaaaatca cagatcctga cgtcgtacat atttggaaaa caaacagcct tcctcttcgc    4500
ttctgggtaa acatcctgaa gaaccctcag tttgtctttg acattaagaa gacaccacat    4560
atagacggct gtttgtcagt gattgcccag gcattcatgg atgcattttc tctcacagag    4620
cagcaactag ggaaggaagc accaactaat aagcttctct atgccaagga tatcccaacc    4680
tacaaagaag agtaaaatc ttattacaaa gcaatcaggg atttgcctcc attgtcatcc    4740
tcagaaatgg aagaattttt aactcaggaa tctaagaaac atgaaaatga atttaatgaa    4800
gaagtggcct tgacagaaat ttacaaatac atcgtaaaat attttgatga gattctaaat    4860
aaactagaaa gagaacgagg gctggaagaa gctcagaaac aactcttgca tgtaaaagtc    4920
ttatttgatg aaaagaagaa atgcaagtgg atgtaagcac tctggggcct ggcttaatct    4980
ggcaaagttc ttcagacgac ttgggagcaa aatggctgct tgagctactc tgtgtcgtta    5040
atttgttgtt tgcacatagg ttccactttg ggcactgtct ttttaagaga ccaaggcaca    5100
tgcacagctt ttagaaagca taccaaccct tgtgcctgtg tgtataccgt gggaacccct    5160
ctgtaaatag agttgaagtg gttgttcaa acagcctcct tgtttacaga gaatacaagg    5220
ccagtaagcg aatgtcagta ttgtaactac agtctccact taagcacaat gatataagtg    5280
gttttgtttg aaaactacag ctatgtagca cttgtgctac actgcacctc tgcattgtaa    5340
agggatactg ccagtgctca aaacaaaatg tgaaatgagt catttggaaa caaggtgggg    5400
gtgttagggc aacctcgagg atttgcagca ttgaaacttt ccccagtagt tcttggaaaa    5460
gctgaccgca gaatttggta gtgtacactt agcattgtg agtgtgtgtg tgtgtttaaa    5520
ccaaaaacta acagtgttgc aacattgttg aaagggctcg tgttttcag tggtcatcaa    5580 ctgcactcca tcaaactcac ctccatttca ccaaggagct ctaaagtaag gagagtgggc    5640
tttatttaaa tgaacagcat tttaaccaga tactttgtcc taatgtatgt tccttttctt    5700
catctgtttt ttcatactaa atgtatttga tagtggacat gttggatatt atacaaaaaa    5760
atcattaatt catttctgtt ccaaaacctt tgatcagaac gatctgtgga agagtaactc    5820
catttctata tgagtgagtg tctccttgct ttagatttct ggtgaaccct gtggttatga    5880
```

```
atacttgtgt gtgatttaaa aaaaaaaaga tacattttac atttcatcga attgctgttc    5940
acactggagt attatatata aatatatata tttgaggccc aaggcctgaa aaatattagt    6000
atacaacttg gtatcttagt cttactatgt acttttttgaa agtattcctc gcaggagaaa   6060
gaatttaaaa tacccatttt attcatgcct ttcttttttaa agaattctct atccagttat   6120
actgtagtct ttttagtgct gattttttaa ttcctgaatt tttgctgctc atgaccagtt    6180
ttaataccac tgtgttttcc ttctattaaa ccagaagaag taaacagcat aattggcaac    6240
tcttgagctt ttcttgtggc aggcacctttt taccccttggt gctccaaatc ccccatctag    6300
gaaagaaaat tttttcaagt caaataacat tgatcacata ttccttgaaa tcatttacca    6360
acactgtatg gagcattagg atttaaatat gaatttgtct taaaggcaat tccttttttgc    6420 ttctgtatta tctggaaaag catgagagag gtgacacctc aacaaactga tcagagaaaa    6480
taagcagtta ctaccctgat aggcaccttc ccaatcctgt tgcttttgac cattgtctgt    6540
ccaacggaca cacctcaaac aaacaaaact accaaataga tgacagatca gaataaaggt    6600
gagaggtctg gtccccattg aaggctgcta cagtcttcaa agaggtgaag gagttcataa    6660
gagaacaaca gtaggaaagt tgagagccaa gggtaggaga gttgcccaaa agacttcccc    6720
tactacttta gggtactgaa aactcaaagg atcagctaca gctttatcta agtatttact    6780
aaatgctaca tgagggtgtc cctgtccagc tttctggcac atgagtcctg tgtggagagt    6840
tacctcctct tccagggact gtgctgttgg gaactttggg caagtcactt acctctttgt    6900 gcctcaatt ctgtataata tttctaagct acctcactga ggtggtatga agattcacta     6960
atgtatgtag cgtgtttgtc aatcctccag tgaaaagcac tatctagatc acattttgga    7020
tcacattagc caaatgcagt aaatggccaa attagatgtg tgctgaagac aatcagtcac    7080
tgggtctata ttaaacagca accagagcaa caaatggcaa acaatttcta ttttcaagtt    7140
tctttgcata tttttttggt gcaaaaccat ttataaactt tttttttctaa cactagtgtc    7200 tacagcagca ttcaaaaaaa ttctgttacc ttttctgtat taggatttaa agtctatttc    7260
ttattgtata cctgattgaa gctgttcttg gagatgaatg ttttaaatgt ctatatccaa    7320
aaaataaaca ttttgatgta actgtg                                        7346
```

<210> SEQ ID NO 54
<211> LENGTH: 1568
<212> TYPE: PRT
<213> ORGANISM: Homo sapiens

<400> SEQUENCE: 54

Met Glu Val Ser Arg Arg Lys Ala Pro Pro Arg Pro Pro Arg Pro Ala
1               5                   10                  15

Ala Pro Leu Pro Leu Leu Ala Tyr Leu Leu Ala Leu Ala Ala Pro Gly
                20                  25                  30

Arg Gly Ala Asp Glu Pro Val Trp Arg Ser Glu Gln Ala Ile Gly Ala
            35                  40                  45

Ile Ala Ala Ser Gln Glu Asp Gly Val Phe Val Ala Ser Gly Ser Cys
        50                  55                  60

Leu Asp Gln Leu Asp Tyr Ser Leu Glu His Ser Leu Ser Arg Leu Tyr
65                  70                  75                  80

Arg Asp Gln Ala Gly Asn Cys Thr Glu Pro Val Ser Leu Ala Pro Pro
                85                  90                  95

Ala Arg Pro Arg Pro Gly Ser Ser Phe Ser Lys Leu Leu Leu Pro Tyr
                100                 105                 110

-continued

```
Arg Glu Gly Ala Ala Gly Leu Gly Gly Leu Leu Thr Gly Trp Thr
        115                 120                 125
Phe Asp Arg Gly Ala Cys Glu Val Arg Pro Leu Gly Asn Leu Ser Arg
    130                 135                 140
Asn Ser Leu Arg Asn Gly Thr Glu Val Val Ser Cys His Pro Gln Gly
145                 150                 155                 160
Ser Thr Ala Gly Val Val Tyr Arg Ala Gly Arg Asn Asn Arg Trp Tyr
                165                 170                 175
Leu Ala Val Ala Ala Thr Tyr Val Leu Pro Glu Pro Glu Thr Ala Ser
            180                 185                 190
Arg Cys Asn Pro Ala Ala Ser Asp His Asp Thr Ala Ile Ala Leu Lys
        195                 200                 205
Asp Thr Glu Gly Arg Ser Leu Ala Thr Gln Glu Leu Gly Arg Leu Lys
    210                 215                 220
Leu Cys Glu Gly Ala Gly Ser Leu His Phe Val Asp Ala Phe Leu Trp
225                 230                 235                 240
Asn Gly Ser Ile Tyr Phe Pro Tyr Tyr Pro Tyr Asn Tyr Thr Ser Gly
                245                 250                 255
Ala Ala Thr Gly Trp Pro Ser Met Ala Arg Ile Ala Gln Ser Thr Glu
            260                 265                 270
Val Leu Phe Gln Gly Gln Ala Ser Leu Asp Cys Gly His Gly His Pro
        275                 280                 285
Asp Gly Arg Arg Leu Leu Leu Ser Ser Ser Leu Val Glu Ala Leu Asp
    290                 295                 300
Val Trp Ala Gly Val Phe Ser Ala Ala Ala Gly Glu Gly Gln Glu Arg
305                 310                 315                 320
Arg Ser Pro Thr Thr Thr Ala Leu Cys Leu Phe Arg Met Ser Glu Ile
                325                 330                 335
Gln Ala Arg Ala Lys Arg Val Ser Trp Asp Phe Lys Thr Ala Glu Ser
            340                 345                 350
His Cys Lys Glu Gly Asp Gln Pro Glu Arg Val Gln Pro Ile Ala Ser
        355                 360                 365
Ser Thr Leu Ile His Ser Asp Leu Thr Ser Val Tyr Gly Thr Val Val
    370                 375                 380
Met Asn Arg Thr Val Leu Phe Leu Gly Thr Gly Asp Gly Gln Leu Leu
385                 390                 395                 400
Lys Val Ile Leu Gly Glu Asn Leu Thr Ser Asn Cys Pro Glu Val Ile
                405                 410                 415
Tyr Glu Ile Lys Glu Glu Thr Pro Val Phe Tyr Lys Leu Val Pro Asp
            420                 425                 430
Pro Val Lys Asn Ile Tyr Ile Tyr Leu Thr Ala Gly Lys Glu Val Arg
        435                 440                 445
Arg Ile Arg Val Ala Asn Cys Asn Lys His Lys Ser Cys Ser Glu Cys
    450                 455                 460
Leu Thr Ala Thr Asp Pro His Cys Gly Trp Cys His Ser Leu Gln Arg
465                 470                 475                 480
Cys Thr Phe Gln Gly Asp Cys Val His Ser Glu Asn Leu Glu Asn Trp
                485                 490                 495
Leu Asp Ile Ser Ser Gly Ala Lys Lys Cys Pro Lys Ile Gln Ile Ile
            500                 505                 510
Arg Ser Ser Lys Glu Lys Thr Thr Val Thr Met Val Gly Ser Phe Ser
        515                 520                 525
```

```
Pro Arg His Ser Lys Cys Met Val Lys Asn Val Asp Ser Ser Arg Glu
    530                 535                 540

Leu Cys Gln Asn Lys Ser Gln Pro Asn Arg Thr Cys Thr Cys Ser Ile
545                 550                 555                 560

Pro Thr Arg Ala Thr Tyr Lys Asp Val Ser Val Val Asn Val Met Phe
                565                 570                 575

Ser Phe Gly Ser Trp Asn Leu Ser Asp Arg Phe Asn Phe Thr Asn Cys
            580                 585                 590

Ser Ser Leu Lys Glu Cys Pro Ala Cys Val Thr Gly Cys Ala Trp
        595                 600                 605

Cys Lys Ser Ala Arg Arg Cys Ile His Pro Phe Thr Ala Cys Asp Pro
    610                 615                 620

Ser Asp Tyr Glu Arg Asn Gln Glu Gln Cys Pro Val Ala Val Glu Lys
625                 630                 635                 640

Thr Ser Gly Gly Gly Arg Pro Lys Glu Asn Lys Gly Asn Arg Thr Asn
                645                 650                 655

Gln Ala Leu Gln Val Phe Tyr Ile Lys Ser Ile Glu Pro Gln Lys Val
                660                 665                 670

Ser Thr Leu Gly Lys Ser Asn Val Ile Val Thr Gly Ala Asn Phe Thr
        675                 680                 685

Arg Ala Ser Asn Ile Thr Met Ile Leu Lys Gly Thr Ser Thr Cys Asp
690                 695                 700

Lys Asp Val Ile Gln Val Ser His Val Leu Asn Asp Thr His Met Lys
705                 710                 715                 720

Phe Ser Leu Pro Ser Ser Arg Lys Glu Met Lys Asp Val Cys Ile Gln
                725                 730                 735

Phe Asp Gly Gly Asn Cys Ser Ser Val Gly Ser Leu Ser Tyr Ile Ala
            740                 745                 750

Leu Pro His Cys Ser Leu Ile Phe Pro Ala Thr Thr Trp Ile Ser Gly
        755                 760                 765

Gly Gln Asn Ile Thr Met Met Gly Arg Asn Phe Asp Val Ile Asp Asn
770                 775                 780

Leu Ile Ile Ser His Glu Leu Lys Gly Asn Ile Asn Val Ser Glu Tyr
785                 790                 795                 800

Cys Val Ala Thr Tyr Cys Gly Phe Leu Ala Pro Ser Leu Lys Ser Ser
                805                 810                 815

Lys Val Arg Thr Asn Val Thr Val Lys Leu Arg Val Gln Asp Thr Tyr
            820                 825                 830

Leu Asp Cys Gly Thr Leu Gln Tyr Arg Glu Asp Pro Arg Phe Thr Gly
        835                 840                 845

Tyr Arg Val Glu Ser Glu Val Asp Thr Glu Leu Glu Val Lys Ile Gln
850                 855                 860

Lys Glu Asn Asp Asn Phe Asn Ile Ser Lys Lys Asp Ile Glu Ile Thr
865                 870                 875                 880

Leu Phe His Gly Glu Asn Gly Gln Leu Asn Cys Ser Phe Glu Asn Ile
                885                 890                 895

Thr Arg Asn Gln Asp Leu Thr Thr Ile Leu Cys Lys Ile Lys Gly Ile
            900                 905                 910

Lys Thr Ala Ser Thr Ile Ala Asn Ser Ser Lys Lys Val Arg Val Lys
        915                 920                 925

Leu Gly Asn Leu Glu Leu Tyr Val Glu Gln Glu Ser Val Pro Ser Thr
930                 935                 940

Trp Tyr Phe Leu Ile Val Leu Pro Val Leu Leu Val Ile Val Ile Phe
```

```
             945                 950                 955                 960
Ala Ala Val Gly Val Thr Arg His Lys Ser Lys Glu Leu Ser Arg Lys
                    965                 970                 975
Gln Ser Gln Gln Leu Glu Leu Leu Glu Ser Glu Leu Arg Lys Glu Ile
                    980                 985                 990
Arg Asp Gly Phe Ala Glu Leu Gln Met Asp Lys Leu Asp Val Val Asp
            995                 1000                1005
Ser Phe Gly Thr Val Pro Phe Leu Asp Tyr Lys His Phe Ala Leu
    1010                1015                1020
Arg Thr Phe Phe Pro Glu Ser Gly Gly Phe Thr His Ile Phe Thr
    1025                1030                1035
Glu Asp Met His Asn Arg Asp Ala Asn Asp Lys Asn Glu Ser Leu
    1040                1045                1050
Thr Ala Leu Asp Ala Leu Ile Cys Asn Lys Ser Phe Leu Val Thr
    1055                1060                1065
Val Ile His Thr Leu Glu Lys Gln Lys Asn Phe Ser Val Lys Asp
    1070                1075                1080
Arg Cys Leu Phe Ala Ser Phe Leu Thr Ile Ala Leu Gln Thr Lys
    1085                1090                1095
Leu Val Tyr Leu Thr Ser Ile Leu Glu Val Leu Thr Arg Asp Leu
    1100                1105                1110
Met Glu Gln Cys Ser Asn Met Gln Pro Lys Leu Met Leu Arg Arg
    1115                1120                1125
Thr Glu Ser Val Val Glu Lys Leu Leu Thr Asn Trp Met Ser Val
    1130                1135                1140
Cys Leu Ser Gly Phe Leu Arg Glu Thr Val Gly Glu Pro Phe Tyr
    1145                1150                1155
Leu Leu Val Thr Thr Leu Asn Gln Lys Ile Asn Lys Gly Pro Val
    1160                1165                1170
Asp Val Ile Thr Cys Lys Ala Leu Tyr Thr Leu Asn Glu Asp Trp
    1175                1180                1185
Leu Leu Trp Gln Val Pro Glu Phe Ser Thr Val Ala Leu Asn Val
    1190                1195                1200
Val Phe Glu Lys Ile Pro Glu Asn Glu Ser Ala Asp Val Cys Arg
    1205                1210                1215
Asn Ile Ser Val Asn Val Leu Asp Cys Asp Thr Ile Gly Gln Ala
    1220                1225                1230
Lys Glu Lys Ile Phe Gln Ala Phe Leu Ser Lys Asn Gly Ser Pro
    1235                1240                1245
Tyr Gly Leu Gln Leu Asn Glu Ile Gly Leu Glu Leu Gln Met Gly
    1250                1255                1260
Thr Arg Gln Lys Glu Leu Leu Asp Ile Asp Ser Ser Ser Val Ile
    1265                1270                1275
Leu Glu Asp Gly Ile Thr Lys Leu Asn Thr Ile Gly His Tyr Glu
    1280                1285                1290
Ile Ser Asn Gly Ser Thr Ile Lys Val Phe Lys Lys Ile Ala Asn
    1295                1300                1305
Phe Thr Ser Asp Val Glu Tyr Ser Asp Asp His Cys His Leu Ile
    1310                1315                1320
Leu Pro Asp Ser Glu Ala Phe Gln Asp Val Gln Gly Lys Arg His
    1325                1330                1335
Arg Gly Lys His Lys Phe Lys Val Lys Glu Met Tyr Leu Thr Lys
    1340                1345                1350
```

```
Leu Leu Ser Thr Lys Val Ala Ile His Ser Val Leu Glu Lys Leu
            1355                1360                1365

Phe Arg Ser Ile Trp Ser Leu Pro Asn Ser Arg Ala Pro Phe Ala
    1370                1375                1380

Ile Lys Tyr Phe Phe Asp Phe Leu Asp Ala Gln Ala Glu Asn Lys
1385                1390                1395

Lys Ile Thr Asp Pro Asp Val Val His Ile Trp Lys Thr Asn Ser
1400                1405                1410

Leu Pro Leu Arg Phe Trp Val Asn Ile Leu Lys Asn Pro Gln Phe
    1415                1420                1425

Val Phe Asp Ile Lys Lys Thr Pro His Ile Asp Gly Cys Leu Ser
    1430                1435                1440

Val Ile Ala Gln Ala Phe Met Asp Ala Phe Ser Leu Thr Glu Gln
    1445                1450                1455

Gln Leu Gly Lys Glu Ala Pro Thr Asn Lys Leu Leu Tyr Ala Lys
1460                1465                1470

Asp Ile Pro Thr Tyr Lys Glu Glu Val Lys Ser Tyr Tyr Lys Ala
    1475                1480                1485

Ile Arg Asp Leu Pro Pro Leu Ser Ser Ser Glu Met Glu Glu Phe
    1490                1495                1500

Leu Thr Gln Glu Ser Lys Lys His Glu Asn Glu Phe Asn Glu Glu
    1505                1510                1515

Val Ala Leu Thr Glu Ile Tyr Lys Tyr Ile Val Lys Tyr Phe Asp
    1520                1525                1530

Glu Ile Leu Asn Lys Leu Glu Arg Glu Arg Gly Leu Glu Glu Ala
    1535                1540                1545

Gln Lys Gln Leu Leu His Val Lys Val Leu Phe Asp Glu Lys Lys
    1550                1555                1560

Lys Cys Lys Trp Met
1565

<210> SEQ ID NO 55
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Thr Trp Thr Phe Gly Gly Gly Thr Lys Leu Glu Ile Lys
            100                 105                 110

Arg Ala
```

<210> SEQ ID NO 56
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
gatgttgtga tgacccaaac tccactctcc ctgcctgtca gtcttggaga tcaagcctcc    60
atctcttgca gatctagtca gagccttgta cacagtaatg aaacaccta tttacattgg    120 tacctgcaga agccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tatttctgct ctcaaagtac acatgttacg    300
tggacgttcg gtggaggcac caagctggaa atcaaacggg ct                      342

<210> SEQ ID NO 57
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Arg Asn Glu Asp Met Ser Thr Tyr Phe Cys
                85                  90                  95

Ala Arg Leu Gly Tyr Gly Lys Phe Tyr Val Met Asp Tyr Trp Gly Gln
            100                 105                 110

Gly Thr Ser Val Thr Val Ser Ser
        115                 120

<210> SEQ ID NO 58
<211> LENGTH: 349
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
cagatccagt tggtgcagtc tggacctgag ctgaagaagc ctggagagac agtcaagatc    60
tcctgcaagg cttctgggta taccttcaca aactatggaa tgaactgggt gaagcaggct    120
ccaggaaagg gtttaaagtg gatgggctgg ataaatacct acactggaga gccaacatat    180
gctgatgact caaggggacg gtttgccttc tctttggaaa cctctgccag cactgcctat    240
ttgcagatca acaacctcag aaatgaggac atgtctacat atttctgtgc aagattggga    300

-continued

| | |
|---|---|
| tatggtaaat tctatgttat ggactactgg ggtcagggaa cgtcagtca | 349 |

<210> SEQ ID NO 59
<211> LENGTH: 1925
<212> TYPE: DNA
<213> ORGANISM: Homo sapiens

<400> SEQUENCE: 59

| | |
|---|---|
| agtggagtgg gacaggtata taaaggaagt acagggcctg ggaagaggc cctgtctagg | 60 |
| tagctggcac caggagccgt gggcaaggga agaggccaca ccctgccctg ctctgctgca | 120 |
| gccagaatgg gtgtgaaggc gtctcaaaca ggctttgtgg tcctggtgct gctccagtgc | 180 |
| tgctctgcat acaaactggt ctgctactac accagctggt cccagtaccg ggaaggcgat | 240 |
| gggagctgct tcccagatgc ccttgaccgc ttcctctgta cccacatcat ctacagcttt | 300 |
| gccaatataa gcaacgatca catcgacacc tgggagtgga atgatgtgac gctctacggc | 360 |
| atgctcaaca cactcaagaa caggaacccc aacctgaaga ctctcttgtc tgtcggagga | 420 |
| tggaactttg gtctcaaag attttccaag atagcctcca cacccagag tcgccggact | 480 |
| ttcatcaagt cagtaccgcc attcctgcgc acccatggct ttgatgggct ggaccttgcc | 540 |
| tggctctacc ctggacggag agacaaacag cattttacca ccctaatcaa ggaaatgaag | 600 |
| gccgaattta taaaggaagc ccagccaggg aaaaagcagc tcctgctcag cgcagcactg | 660 |
| tctgcgggga aggtcaccat tgacagcagc tatgacattg ccaagatatc ccaacacctg | 720 |
| gatttcatta gcatcatgac ctacgatttt catggagcct ggcgtgggac cacaggccat | 780 |
| cacagtcccc tgttccgagg tcaggaggat gcaagtcctg acagattcag caacactgac | 840 |
| tatgctgtgg ggtacatgtt gaggctgggg gctcctgcca gtaagctggt gatgggcatc | 900 |
| cccaccttcg ggaggagctt cactctggct tcttctgaga ctggtgttgg agccccaatc | 960 |
| tcaggaccgg gaattccagg ccggttcacc aaggaggcag ggaccccttgc ctactatgag | 1020 |
| atctgtgact tcctccgcgg agccacagtc catagaaccc tcggccagca ggtcccctat | 1080 |
| gccaccaagg gcaaccagtg ggtaggatac gacgaccagg aaagcgtcaa aagcaaggtg | 1140 |
| cagtacctga aggataggca gctggcaggc gccatggtat gggcctgga cctggatgac | 1200 |
| ttccagggct ccttctgcgg ccaggatctg cgcttccctc tcaccaatgc catcaaggat | 1260 |
| gcactcgctg caacgtagcc ctctgttctg cacacagcac gggggccaag gatgccccgt | 1320 |
| cccctctgg ctccagctgg ccgggagcct gatcacctgc cctgctgagt cccaggctga | 1380 |
| gcctcagtct ccctccttg gggcctatgc agaggtccac aacacacaga tttgagctca | 1440 |
| gccctggtgg gcagagaggt agggatgggg ctgtggggat agtgaggcat cgcaatgtaa | 1500 |
| gactcgggat tagtacacac ttgttgatga ttaatgaaa tgtttacaga tccccaagcc | 1560 |
| tggcaaggga atttcttcaa ctccctgccc cctagccctc cttatcaaag gacaccattt | 1620 |
| tggcaagctc tatcaccaag gagccaaaca tcctacaaga cacagtgacc atactaatta | 1680 |
| tacccctgc aaagccagct tgaaaccttc acttaggaac gtaatcgtgt ccctatcct | 1740 |
| acttcccctt cctaattcca cagctgctca ataaagtaca agagtttaac agtgtgttgg | 1800 |
| cgctttgctt tggtctatct ttgagcgccc actagaccca ctggactcac ctcccccatc | 1860 |
| tcttctgggt tccttcctct gagccttggg acccctgagc ttgcagagat gaaggccgcc | 1920 |
| atgtt | 1925 |

METHODS AND COMPOSITIONS RELATING TO BISPECIFIC ANTI-CHI3L1 ANTIBODY REAGENTS FOR THE TREATMENT OF CANCER

CROSS-REFERENCE TO RELATED APPLICATIONS

This is a continuation application of U.S. patent application Ser. No. 16/124,575 filed Sep. 7, 2018, which claims benefit under 35 U.S.C. § 365(c) and 35 U.S.C. § 120 of International Application No. PCT/US2018/047633 filed Aug. 23, 2018, which designates the U.S. and which claims benefit under 35 U.S.C. § 119(e) of U.S. Provisional Application Nos. 62/650,374 filed Mar. 30, 2018 and 62/549,043 filed Aug. 23, 2017, the contents of which are incorporated herein by reference in their entireties.

GOVERNMENT SUPPORT

This invention was made with government support under Grant Nos. UH2 HL 123876 and UO1 HL108638 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Aug. 23, 2018, is named 058040-091590WOPT_SL.txt and is 115,924 bytes in size.

TECHNICAL FIELD

The technology described herein relates to treatments for cancer.

BACKGROUND

Lung cancer afflicts over 1.8 million people annually, with 1.6 yearly deaths. It is the leading cause of cancer-related death in men and has a low long-term survival rate. Developing improved treatments for this disease is a major public health concern.

SUMMARY

It is demonstrated herein that inhibiting a) CHI3L1 and/or CHI3L1 signaling and b) at least one immune checkpoint protein provides synergistic effects in the treatment of cancer, e.g., lung cancer. Accordingly, provided herein are methods and compositions related to the treatment of cancer.

In one aspect of any of the embodiments, described herein is a method of treating cancer in a subject in need thereof, the method comprising administering: an inhibitor of CHI3L1; and an inhibitor of an immune checkpoint protein.

In one aspect of any of the embodiments, described herein is a therapeutically effective amount of an inhibitor of CHI3L1 and an inhibitor of an immune checkpoint protein for use in the treatment of cancer. In some embodiments of any of the aspects, the inhibitor of CHI3L1 and the inhibitor of an immune checkpoint protein are present in the same composition. In some embodiments of any of the aspects, the inhibitor of CHI3L1 and the inhibitor of an immune checkpoint protein are present in separate compositions.

In one aspect of any of the embodiments, described herein is a pharmaceutical composition comprising an inhibitor of CHI3L1; and an inhibitor of an immune checkpoint protein.

In one aspect of any of the embodiments, described herein is a kit comprising a pharmaceutical composition comprising an inhibitor of CHI3L1; and a pharmaceutical composition comprising an inhibitor of an immune checkpoint protein.

In some embodiments of any of the aspects, the inhibitor of CHI3L1 is an antibody, antibody reagent, antigen-binding fragment thereof, or CAR that specifically binds to CHI3L1.

In some embodiments of any of the aspects, the antibody, antibody reagent, antigen-binding fragment thereof, or CAR comprises at least one heavy or light chain complementarity determining region (CDR) selected from the group consisting of:

(a) a light chain CDR1 having the amino acid sequence of SEQ ID NO: 4;
(b) a light chain CDR2 having the amino acid sequence of SEQ TD NO: 5;
(c) a light chain CDR3 having the amino acid sequence of SEQ ID NO: 6;
(d) a heavy chain CDR1 having the amino acid sequence of SEQ ID NO: 1;
(e) a heavy chain CDR2 having the amino acid sequence of SEQ ID NO: 2; and
(f) a heavy chain CDR3 having the amino acid sequence of SEQ ID NO: 3; or
a conservative substitution variant of one or more of (a)-(f).

In some embodiments of any of the aspects, the antibody, antibody reagent, antigen-binding portion thereof, or CAR of comprises heavy chain CDRs having the amino acid sequences of SEQ ID NOs: 1-3 or a conservative substitution variant of such amino acid sequence. In some embodiments of any of the aspects, the antibody, antibody reagent, antigen-binding portion thereof or CAR comprises light chain CDRs having the amino acid sequences of SEQ ID NOs: 4-6 or a conservative substitution variant of such amino acid sequence. In some embodiments of any of the aspects, the antibody, antibody reagent, antigen-binding portion thereof or CAR comprises light chain CDRs having the amino acid sequences of SEQ ID NOs: 4-6 and heavy chain CDRs having the amino acid sequences of SEQ ID NOs: 1-3 or a conservative substitution variant of such amino acid sequence.

In some embodiments of any of the aspects, the inhibitor of CHI3L1 is antibody, antibody reagent, antigen-binding portion thereof or CAR that competes for binding to CHI3L1 with an antibody comprising light chain CDRs having the amino acid sequences of SEQ ID NOs: 4-6 and heavy chain CDRs having the amino acid sequences of SEQ ID NOs: 1-3.

In some embodiments of any of the aspects, the inhibitor of CHI3L1 binds a CHI3L1 polypeptide at an epitope selected from SEQ ID NOs: 13-24.

In some embodiments of any of the aspects, the inhibitor of CHI3L1 is an inhibitor of a CHI3L1 receptor. In some embodiments of any of the aspects, the CHI3L1 receptor is IL13Rα2, TMEM219, or CRTH2.

In some embodiments of any of the aspects, the inhibitor is an inhibitory antibody or nucleic acid molecule.

In some embodiments of any of the aspects, the cancer is a primary cancer or a metastatic cancer. In some embodiments of any of the aspects, the cancer is malignant cancer. In some embodiments of any of the aspects, the cancer is selected from the group consisting of: prostate cancer, colon cancer, rectal cancer, ovarian cancer, kidney cancer, breast cancer, glioblastoma, melanoma, malignant melanoma, and lung cancer.

In some embodiments of any of the aspects, the inhibitor of an immune checkpoint protein is an antibody, antibody reagent, antigen-binding fragment thereof, or CAR that specifically binds to at least one immune checkpoint protein. In some embodiments of any of the aspects, the inhibitor of an immune checkpoint protein is a natural ligand thereof. In some embodiments of any of the aspects, the natural ligand comprises PD-L1 or B7. In some embodiments of any of the aspects, the immune checkpoint protein is selected from the group consisting of: PD-1; PD-L1; PD-L2; TIM-3; CTLA4; TIGIT; DD1-α; A2AR; B7-H3; B7-H4; BTLA; IDO; TDO; KIR; and LAGS. In some embodiments of any of the aspects, the inhibitor of an immune checkpoint protein is selected from the group consisting of: MGA271; ipilimumab; pembrolizumab; nivolumab; atezolizumab; galiximab; IMP321; BMS-986016; SMB-663513; PF-05082566; IPH2101; KW-0761; CDX-1127; MEDI-6769; CP-870,893; tremelimumab; pidilizumab; MPDL3280A; MED14736; MSB0010718C; AUNP12; avelumab; and durvalumab.

In some embodiments of any of the aspects, the inhibitor of CHI3L1 and the inhibitor of an immune checkpoint protein are present in the same bivalent antibody reagent. In some embodiments of any of the aspects, the immune checkpoint protein is PD-1 or CTLA4.

In some embodiments of any of the aspects, the subject is a subject determined to have an elevated level of CHI3L1. In some embodiments of any of the aspects, the CHI3L1 is circulating CHI3L1.

BRIEF DESCRIPTION OF THE DRAWINGS

FIG. 1A demonstrates mAb analysis under non-denaturing (Non-Den) and denaturing (DEN) conditions with Coomassie staining, Western blot and Isotyping. FIG. 1B depicts FRG detection of Chi3l1 in non-denaturing and denaturing conditions. FIG. 1C depicts Sensitivity and specifcity of FRG against recombinant (r) human and mouse Chi3l1 detected by Western blot. FIG. 1D depicts FRG affinity and dose response curve evaluated by ELISA.

FIG. 2A depicts effects on ERK and AkKT phosphorylation in peritoneal macrophages*. FIG. 2B depicts the effects of different doses of FRG on ERK and AKT phosphorylation in on peritoneal macrophages *. * Thp1 cells, U937 cells, and AMJ2-C11 (mouse alveolar macrophages cell line) showed similar pattern of inhibition and dose responses on Chi3l1-stimulated Erk and Akt activation.

FIG. 4 depicts the effects of FRG on melanoma metastasis. Mice received the noted doses of B16-F10 cells by tail vein injection and were treated with control IGg2b antibody or FRG (200 µg/per mouse) every other day. The mice were sacrificed after 14 days and pulmonary metastasis (sark dots) were evaluated.

FIGS. 5A-5B demonstrate the effects of FRG on primary lung cancer. FIG. 5A depicts the tunor accumulation in representative lungs from mice with both activating $KRAS^{G12D}$ mutations and null p53 mutations which were treated with control (Ctrl) IgG or FRG mAb. FIG. 5B depicts a representative histology of the lungs illustrated in FIG. 5A.

FIG. 7 depicts the light chain CDR sequences of the FRG antibody described herein (SEQ ID NOS 55 and 56, respectively, in order of appearance).

FIG. 8 depicts the heavy chain CDR sequences of the FRG antibody described herein (SEQ ID NOS 57 and 58, respectively, in order of appearance).

DETAILED DESCRIPTION

Figure 1A:
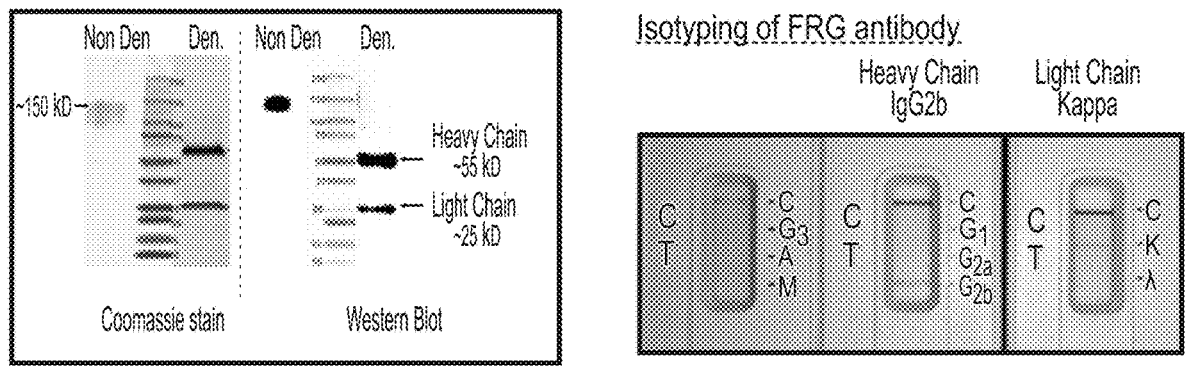
FIGS. 1A-1D depict the characterization of the FRG monoclonal antibody (mAb).
Figure 1B:
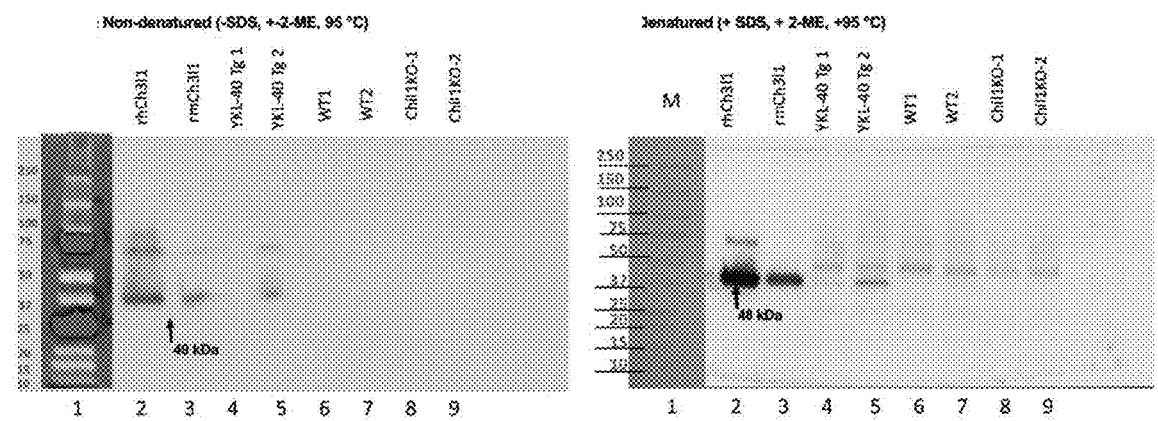
Figure 1C:
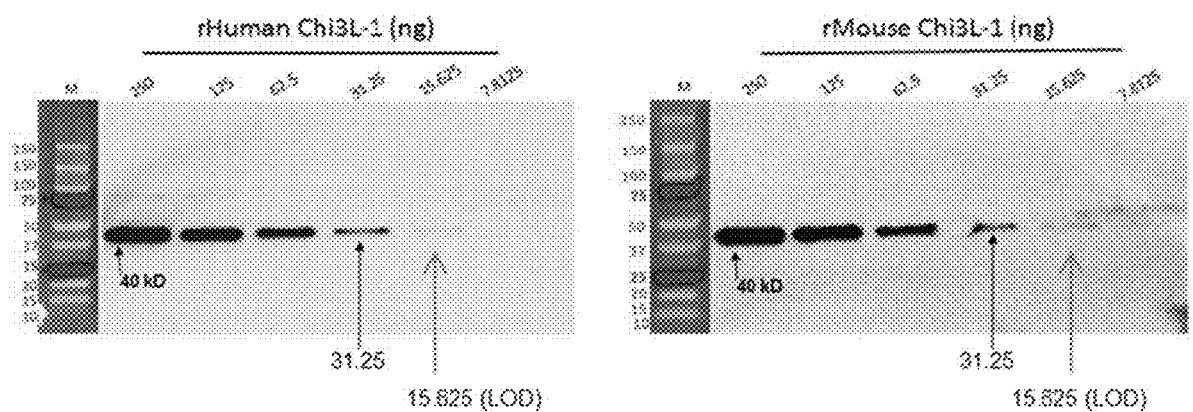
Figure 1D:
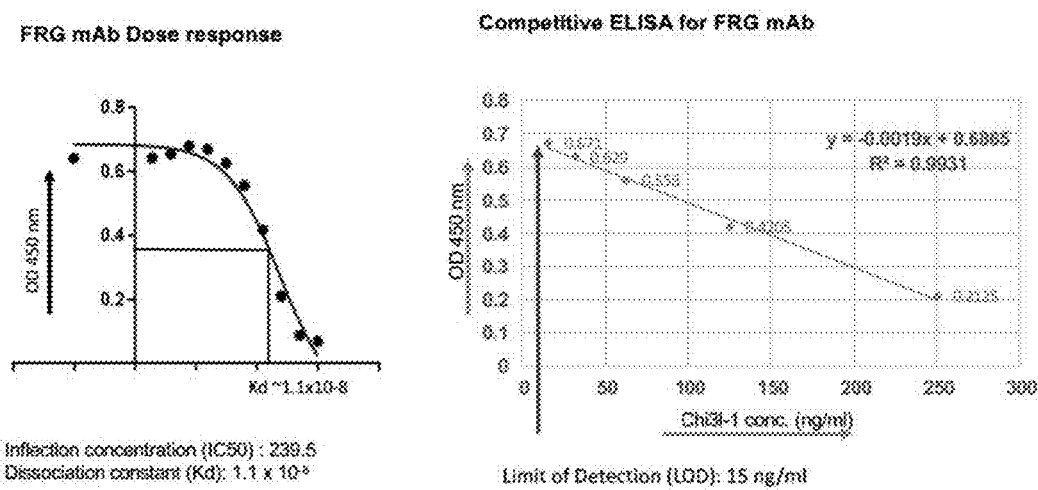

Described herein are combinatorial treatments for cancer, e.g., using the synergistic effect of targeting both CHI3L1 and immune checkpoints. Such synergistic effects are demonstrated herein. Additionally, CHI3L1 is regulated by the interaction of Sema7A with β1-integrin and PlexinC1. Specifically, Sema7A bound to β1-integrin stimulates CHI3L1 expression and activity, while Sema7A bound to PlexinC1 inhibits the expression and activity of CHI3L1. Thus, CHI3L1 can be inhibited by directly targeting CHI3L1, indirectly targeting CHI3L1 (e.g., by targeting its receptors), or by inhibiting semaphorin 7a (Sema7A), inhibiting β1-integrin, or agonizing PlexinC1.

Accordingly, in one aspect of any of the embodiments, provided herein is a method of treating cancer in a subject in need thereof, the method comprising administering a) an inhibitor of an immune checkpoint protein and b) at least one of: an inhibitor of CHI3L1, an inhibitor of Sema7A, an inhibitor of β1-integrin, and/or an agonist of PlexinC1. In some embodiments of any of the aspects, the method comprises administering a) an inhibitor of an immune checkpoint protein and b) two or more of: an inhibitor of CHI3L1, an inhibitor of Sema7A, an inhibitor of β1-integrin, and/or an agonist of PlexinC1 in combination with an inhibitor of an immune checkpoint protein. In some embodiments of any of the aspects, the method comprises administering, a) an inhibitor of an immune checkpoint protein and b) three or more of an inhibitor of CHI3L1, an inhibitor of Sema7A, an inhibitor of β1-integrin, and/or an agonist of PlexinC1. In some embodiments of any of the aspects, the method comprises administering, in combination with an inhibitor of an immune checkpoint protein, all of an inhibitor of CHI3L1, an inhibitor of Sema7A, an inhibitor of β1-integrin, and/or an agonist of PlexinC1. Table 4 depicts exemplary but non-limiting examples of pairwise combinations of the agents which can be administered in the foregoing methods, e.g., in combination with an inhibitor of an immune checkpoint protein.

TABLE 4

| | INHIBITOR OF CHI3L1 | INHIBITOR OF SEMA7A | INHIBITOR OF B1-INTEGRIN | AGONIST OF PLEXINC1 |
|---|---|---|---|---|
| INHIBITOR OF CHI3L1 | | X | X | X |
| INHIBITOR OF SEMA7A | X | | X | X |
| INHIBITOR OF B1-INTEGRIN | X | X | | X |
| AGONIST OF PLEXINC1 | X | X | X | |

In some embodiments of any of the aspects two or more individual reagents of each of the categories of an inhibitor of an immune checkpoint protein, an inhibitor of CHI3L1, an inhibitor of Sema7A, an inhibitor of β1-integrin, and/or an agonist of PlexinC1 can be administered, e.g., two different inhibitors of an immune checkpoint protein or two different Sema7A inhibitors.

In one aspect of any of the embodiments, provided herein is a method of treating cancer in a subject in need thereof, the method comprising administering an inhibitor of CHI3L1; and an inhibitor of an immune checkpoint protein.

As used herein, "inhibitor" refers to an agent which can decrease the expression and/or activity of a target, e.g. by at least 10% or more, e.g. by 10% or more, 50% or more, 70% or more, 80% or more, 90% or more, 95% or more, or 98% or more. The efficacy of an inhibitor of one or more targets, e.g. its ability to decrease the level and/or activity of the target can be determined, e.g. by measuring the level of an expression product of the target and/or the activity of the target. Methods for measuring the level of a given mRNA and/or polypeptide are known to one of skill in the art, e.g. RT-PCR with primers can be used to determine the level of RNA and Western blotting with an antibody can be used to determine the level of a polypeptide. The activity of, e.g. CHI3L1, can be determined using methods known in the art. In some embodiments of any of the aspects, the inhibitor can be an inhibitory nucleic acid; an aptamer; an antibody reagent; an antibody; or a small molecule. An inhibitor of a target described herein can inhibit the activity, expression, or accumulation of the target polypeptide.

Inhibitors of, e.g., CHI3L1, can include inhibitors that act directly on the target itself (e.g., that bind to the CHI3L1 protein or transcript, e.g., direct inhibitors) or inhibitors that act indirectly on the target, e.g., directly on one or more receptors for CHI3L1. As used herein, "CHI3L1," "chitinase-3-like-1 protein," or "YKL-40" refers to a ~40 kDa glycoprotein secreted by at least macrophages, chondrocytes, neutrophils, synovial cells, and some cancer cells. CHI3L1 does not have chitinase activity, is a Th2 promoting cytokine, has been linked to the AKT anti-apoptotic signaling pathway and induces the migration of astrocytes. The sequences of CHI3L1 expression products are known for a number of species, e.g., human CHI3L1 (NCBI Gene ID No: 1116) mRNA (SEQ ID NO: 59; NCBI Ref Seq: NM_001276.1 and SEQ ID NO: 26; NCBI Ref Seq: NM_001276.2) and polypeptide (SEQ ID NO: 27; NCBI Ref Seq: NP_001267.1 and SEQ ID NO: 28; NCBI Ref Seq: NP_001267.2). Chitinase 3-like-1 is referred to in the art as Chi1l.

In some embodiments of any of the aspects the inhibitor of CHI3L1 is poly (I:C), which is known in the art and described in more detail at, e.g., Ma et al. Scientific Reports 2016 6:26299; which is incorporated by reference herein in its entirety.

In some embodiments of any of the aspects, an inhibitor of a specified target is an antibody, antibody reagent, antigen-binding fragment thereof, or CAR that specifically binds to the target. In some embodiments of any of the aspects, the inhibitor of CHI3L1 is an antibody, antibody reagent, antigen-binding fragment thereof, or CAR that specifically binds to CHI3L1.

As used herein, the term "antibody" refers to immunoglobulin molecules and immunologically active portions of immunoglobulin molecules, i.e., molecules that contain an antigen binding site that immunospecifically binds an antigen. The term also refers to antibodies comprised of two immunoglobulin heavy chains and two immunoglobulin light chains as well as a variety of forms including full length antibodies and antigen-binding portions thereof; including, for example, an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody (dAb), a diabody, a multispecific antibody, a dual specific antibody, an anti-idiotypic antibody, a bispecific antibody, a functionally active epitope-binding portion thereof, and/or bifunctional hybrid antibodies.

Each heavy chain is composed of a variable region of said heavy chain (abbreviated here as HCVR or VH) and a constant region of said heavy chain. The heavy chain constant region consists of three domains CH1, CH2 and CH3. Each light chain is composed of a variable region of said light chain (abbreviated here as LCVR or VL) and a constant region of said light chain. The light chain constant region consists of a CL domain. The VH and VL regions may be further divided into hypervariable regions referred to as complementarity-determining regions (CDRs) and interspersed with conserved regions referred to as framework regions (FR). Each VH and VL region thus consists of three CDRs and four FRs which are arranged from the N terminus to the C terminus in the following order: FR1, CDR1, FR2, CDR2, FR3, CDR3, FR4. This structure is well known to those skilled in the art.

As used herein, the term "CDR" refers to the complementarity determining regions within antibody variable sequences. There are three CDRs in each of the variable regions of the heavy chain and of the light chain, which are designated CDR1, CDR2 and CDR3, for each of the variable regions. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Other boundaries defining CDRs overlapping with the Kabat CDRs have been described by Padlan (FASEB J. 9:133-139 (1995)) and MacCallum (J Mol Biol 262(5):732-45 (1996)) and Chothia (J. Mol. Biol. 196:901-917 (1987) and Nature 342:877-883 (1989)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat defined CDRs. The CDR's identified herein, e.g., SEQ ID NOs 1-6 are identified by the Kabat system (see, e.g. FIGS. 7 and 8).

The term "antigen-binding portion" of an antibody refers to one or more portions of an antibody as described herein, said portions) still having the binding affinities as defined above herein. Portions of a complete antibody have been shown to be able to carry out the antigen-binding function of an antibody. In accordance with the term "antigen-binding portion" of an antibody, examples of binding portions include (i) an Fab portion, i.e., a monovalent portion composed of the VL, VH, CL and CH1 domains; (ii) an F(ab')2 portion, i.e., a bivalent portion comprising two Fab portions linked to one another in the hinge region via a disulfide bridge; (iii) an Fd portion composed of the VH and CH1 domains; (iv) an Fv portion composed of the FL and VH domains of a single arm of an antibody; and (v) a dAb portion consisting of a VH domain or of VH, CH1, CH2, DH3, or VH, CH2, CH3 (dAbs, or single domain antibodies, comprising only VL domains have also been shown to specifically bind to target eptiopes). Although the two domains of the Fv portion, namely VL and VH, are encoded by separate genes, they may further be linked to one another using a synthetic linker, e.g., a poly-G4S amino acid sequence ('G4S' disclosed as SEQ ID NO: 29), and recombinant methods, making it possible to prepare them as a single protein chain in which the VL and VH regions combine in order to form monovalent molecules (known as single chain Fv (ScFv)). The term "antigen-binding portion" of an antibody is also intended to comprise such single chain antibodies. Other forms of single chain antibodies such as "diabodies" are likewise included here. Diabodies are bivalent, bispecific antibodies in which VH and VL domains are expressed on a single polypeptide chain, but using a linker which is too short for the two domains being able to combine on the same chain, thereby forcing said domains to pair with complementary domains of a different chain and to form two antigen-binding sites. An immunoglobulin constant domain refers to a heavy or light chain constant domain. Human IgG heavy chain and light chain constant domain amino acid sequences are known in the art.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments of any of the aspects, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments as well as complete antibodies.

An antibody can have the structural features of IgA, IgG, IgE, IgD, IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

Furthermore, an antibody, antigen-binding portion thereof, or CAR as described herein may be part of a larger immunoadhesion molecule formed by covalent or noncovalent association of said antibody or antibody portion with one or more further proteins or peptides. Relevant to such immunoadhesion molecules are the use of the streptavidin core region in order to prepare a tetrameric scFv molecule and the use of a cystein residue, a marker peptide and a C-terminal polyhistidinyl, e.g., hexahistidinyl tag ('hexahistidinyl tag' disclosed as SEQ ID NO: 40) in order to produce bivalent and biotinylated scFv molecules.

In some embodiments of any of the aspects, the antibody, antibody reagent, antigen-binding portion thereof, or CAR described herein can be an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, a bispecific antibody, and a functionally active epitope-binding portion thereof.

In some embodiments of any of the aspects, the antibody or antigen-binding portion thereof is a fully human antibody. In some embodiments of any of the aspects, the antibody, antigen-binding portion thereof, is a humanized antibody or antibody reagent. In some embodiments of any of the aspects, the antibody, antigen-binding portion thereof, is a fully humanized antibody or antibody reagent. In some embodiments of any of the aspects, the antibody or antigen-binding portion thereof, is a chimeric antibody or antibody reagent. In some embodiments of any of the aspects, the antibody, antigen-binding portion thereof, is a recombinant polypeptide. In some embodiments of any of the aspects, the CAR comprises an extracellular domain that binds the target, wherein the extracellular domain comprises a humanized or chimeric antibody or antigen-binding portion thereof. In some embodiments of any of the aspects, the CAR comprises an extracellular domain that binds CHI3L1, wherein the extracellular domain comprises a humanized or chimeric antibody or antigen-binding portion thereof.

The term "human antibody" refers to antibodies whose variable and constant regions correspond to or are derived from immunoglobulin sequences of the human germ line, as described, for example, by Kabat et al. (see Kabat, et al. (1991) Sequences of Proteins of Immunological Interest, Fifth Edition, U.S. Department of Health and Human Services, NIH Publication No. 91-3242). However, the human antibodies can contain amino acid residues not encoded by human germ line immunoglobulin sequences (for example mutations which have been introduced by random or site-specific mutagenesis in vitro or by somatic mutation in vivo), for example in the CDRs, and in particular in CDR3. Recombinant human antibodies as described herein have variable regions and may also contain constant regions derived from immunoglobulin sequences of the human germ line (see Kabat, E. A., et al. (1991) Sequences of Proteins of Immunological Interest, Fifth Edition, U.S. Department of Health and Human Services, NIH Publication No. 91-3242). According to particular embodiments, however, such recombinant human antibodies are subjected to in-vitro mutagenesis (or to a somatic in-vivo mutagenesis, if an animal is used which is transgenic due to human Ig sequences) so that the amino acid sequences of the VH and VL regions of the recombinant antibodies are sequences which although related to or derived from VH and VL sequences of the human germ line, do not naturally exist in vivo within the human antibody germ line repertoire. According to particular embodiments, recombinant antibodies of this kind are the result of selective mutagenesis or back mutation or of both. Preferably, mutagenesis leads to an affinity to the target which is greater, and/or an affinity to non-target structures which is smaller than that of the parent antibody. Generating a humanized antibody from the sequences and information provided herein can be practiced by those of ordinary skill in the art without undue experimentation. In one approach, there are four general steps employed to humanize a monoclonal antibody, see, e.g., U.S. Pat. Nos. 5,585,089; 6,835,823; 6,824,989. These are: (1) determining the nucleotide and predicted amino acid sequence of the starting antibody light and heavy variable domains; (2) designing the humanized antibody, i.e., deciding which antibody framework region to use during the humanizing process; (3) the actual humanizing methodologies/techniques; and (4) the transfection and expression of the humanized antibody.

Usually the CDR regions in humanized antibodies and human antibody variants are substantially identical, and more usually, identical to the corresponding CDR regions in the mouse or human antibody from which they were derived. In some embodiments of any of the aspects, it is possible to make one or more conservative amino acid substitutions of CDR residues without appreciably affecting the binding affinity of the resulting humanized immunoglobulin or human antibody variant. In some embodiments of any of the aspects, substitutions of CDR regions can enhance binding affinity.

The term "chimeric antibody" refers to antibodies which contain sequences for the variable region of the heavy and light chains from one species and constant region sequences from another species, such as antibodies having murine heavy and light chain variable regions linked to human constant regions. Humanized antibodies have variable region framework residues substantially from a human antibody (termed an acceptor antibody) and complementarity determining regions substantially from a non-human antibody, e.g., a mouse-antibody, (referred to as the donor immunoglobulin). The constant region(s), if present, are also substantially or entirely from a human immunoglobulin. The human variable domains are usually chosen from human antibodies whose framework sequences exhibit a high degree of sequence identity with the (murine) variable region domains from which the CDRs were derived. The heavy and light chain variable region framework residues can be substantially similar to a region of the same or different human antibody sequences. The human antibody sequences can be the sequences of naturally occurring human antibodies or can be consensus sequences of several human antibodies.

In addition, techniques developed for the production of "chimeric antibodies" by splicing genes from a mouse, or other species, antibody molecule of appropriate antigen specificity together with genes from a human antibody molecule of appropriate biological activity can be used. The variable segments of chimeric antibodies are typically linked to at least a portion of an immunoglobulin constant region (Fc), typically that of a human immunoglobulin. Human constant region DNA sequences can be isolated in accordance with well-known procedures from a variety of human cells, such as immortalized B-cells. The antibody can contain both light chain and heavy chain constant regions. The heavy chain constant region can include CH1, hinge, CH2, CH3, and, sometimes, CH4 regions. For therapeutic purposes, the CH2 domain can be deleted or omitted.

Additionally, and as described herein, a recombinant humanized antibody can be further optimized to decrease potential immunogenicity, while maintaining functional activity, for therapy in humans. In this regard, functional activity means a polypeptide capable of displaying one or more known functional activities associated with a recombinant antibody, antigen-binding portion thereof, or CAR as described herein. Such functional activities include binding to cancer cells and/or anti-cancer activity. Additionally, a polypeptide having functional activity means the polypeptide exhibits activity similar, but not necessarily identical to, an activity of a reference antibody, antigen-binding portion thereof, or CAR as described herein, including mature forms, as measured in a particular assay, such as, for example, a biological assay, with or without dose dependency. In the case where dose dependency does exist, it need not be identical to that of the reference antibody, antigen-binding portion thereof, or CAR, but rather substantially similar to the dose-dependence in a given activity as compared to the reference antibody, antigen-binding portion thereof, or CAR as described herein (i.e., the candidate polypeptide will exhibit greater activity, or not more than about 25-fold less, about 10-fold less, or about 3-fold less activity relative to the antibodies, antigen-binding portions, and/or CARS described herein).

In some embodiments of any of the aspects, the antibody reagents (e.g., antibodies or CARS) described herein are not naturally-occurring biomolecules. For example, a murine antibody raised against an antigen of human origin would not occur in nature absent human intervention and manipulation, e.g., manufacturing steps carried out by a human. Chimeric antibodies are also not naturally-occurring biomolecules, e.g., in that they comprise sequences obtained from multiple species and assembled into a recombinant molecule. In certain particular embodiments, the human antibody reagents described herein are not naturally-occurring biomolecules, e.g., fully human antibodies directed against a human antigen would be subject to negative selection in nature and are not naturally found in the human body.

In some embodiments of any of the aspects, the antibody, antibody reagent, antigen-binding portion thereof, and/or CAR is an isolated polypeptide. In some embodiments of any of the aspects, the antibody, antibody reagent, antigen-binding portion thereof, and/or CAR is a purified polypeptide. In some embodiments of any of the aspects, the antibody, antibody reagent, antigen-binding portion thereof, and/or CAR is an engineered polypeptide.

In one aspect of any of the embodiments, described herein is an antibody, antigen-binding fragment thereof, antigen reagent or chimaeric antigen receptor (CAR) which is an inhibitor of CHI3L1 specifically binds a CHI3L1 polypeptide. In some embodiments of any of the aspects, the antibody, antigen-binding fragment thereof, antigen reagent or CAR which is an inhibitor of CHI3L1 comprises at least one heavy or light chain complementarity determining region (CDR) selected from the group consisting of:
  (a) a light chain CDR1 having the amino acid sequence of SEQ ID NO: 4;
  (b) a light chain CDR2 having the amino acid sequence of SEQ ID NO: 5;
  (c) a light chain CDR3 having the amino acid sequence of SEQ ID NO: 6;
  (d) a heavy chain CDR1 having the amino acid sequence of SEQ ID NO: 1;
  (e) a heavy chain CDR2 having the amino acid sequence of SEQ ID NO: 2; and (f) a heavy chain CDR3 having the amino acid sequence of SEQ ID NO: 3; or a conservative substitution variant of one or more of (a)-(f). In some embodiments of any of the aspects, the antibody, antigen-binding fragment thereof, antigen reagent or CAR comprises at least one heavy or light chain complementarity determining region (CDR) selected from the group consisting of:

(a) a light chain CDR1 having the amino acid sequence of SEQ ID NO: 4;

(b) a light chain CDR2 having the amino acid sequence of SEQ ID NO: 5;

(c) a light chain CDR3 having the amino acid sequence of SEQ ID NO: 6;

(d) a heavy chain CDR1 having the amino acid sequence of SEQ ID NO: 1;

(e) a heavy chain CDR2 having the amino acid sequence of SEQ ID NO: 2; and (f) a heavy chain CDR3 having the amino acid sequence of SEQ ID NO: 3.

In one aspect of any of the embodiments, described herein is an antibody, antigen-binding fragment thereof, antigen reagent or chimaeric antigen receptor (CAR) which is an inhibitor of CHI3L1 specifically binds a CHI3L1 polypeptide. In some embodiments of any of the aspects, the antibody, antigen-binding fragment thereof, antigen reagent or CAR which is an inhibitor of CHI3L1 comprises a heavy chain CDR3 having the amino acid sequence of SEQ ID NO: 3. In some embodiments of any of the aspects, the antibody, antigen-binding fragment thereof, antigen reagent or CAR comprises a heavy chain CDR1 having the amino acid sequence of SEQ ID NO: 1; a heavy chain CDR2 having the amino acid sequence of SEQ ID NO: 2; and a heavy chain CDR3 having the amino acid sequence of SEQ ID NO: 3.

In some embodiments of any of the aspects, the antibody, antibody reagent, antigen-binding portion thereof, or CAR that specifically binds an CHI3L1 polypeptide binds specifically to an epitope selected from SEQ ID NOs: 13-24. In some embodiments of any of the aspects, the antibody, antibody reagent, antigen-binding portion thereof, or CAR that specifically binds an CHI3L1 polypeptide binds specifically to the epitope of SEQ ID NO: 13.

In some embodiments of any of the aspects, the antibody, antigen-binding fragment thereof, antigen reagent or CAR which is an inhibitor of CHI3L1 comprises heavy chain CDRs having the amino acid sequences of SEQ ID NOs: 1-3. In some embodiments of any of the aspects, the antibody, antigen-binding fragment thereof, antigen reagent or CAR comprises heavy chain CDRs having the amino acid sequences of SEQ ID NOs: 1-3 or a conservative substitution variant of such amino acid sequence.

In some embodiments of any of the aspects, the antibody, antigen-binding fragment thereof, antigen reagent or CAR which is an inhibitor of CHI3L1 comprises light chain CDRs having the amino acid sequences of SEQ ID NOs: 4-6. In some embodiments of any of the aspects, the antibody, antigen-binding fragment thereof, antigen reagent or CAR which is an inhibitor of CHI3L1 comprises light chain CDRs having the amino acid sequences of SEQ ID NOs: 4-6 or a conservative substitution variant of such amino acid sequence.

In some embodiments of any of the aspects, the antibody, antigen-binding fragment thereof, antigen reagent or CAR which is an inhibitor of CHI3L1 comprises the heavy or light chain complementarity determining region (CDR)s as follows:

(a) a light chain CDR1 having the amino acid sequence of SEQ ID NO: 4;

(b) a light chain CDR2 having the amino acid sequence of SEQ ID NO: 5;

(c) a light chain CDR3 having the amino acid sequence of SEQ ID NO: 6;

(d) a heavy chain CDR1 having the amino acid sequence of SEQ ID NO: 1;

(e) a heavy chain CDR2 having the amino acid sequence of SEQ ID NO: 2; and (f) a heavy chain CDR3 having the amino acid sequence of SEQ ID NO: 3.

In some embodiments of any of the aspects, the antibody, antigen-binding fragment thereof, antigen reagent or CAR which is an inhibitor of CHI3L1 comprises the heavy or light chain complementarity determining region (CDR)s as follows:

(a) a light chain CDR1 having the amino acid sequence of SEQ ID NO: 4;

(b) a light chain CDR2 having the amino acid sequence of SEQ ID NO: 5;

(c) a light chain CDR3 having the amino acid sequence of SEQ ID NO: 6;

(d) a heavy chain CDR1 having the amino acid sequence of SEQ ID NO: 1;

(e) a heavy chain CDR2 having the amino acid sequence of SEQ ID NO: 2; and (f) a heavy chain CDR3 having the amino acid sequence of SEQ ID NO: 3; or a conservative substitution variant of the amino acid sequence of any of (a)-(f). In some embodiments of any of the aspects, the antibody, antibody reagent, antigen-binding portion thereof, or CAR that specifically binds an CHI3L1 polypeptide binds specifically to an epitope selected from SEQ ID NOs: 13-24. In some embodiments of any of the aspects, the antibody, antibody reagent, antigen-binding portion thereof, or CAR that specifically binds an CHI3L1 polypeptide binds specifically to the epitope of SEQ ID NO: 13.

In some embodiments of any of the aspects, the antibody, antibody reagent, antigen-binding portion thereof, or CAR which is an inhibitor of CHI3L1 can comprise one or more CDRs (e.g., one CDR, two CDRs, three CDRs, four CDRs, five CDRs, or six CDRs) having the sequence of a CDR selected from SEQ ID NOs: 1-6. In some embodiments of any of the aspects, the antibody, antibody reagent, antigen-binding portion thereof, or CAR which is an inhibitor of CHI3L1 can comprise CDRs having the sequence of the CDRs of SEQ ID NOs: 1-6.

In one aspect of any of the embodiments, described herein is an antibody, antibody reagent, antigen-binding portion thereof, or CAR which is an inhibitor of CHI3L1 that specifically binds an CHI3L1 polypeptide, and can compete for binding of CHI3L1 with an antibody comprising light chain CDRs having the amino acid sequences of SEQ ID NOs: 4-6 and heavy chain CDRs having the amino acid sequences of SEQ ID NOs: 1-3.

In some embodiments of any of the aspects, the antibody, antibody reagent, antigen-binding portion thereof, or CAR can comprise a heavy chain sequence having the amino acid sequence of SEQ ID NO: 36 and/or a light chain sequence having the amino acid sequence of SEQ ID NO: 38.

FRG Heavy chain sequence
(SEQ ID NO: 36)
QIQLVQSGPELKKPGETVKISCKASGYTFTNYGMNWVKQAPGKGLKWMGW

INTYTGEPTYADDFKGRFAFSLETSASTAYLQINNLRNEDMSTYFCARLG

YGKFYVMDYWGQGTSVTVSS

FRG Heavy chain nucleotide sequence
(SEQ ID NO: 37)
CAGATCCAGTTGGTGCAGTCTGGACCTGAGCTGAAGAAGCCTGGAGAGAC

AGTCAAGATCTCCTGCAAGGCTTCTGGGTATACCTTCACAAACTATGGAA

TGAACTGGGTGAAGCAGGCTCCAGGAAAGGGTTTAAAGTGGATGGGCTGG

ATAAATACCTACACTGGAGAGCCAACATATGCTGATGACTTCAAGGGACG

GTTTGCCTTCTCTTTGGAAACCTCTGCCAGCACTGCCTATTTGCAGATCA

ACAACCTCAGAAATGAGGACATGTCTACATATTTCTGTGCAAGATTGGGA

TATGGTAAATTCTATGTTATGGACTACTGGGGTCAGGGAACGTCAGTCAC

CGTCTCCTCA

FRG Light chain sequence
(SEQ ID NO: 38)
DVVMTQTPLSLPVSLGDQASISCRSSQSLVHSNGNTYLHWYLQKPGQSPK

WYKVSNRFSGVPDRFSGSGSGTDFTLKISRVEAEDLGVYFCSQSTHVTWT

FGGGTKLEIK

FRG Heavy chain nucleotide sequence
(SEQ ID NO: 39)
GATGTTGTGATGACCCAAACTCCACTCTCCCTGCCTGTCAGTCTTGGAGAT

CAAGCCTCCATCTCTTGCAGATCTAGTCAGAGCCTTGTACACAGTAATGGA

AACACCTATTTACATTGGTACCTGCAGAAGCCAGGCCAGTCTCCAAAGCTC

CTGATCTACAAAGTTTCCAACCGATTTTCTGGGGTCCCAGACAGGTTCAGT

GGCAGTGGATCAGGGACAGATTTCACACTCAAGATCAGCAGAGTGGAGGCT

GAGGATCTGGGAGTTTATTTCTGCTCTCAAAGTACACATGTTACGTGGACG

TTCGGTGGAGGCACCAAGCTGGAAATCAAA

In some embodiments of any of the aspects, the antibody, antibody reagent, antigen-binding portion thereof, or CAR which is an inhibitor of CHI3L1 that specifically binds an CHI3L1 polypeptide binds specifically to an epitope selected from SEQ ID NOs: 13-24. In some embodiments of any of the aspects, the antibody, antibody reagent, antigen-binding portion thereof, or CAR that specifically binds an CHI3L1 polypeptide binds specifically to the epitope of SEQ ID NO: 13.

Additional anti-CHI3L1 reagents are known in the art which can be used in the methods described herein, including Cat Nos. PA5-46996, PA5-43746, PA5-37357, and PA5-47363 from Invitrogen (Invitrogen Life Tech, Carlsbad, Calif.) and antibody reagents comprising one or more (e.g., all six) of the CDRs of those antibodies.

In some embodiments of any of the aspects, the antibody, antibody reagent, antigen-binding portion thereof, and/or CAR as described herein can be a variant of a sequence described herein, e.g., a conservative substitution variant of an antibody polypeptide. In some embodiments of any of the aspects, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or portion thereof that retains activity, e.g., antigen-specific binding activity for the relevant target polypeptide, e.g., CHI3L1. A wide variety of PCR-based site-specific mutagenesis approaches are also known in the art and can be applied by the ordinarily skilled artisan.

One of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retain the ability to specifically bind the target antigen (e.g., CHI3L1). Such conservatively modified variants are in addition to and do not exclude polymorphic variants, interspecies homologs, and alleles consistent with the disclosure.

Examples of substitution variants include conservative substitution of amino acids, e.g., in a $V_H$ or $V_L$, domain, that do not alter the sequence of a CDR. A conservative substitution in a sequence not comprised by a CDR can be a substitution relative to a wild-type or naturally-occurring sequence, e.g., human or murine framework and/or constant regions of an antibody sequence. In some embodiments of any of the aspects, a conservatively modified variant of an antibody reagent can comprise alterations other than in the CDRs, e.g., a conservatively modified variant of an antibody, antibody reagent, antigen-binding portion thereof, or CAR which is an inhibitor of CHI3L1 can comprise CDRs having the sequence of one or more of SEQ ID NOs 1-6. In some embodiments of any of the aspects, a conservatively modified variant of an antibody, antibody reagent, antigen-binding portion thereof, or CAR which is an inhibitor of CHI3L1 can comprise CDRs having the sequences of SEQ ID NOs: 1-6.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g., antigen-binding activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

A variant amino acid or DNA sequence preferably is at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g., BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required.

Any cysteine residue not involved in maintaining the proper conformation of the polypeptide also can be substituted, generally with serine, to improve the oxidative stability of the molecule and prevent aberrant crosslinking. Conversely, a cysteine bond(s) can be added to the polypeptide to improve its stability or facilitate oligomerization.

In particular embodiments wherein an antibody, antigen-binding portion thereof, or CAR which is an inhibitor of CHI3L1 comprises at least one CDR which is not identical to the sequence of SEQ ID NOs: 1-6, the amino acid sequence of that at least one CDR can be selected by methods well known to one of skill in the art. For example, Fujii, 2004, "Antibody affinity maturation by random mutagenesis" in Methods in Molecular Biology: Antibody Engineering 248: 345-349 (incorporated by reference herein in its entirety), particularly at FIG. 2 and Section 3.3, describes methods of generating a library for any CDR of interest. This allows one of ordinary skill in the art to identify alternative CDRs, including conservative substitution variants of the specific CDR sequences described herein, which, when present in an antibody or antigen-binding portion thereof as described herein, will result in an antigen or antigen-binding portion thereof which will bind a cancer cell surface antigen. The method described in Fujii et al. also permits one of ordinary skill in the art to screen for a light chain sequence which will give the desired binding behavior when combined with a known heavy chain fragment and vice versa.

In some embodiments of any of the aspects, a CAR which is an inhibitor of CHI3L1 comprises an extracellular domain comprising an anti-CHI3L1 antibody or antigen-binding portion thereof that binds one or more epitopes of a CHI3L1 polypeptide; a transmembrane domain, one or more intracellular co-stimulatory signaling domains, and a primary signaling domain. Exemplary anti-CHI3L1 antibodies and antigen-binding portions thereof, as well as exemplary epitopes, are described elsewhere herein As used herein, "chimeric antigen receptor" or "CAR" refers to an artificially constructed hybrid polypeptide comprising an antigen-binding domain (e.g., an antigen-binding portion of an antibody (e.g., a scFV)), a transmembrane domain, and a T-cell signaling and/or T-cell activation domain. CARS have the ability to redirect T-cell specificity and reactivity toward a selected target in a non-MHC-restricted manner, exploiting the antigen-binding properties of monoclonal antibodies. The non-MHC-restricted antigen recognition gives T-cells expressing CARS the ability to recognize an antigen independent of antigen processing, thus bypassing a major mechanism of tumor escape. Moreover, when expressed in T-cells, CARs advantageously do not dimerize with endogenous T-cell receptor (TCR) alpha and beta chains. Most commonly, the CAR's extracellular binding domain is composed of a single chain variable fragment (scFv) derived from fusing the variable heavy and light regions of a murine or humanized monoclonal antibody. Alternatively, scFvs may be used that are derived from Fab's (instead of from an antibody, e.g., obtained from Fab libraries), in various embodiments, this scFv is fused to a transmembrane domain and then to an intracellular signaling domain. "First-generation" CARs include those that solely provide CD3zeta (CD3ζ) signals upon antigen binding, "Second-generation" CARS include those that provide both costimulation (e.g., CD28 or CD 137) and activation (CD3ζ). "Third-generation" CARs include those that provide multiple costimulatory (e.g., CD28 and CD 137) domains and activation domains (e.g., CD3ζ). In various embodiments, the CAR is selected to have high affinity or avidity for the antigen. Further discussion of CARs can be found, e.g., in Maus et al. Blood 2014 123:2624-35; Reardon et al. Neuro-Oncology 2014 16:1441-1458; Hoyos et al. Haematologica 2012 97:1622; Byrd et al. J Clin Oncol 2014 32:3039-47; Maher et al. Cancer Res 2009 69:4559-4562; and Tamada et al. Clin Cancer Res 2012 18:6436-6445; each of which is incorporated by reference herein in its entirety.

In some embodiments of any of the aspects, a CAR which is an inhibitor of CHI3L1 comprises an extracellular binding domain that comprises a humanized CHI3L1-specific binding domain; a transmembrane domain; one or more intracellular co-stimulatory signaling domains; and a primary signaling domain. As used herein, the terms, "binding domain," "extracellular domain," "extracellular binding domain," "antigen-specific binding domain," and "extracellular antigen specific binding domain," are used interchangeably and provide a CAR with the ability to specifically bind to the target antigen of interest, e.g., CHI3L1. The binding domain may be derived either from a natural, synthetic, semi-synthetic, or recombinant source.

In some embodiments of any of the aspects, the CARs contemplated herein may comprise linker residues between the various domains, e.g., added for appropriate spacing and conformation of the molecule. In particular embodiments the linker is a variable region linking sequence. A "variable region linking sequence," is an amino acid sequence that connects the VH and VL domains and provides a spacer function compatible with interaction of the two sub-binding domains so that the resulting polypeptide retains a specific binding affinity to the same target molecule as an antibody that comprises the same light and heavy chain variable regions. CARS contemplated herein, can comprise one, two, three, four, or five or more linkers. In particular embodiments, the length of a linker is about 1 to about 25 amino acids, about 5 to about 20 amino acids, or about 10 to about 20 amino acids, or any intervening length of amino acids. In some embodiments of any of the aspects, the linker is 1, 2, 3, 4, 5, 6, 7, 8, 9, 10, 11, 12, 13, 14, 15, 16, 17, 18, 19, 20, 21, 22, 23, 24, 25, or more amino acids long.

In particular embodiments, the binding domain of the CAR is followed by one or more "spacer domains," which refers to the region that moves the antigen binding domain away from the effector cell surface to enable proper cell/cell contact, antigen binding and activation. The hinge domain may be derived either from a natural, synthetic, semi-synthetic, or recombinant source. In certain embodiments, a spacer domain is a portion of an immunoglobulin, including, but not limited to, one or more heavy chain constant regions, e.g., CH2 and CH3. The spacer domain can include the amino acid sequence of a naturally occurring immunoglobulin hinge region or an altered immunoglobulin hinge region.

The binding domain of the CAR is generally followed by one or more "hinge domains," which plays a role in positioning the antigen binding domain away from the effector cell surface to enable proper cell/cell contact, antigen binding and activation. A CAR generally comprises one or more hinge domains between the binding domain and the transmembrane domain (TM). The hinge domain may be derived either from a natural, synthetic, semi-synthetic, or recombinant source. The hinge domain can include the amino acid sequence of a naturally occurring immunoglobulin hinge region or an altered immunoglobulin hinge region. Illustrative hinge domains suitable for use in the CARS described herein include the hinge region derived from the extracellular regions of type 1 membrane proteins such as CD8α, CD4, CD28 and CD7, which may be wild-type hinge regions from these molecules or may be altered. In another embodiment, the hinge domain comprises a CD8α hinge region.

The "transmembrane domain" is the portion of the CAR that fuses the extracellular binding portion and intracellular signaling domain and anchors the CAR to the plasma membrane of the immune effector cell. The TM domain may be derived either from a natural, synthetic, semi-synthetic, or recombinant source. The TM domain may be derived from (i.e., comprise at least the transmembrane region(s) of) the alpha, beta or zeta chain of the T-cell receptor, CD3ε, CD3ζ, CD4, CD5, CD8α, CD9, CD 16, CD22, CD27, CD28, CD33, CD37, CD45, CD64, CD80, CD86, CD 134, CD137, CD152, CD 154, and PD1.

In some embodiments of any of the aspects, CARS contemplated herein comprise an intracellular signaling domain. An "intracellular signaling domain," refers to the part of a CAR that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain. In some embodiments of any of the aspects, a CAR contemplated herein comprises an intracellular signaling domain that comprises one or more "co-stimulatory signaling domain" and a "primary signaling domain."

Primary signaling domains regulate primary activation of the TCR complex either in a stimulatory way, or in an inhibitory way. Primary signaling domains that act in a stimulatory manner may contain signaling motifs which are known as immunoreceptor tyrosine-based activation motifs or ITAMs. Illustrative examples of 1TAM containing primary signaling domains that are of particular use in the invention include those derived from TCR, FcRγ, FcRβ, CD3γ, CD3δ, CD3ε, CD3ζ, CD22, CD79a, CD79b, and CD66d.

As used herein, the term, "co-stimulatory signaling domain," or "co-stimulatory domain", refers to an intracellular signaling domain of a co-stimulatory molecule. Co-stimulatory molecules are cell surface molecules other than antigen receptors or Fc receptors that provide a second signal required for efficient activation and function of T lymphocytes upon binding to antigen. Illustrative examples of such co-stimulatory molecules include CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), CD278 (ICOS), DAP10, LAT, NKD2C SLP76, TRIM, and ZAP70. In one embodiment, a CAR comprises one or more co-stimulatory signaling domains selected from the group consisting of CD28, CD137, and CD134, and a CD3ζ primary signaling domain.

In some embodiments of any of the aspects, the inhibitor of CHI3L1 signaling described herein is an inhibitor of a CHI3L1 receptor. CHI3L1 receptors include CRTH2 and the heterodimer receptor formed by IL13Rα2 and TMEM219.

As used herein, "CRTH2," "chemoattractant homologous receptor expressed on Th2 cells," "CD294," or "GPR44" refers to a G protein-coupled receptor activated by prostaglandin $D_2$ and/or CHI3L1. Activation of CRTH2 by prostaglandin $D_2$ induces the chemotaxis of Th2 lymphocytes and eosinophils, even in the absence of allergen or co-stimulation. Activation of CRTH2 by CHI3L1 can induce fibroproliferation. In some embodiments of any of the aspects, CRTH2 activity can be measured by measuring CHI3L1-induced fibroproliferation. In some embodiments of any of the aspects, increased CRTH2 activity can be indicated by increased M2 macrophage differentiation. The sequences of CRTH2 expression products for a number of species are known, e.g., human CRTH2 (NCBI Gene ID: 11251) mRNA (NCBI Ref Seq: NM_004778) and polypeptide (NCBI Ref Seq: NP_004769).

As used herein, "IL-13Rα2," "Interleukin-13 receptor subunit alpha-2," or "CD213A2" refers to a membrane bound protein that forms a heterodimer with TMEM219 to form a CHI3L1 receptor. IL13Rα2 also binds to IL-13 with very high affinity, and negatively regulates both IL-13 and TL-4. IL-13Rα2 competes with the IL-13 receptor comprising IL-13Rα1 and IL4Ralpha for binding of IL-13. Sequences for IL-13Rα2 expression products are known for a number of species, e.g., human IL-13Rα2 (NCBI Gene ID: 3598) mRNA (NCBI Ref Seq: NM_000640) and polypeptide (NCBI Ref Seq: NP_000631).

As used herein, "TMEM219" or "transmembrane protein 219" refers to a membrane bound protein that forms a heterodimer with IL-13Rα2 to form a CHI3L1 receptor. Sequences for TMEM219 expression products are known for a number of species, e.g., human TMEM219 (NCBI Gene ID: 124446) mRNA (NCBI Ref Seq: NM_001083613.1 and NM_194280.3) and polypeptide (NCBI Ref Seq: NP_001077082.1 and NP_919256.1).

In some embodiments of any of the aspects, inhibitors of CHI3L1 receptors can be inhibitory antibodies, antibody reagents, antigen-binding fragments thereof, or CARs that bind specifically to the receptor and/or receptor subunit.

Exemplary antibodies, antibody reagents, and/or antigen-binding fragments thereof, which are inhibitors of CHI3L1 receptors are known in the art and can include Cat Nos. PA5-46996, PA5-43746, PA5-37357, and PA5-47363 from Invitrogen (Invitrogen Life Tech, Carlsbad, Calif.)

In some embodiments of any of the aspects, inhibitors (e.g., of Sema7A, β1-integrin, an immune checkpoint protein, CHI3L1 and/or CHI3L1 receptors) can be inhibitory nucleic acid molecules. In some embodiments of any of the aspects, an inhibitory nucleic acid molecule can be a miRNA, iRNA, amiRNA, RNAi molecule or the like.

In some embodiments of any of the aspects, multiple inhibitors or agonists of a given target can be used in the methods and compositions described herein, e.g., two or more inhibitors that target the same target (e.g., CHI3L1), or at least one inhibitor that targets a first target (e.g., CHI3L1) and at least one inhibitor that targets at least one additional target (e.g., one or more CHI3L1 receptors). In some embodiments of any of the aspects, multiple inhibitors of CHI3L1 can be used in the methods and compositions described herein, e.g., two or more inhibitors that target the same target (e.g., CHI3L1), or at least one inhibitor that targets a first target (e.g., CHI3L1) and at least one inhibitor that targets at least one additional target (e.g., one or more CHI3L1 receptors).

As used herein, "semaphorin 7A" or "Sema7A" (also known as CD108) refers to a membrane-bound member of the semaphorin family and which is expressed on activated lymphocytes and erythrocytes. The sequences of Sema7A expression products are known for a number of species, e.g., human Sema7A (NCBI Gene ID No: 8482) mRNA (SEQ ID NO: 41; NCBI Ref Seq: NM_001146029.2, SEQ ID NO: 42 NCBI Ref Seq: 001146030.2 and SEQ ID NO: 43 NCBI Ref Seq: NM_003612.4) and polypeptide (SEQ ID NO: 44 NCBI Ref Seq: NP_001139501.1; SEQ ID NO: 45 NCBI Ref Seq: NP_001139502.1 and SEQ ID NO: 46 NCBI Ref Seq: NP_003603.1).

Inhibitors of Sema7A are known in the art and can include anti-Sema7A antibody reagents or Sema7A inhibitory nucleic acid molecules. Exemplary, non-limiting examples of anati-Sema7A antibodies can include AF1835 from R and D Systems of Minneapolis Minn.; ab8222 (MEM-150), ab23578, ab217628, ab90242 (MM0537-99D22), or ab133803 from AbCam of Cambridge, Mass.; PAS-50753, PAS-28971, or PAS-47246 from ThermoFisher Scientific of Waltham, Mass.; C-6 (sc-374432) from Santa Cruz Biotechnology of Dallas, Tex.; and 191-205 (SAB1105046) or 376-390 (SAB1105047) from Sigma Aldrich of St. Louis, Mo.;

As used herein, "beta 1 integrin" or "β1-integrin" (also known as ITGB1 or CD29) refers to cell surface receptor that interacts with a number of different partners to form receptor complexes. The sequences of β1-integrin expression products are known for a number of species, e.g., human β1-integrin (NCBI Gene ID No: 3688) mRNA (SEQ ID NO: 47; NCBI Ref Seq: NM_002211.3, SEQ ID NO: 48 NCBI Ref Seq: NM_033668.2 and SEQ ID NO: 49* NCBI Ref Seq: NM_133376.2) and polypeptide (SEQ ID NO: 50 NCBI Ref Seq: NP_002202.2; SEQ ID NO: 51 NCBI Ref Seq: NP_391988.1 and SEQ ID NO: 52 NCBI Ref Seq: NP_596867.1).

Inhibitors of β1-integrin are known in the art and can include anti-β1-integrin antibody reagents or β1-integrin inhibitory nucleic acid molecules. Exemplary, non-limiting examples of anti-β1-integrin antibodies can include P5D2 (ab24693), EPR16895 (ab179471), EP1041Y (ab52971), 12G10 (ab30394), ab183666, JB1B (2630388), and BV7 (ab7168) from AbCam of Cambridge, Mass.; 3B6 (MA5-17103), PA5-29606, 44-872G, HMb1-1 (11-0291-82), TS2/16 (11-0299-42), PA5-78028, MEM101A (CD2920), 4B7R (MA5-13658), 2B1 (MA1-06906), KMI6 (14-0292-82) from ThermoFisher Scientific of Waltham, Mass.; M106 (sc-8978) or A-4 (sc-374429) from Santa Cruz Biotechnology of Dallas, Tex.; and MABT409 or AB1952 from Millipore Sigma of Burlington, Mass.

It is further contemplated herein that certain embodiments of any of the aspects can relate to use or administration of both an inhibitor of Sema7A and of β1-integrin for particularly efficacious results. In some embodiments, a single bivalent antibody reagent is an inhibitor of both Sema7A and β1-integrin, e.g., one specificity is for Sema7A and the second specificity is for β1-integrin.

As used herein, "Plexin C1" or "PLXNC1" (also known as CD232 or VESPR) refers to a member of the plexin family of semaphorin receptors that binds Sema7A as well as a number of viral semaphorins. The sequences of Plexin C1 expression products are known for a number of species, e.g., human Plexin C1 (NCBI Gene ID No: 10154) mRNA (SEQ ID NO: 53; NCBI Ref Seq: NM_005761.2) and polypeptide (SEQ ID NO: 54 NCBI Ref Seq: NP_005752.1).

Agonists of Plexin C1 are known in the art and can include Plexin C1 polypeptides, nucleic acids encoding Plexin C1, or nucleic acids encoding Growth Arrest Specific 5 (GAS5, NCBI Gene ID: 60674) which is a known agonist of Plexin C1 (e.g., see Zhao et al. Mol Ther 23:189-19114 (2015); which is incorporated by reference herein in its entirety).

As used herein, the term "agonist" refers to an agent which increases the expression and/or activity of the target by at least 10% or more, e.g. by 10% or more, 50% or more, 100% or more, 200% or more, 500% or more, or 1000% or more. The efficacy of an agonist of, for example, Plexin C1, e.g. its ability to increase the level and/or activity of the target can be determined, e.g. by measuring the level of an expression product of the target and/or the activity of the target. Methods for measuring the level of a given mRNA and/or polypeptide are known to one of skill in the art, e.g. RTPCR with primers can be used to determine the level of RNA, and Western blotting with an antibody can be used to determine the level of a polypeptide. Suitable primers for a given target are readily identified by one of skill in the art, e.g., using software widely available for this purpose (e.g., Primer3 or PrimerBank, which are both available on the world wide web). Non-limiting examples of antibodies to, e.g., PlexinC1, are commercially available, e.g., Cat. No. ab116070 from AbCam (Cambridge, Mass.). Assays for measuring the activity of the targets described herein are provided elsewhere herein. In some embodiments of any of the aspects, an agonist of a given polypeptide can be the polypeptide, a nucleic acid encoding the polypeptide, or a small molecule.

Non-limiting examples of agonists of a given polypeptide target, can include the target polypeptides or variants or functional fragments thereof and nucleic acids encoding the polypeptide or variants or functional fragments thereof. In some embodiments of any of the aspects, the agonist of a given target, is a polypeptide of that target or variants or functional fragment thereof and/or a nucleic acid encoding the polypeptide or variant or functional fragment thereof. In some embodiments of any of the aspects, the polypeptide agonist can be an engineered and/or recombinant polypeptide. In some embodiments of any of the aspects, the polypeptide agonist can be a nucleic acid encoding a polypeptide, e.g. a functional fragment thereof. In some embodiments of any of the aspects, the nucleic acid can be comprised by a vector.

In some embodiments of any of the aspects, a polypeptide agonist can comprise one of the sequences provided below herein for each target. In some embodiments of any of the aspects, a polypeptide agonist can consist essentially of one of the sequences provided below herein for each target. In some embodiments of any of the aspects, a polypeptide agonist can consist of one of the sequences provided below herein for each target. In some embodiments of any of the aspects, an agonist can comprise a nucleic acid encoding one of the sequences provided below herein for each target. In some embodiments of any of the aspects, an agonist can be a polypeptide comprising a reference/wild-type sequence provided herein with at least 80%, at least 85%, at least 90%, at least 95%, or at least 98% identity to the reference/wild-type sequence and which retains the activity of the reference/wild-type sequence.

In some embodiments of any of the aspects, the agonist an exogenous polypeptide. In some embodiments of any of the aspects, the target cell(s) and/or subject is contacted with and/or administered exogenous polypeptide, e.g., the polypeptide is produced in vitro and/or synthesized and purified polypeptide is provided to the target cell(s) and/or subject.

In some embodiments of any of the aspects, the agonist can be a nucleic acid encoding a polypeptide (or a variant or functional fragment thereof) and/or a vector comprising a nucleic acid encoding a polypeptide (or a variant or functional fragment thereof). A nucleic acid encoding a polypeptide can be, e.g., an RNA molecule, a plasmid, and/or an expression vector. In some embodiments of any of the aspects, the nucleic acid encoding a polypeptide can be an mRNA. In some embodiments of any of the aspects, the nucleic acid encoding a polypeptide can be a modified mRNA. In some embodiments of any of the aspects, the agonist can be a nucleic acid encoding a polypeptide, e.g., exogenous and/or ectopic polypeptide. In some embodiments of any of the aspects, the target cell(s) and/or subject is contacted with and/or administered the nucleic acid encoding exogenous and/or ectopic polypeptide, e.g., the nucleic acid is transcribed and/or translated after the contacting or administering step to provide exogenous and/or ectopic to the target cell(s) and/or subject.

The immune system has multiple inhibitory pathways that are critical for maintaining self-tolerance and modulating immune responses. For example, in T-cells, the amplitude and quality of response is initiated through antigen recognition by the T-cell receptor and is regulated by immune checkpoint proteins that balance co-stimulatory and inhibitory signals. In some embodiments of any of the aspects, a subject or patient is treated with at least one inhibitor of an immune checkpoint protein. As used herein, "immune checkpoint protein" refers to a protein which, when active, exhibits an inhibitory effect on immune activity, e.g., T cell activity. Exemplary immune checkpoint proteins can include PD-1 (e.g., NCBI Gene ID: 5133); PD-L1 (e.g., NCBI Gene ID: 29126); PD-L2 (e.g., NCBI Gene ID: 80380); TIM-3 (e.g., NCBI Gene ID: 84868); CTLA4 (e.g., NCBI Gene ID: 1493); TIGIT (e.g., NCBI Gene ID: 201633); KIR (e.g., NCBI Gene ID: 3811); LAG3 (e.g., NCBI Gene ID: 3902); DD1-a (e.g., NCBI Gene ID: 64115); A2AR (e.g., NCBI Gene ID: 135); B7-H3 (e.g., NCBI Gene ID: 80381); B7-H4 (e.g., NCBI Gene ID: 79679); BTLA (e.g., NCBI Gene ID: 151888); IDO (e.g., NCBI Gene ID: 3620); TDO (e.g., NCBI Gene ID: 6999); HVEM (e.g., NCBI Gene ID: 8764); GALS (e.g., NCBI Gene ID: 3965); 2B4 (belongs to the CD2 family of molecules and is expressed on all NK, γδ, and memory CD8+(αβ) T cells) (e.g., NCBI Gene ID: 51744); CD160 (also referred to as BY55) (e.g., NCBI Gene ID: 11126); and various B-7 family ligands. B7 family ligands include, but are not limited to, B7-1, B7-2, B7-DC, B7-H1, B7-H2, B7-H3, B7-H4, B7-H5, B7-H6 and B7-H7.

Programmed cell death 1 (PD-1), limits the activity of T cells in peripheral tissues at the time of an inflammatory response to infection and limits autoimmunity. PD-1 blockade in vitro enhances T-cell proliferation and cytokine production in response to a challenge by specific antigen targets or by allogeneic cells in mixed lymphocyte reactions. A strong correlation between PD-1 expression and response was shown with blockade of PD-1 (Pardoll, Nature Reviews Cancer, 12: 252-264, 2012). PD-1 blockade can be accomplished by a variety of mechanisms including antibodies that bind PD-1 or its ligand, PD-L1. Examples of PD-1 and PD-L1 blockers are described in U.S. Pat. Nos. 7,488,802; 7,943,743; 8,008,449; 8,168,757; 8,217,149, and PCT Published Patent Application Nos: WO03042402, WO2008156712, WO2010089411, WO2010036959, WO2011066342, WO2011159877, WO2011082400, and WO2011161699; which are incorporated by reference herein in their entireties. In certain embodiments the PD-1 inhibitors include anti-PD-L1 antibodies. In certain other embodiments the PD-1 inhibitors include anti-PD-1 antibodies and similar binding proteins such as nivolumab (MDX 1106, BMS 936558, ONO 4538), a fully human IgG4 antibody that binds to and blocks the activation of PD-1 by its ligands PD-L1 and PD-L2; lambrolizumab (MK-3475 or SCH 900475), a humanized monoclonal IgG4 antibody against PD-1; CT-011 a humanized antibody that binds PD-1; AMP-224, a fusion protein of B7-DC; an antibody Fc portion; BMS-936559 (MDX-1105-01) for PD-L1 (B7-H1) blockade. Also specifically contemplated herein are agents that disrupt or block the interaction between PD-1 and PD-L1, such as a high affinity PD-L1 antagonist.

Cytotoxic T-lymphocyte associated antigen 4 (CTLA-4) is an immune checkpoint protein that downregulates pathways of T-cell activation (Fong et al., Cancer Res. 69(2): 609-615, 2009; Weber Cancer Immunol. Immunother, 58:823-830, 2009). Blockade of CTLA-4 has been shown to augment T-cell activation and proliferation. Inhibitors of CTLA-4 include anti-CTLA-4 antibodies. Anti-CTLA-4 antibodies bind to CTLA-4 and block the interaction of CTLA-4 with its ligands CD80/CD86 expressed on antigen presenting cells, thereby blocking the negative down regulation of the immune responses elicited by the interaction of these molecules. Examples of anti-CTLA-4 antibodies are described in U.S. Pat. Nos. 5,811,097; 5,811,097; 5,855,887; 6,051,227; 6,207,157; 6,682,736; 6,984,720; and 7,605,238; which are incorporated by reference herein in their entireties. One anti-CDLA-4 antibody is tremelimumab, (ticilimumab, CP-675,206). In one embodiment, the anti-CTLA-4 antibody is ipilimumab (also known as 10D1, MDX-D010) a fully human monoclonal IgG antibody that binds to CTLA-4. Ipilimumab is marketed under the name YERVOY™ and has been approved for the treatment of unresectable or metastatic melanoma.

Additional anti-CTLA4 antagonists include, but are not limited to, the following: any inhibitor that is capable of disrupting the ability of CD28 antigen to bind to its cognate ligand, to inhibit the ability of CTLA4 to bind to its cognate ligand, to augment T cell responses via the co-stimulatory pathway, to disrupt the ability of B7 to bind to CD28 and/or CTLA4, to disrupt the ability of B7 to activate the co-stimulatory pathway, to disrupt the ability of CD80 to bind to CD28 and/or CTLA4, to disrupt the ability of CD80 to activate the co-stimulatory pathway, to disrupt the ability of CD86 to bind to CD28 and/or CTLA4, to disrupt the ability of CD86 to activate the co-stimulatory pathway, and to disrupt the co-stimulatory pathway, in general from being activated. This necessarily includes small molecule inhibitors of CD28, CD80, CD86, CTLA4, among other members of the co-stimulatory pathway; antibodies directed to CD28, CD80, CD86, CTLA4, among other members of the co-stimulatory pathway; antisense molecules directed against CD28, CD80, CD86, CTLA4, among other members of the co-stimulatory pathway; adnectins directed against CD28, CD80, CD86, CTLA4, among other members of the co-stimulatory pathway, RNAi inhibitors (both single and double stranded) of CD28, CD80, CD86, CTLA4, among other members of the co-stimulatory pathway, among other anti-CTLA4 antagonists.

Other immune-checkpoint inhibitors include lymphocyte activation gene-3 (LAG-3) inhibitors, such as IMP321, a soluble Ig fusion protein (Brignone et al., 2007, J. Immunol. 179:4202-4211). Other immune-checkpoint inhibitors include B7 inhibitors, such as B7-H3 and B7-H4 inhibitors. In particular, the anti-B7-H3 antibody MGA271 (Loo et al., 2012, Clin. Cancer Res. July 15 (18) 3834). Also included are TIM3 (T-cell immunoglobulin domain and mucin domain 3) inhibitors (Fourcade et al., 2010, J. Exp. Med. 207:2175-86 and Sakuishi et al., 2010, J. Exp. Med. 207: 2187-94).

Non-limiting examples of immune checkpoint inhibitors (with checkpoint targets and manufacturers noted in parantheses) can include: MGA271 (B7-H3: MacroGenics); ipilimumab (CTLA-4; Bristol Meyers Squibb); pembrolizumab (PD-1; Merck); nivolumab (PD-1; Bristol Meyers Squibb); atezolizumab (PD-L1; Genentech); galiximab (B7.1; Biogen); IMP321 (LAG3: Immuntep); BMS-986016 (LAG3; Bristol Meyers Squibb); SMB-663513 (CD137; Bristol-Meyers Squibb); PF-05082566 (CD137; Pfizer); IPH2101 (KIR; Innate Pharma); KW-0761 (CCR4; Kyowa Kirin); CDX-1127 (CD27; CeilDex); MEDI-6769 (Ox40; Medimmune); CP-870,893 (CD40; Genentech); tremelimumab (CTLA-4; Medimmune); pidilizumab (PD-1; Medivation); MPDL3280A (PD-L1; Roche); MEDI4736 (PD-L1; AstraZeneca); MSB0010718C (PD-L1; EMD Serono); AUNP12 (PD-1; Aurigene); avelumab (PD-L1; Merck); durvalumab (PD-L1; Medimmune).

In some embodiments of any of the aspects, an inhibitor of an immune checkpoint protein can be an antibody, antibody reagent, antigen-binding fragment thereof, or CAR that specifically binds to at least one immune checkpoint protein. Such inhibitors are known in the art. In some embodiments of any of the aspects, inhibitors of an immune checkpoint protein can be inhibitory nucleic acid molecules. In some embodiments of any of the aspects, an inhibitory nucleic acid molecule can be a miRNA, iRNA, amiRNA, RNAi molecule or the like.

In some embodiments of any of the aspects, an inhibitor of immune checkpoint proteins can be a natural ligand thereof and/or an inhibitor derived from a natural ligand, e.g., PD-L1 or B7.

In some embodiments of any of the aspects, multiple inhibitors of immune checkpoint protein(s) can be used in the methods and compositions described herein, e.g., two or more inhibitors that target the same immune checkpoint protein, or at least one inhibitor that targets a first immune checkpoint protein and at least one inhibitor that targets at least one additional immune checkpoint protein.

In some embodiments of any of the aspects, the a) inhibitor of CHI3L1, inhibitor of Sema7A, inhibitor of β1-integrin, or agonist of PlexinC1 and b) the inhibitor of an immune checkpoint protein are present in the same bivalent antibody reagent. In some embodiments of any of the aspects, the inhibitor of CHI3L1 and the inhibitor of an immune checkpoint protein are present in the same bivalent antibody reagent. In some embodiments of any of the aspects, the immune checkpoint protein targeted by such a bivalent antibody reagent is PD-1 or CTLA4.

As used herein, the term "bivalent antibody reagent" refers to an antibody reagent that comprises a first antigen-binding domain which has binding specificity for a first target, and a second antigen-binding domain which has binding specificity for a second target, i.e., the agent has specificity for two targets, e.g., CHI3L1 and PD-1, or CHI3L1 and CTLA4. The first target and the second target are not the same (i.e., are different targets (e.g., proteins)). In some embodiments of any of the aspects, the different targets can be co-expressed on the same cell. In some embodiments of any of the aspects, a bivalent antibody reagent polypeptide agent can bind targets present on a single cell (heterophilic binding in cis), and/or bind one target on one cell and the other on another cell (heterophilic binding in trans). In some embodiments of any of the aspects, a bivalent antibody reagent polypeptide agent can bind one or more soluble, extracellular targets. Bivalent antibody reagents comprising antigen-binding portions of antibodies specific for two different antigens can be readily constructed by one of skill in the art. Generally, sequences encoding the antigen-binding domain of a first antibody characterized and known to bind a desired epitope on one antigen can be joined, either directly, or through any of a variety of linkers as known to the ordinarily skilled artisan, to sequences encoding the antigen-binding domain of a second antibody characterized and known to bind a desired epitope on a second antigen. Such sequences can be inserted into an appropriate vector and introduced to a cell to produce the bivalent antibody polypeptide by methods known to those of ordinary skill in the art.

In some embodiments of any of the aspects, any of the antibodies, antigen-binding fragments thereof, or antibody reagents described herein can be antibody-drug conjugates. In particular embodiments, an antibody-drug conjugate comprises an antibody, antibody reagent, or antigen-binding portion thereof as described herein. The drug can be, e.g., a chemotherapeutic molecule as described elsewhere herein. In some embodiments of any of the aspects, the antibody-drug conjugate comprises a chemotherapeutic agent directly conjugated and/or bound to an antibody or antigen-binding portion thereof. In some embodiments of any of the aspects, binding can be non-covalent, e.g., by hydrogen bonding, electrostatic, or van der Waals interactions; however, binding may also be covalent. By "conjugated" is meant the covalent linkage of at least two molecules. In some embodiments of any of the aspects, the composition can be an antibody-drug conjugate.

In some embodiments of any of the aspects, an antibody, antibody reagent, or antigen-binding portion thereof can be bound to and/or conjugated to multiple chemotherapeutic molecules. In some embodiments of any of the aspects, an antibody-drug conjugate can be bound to and/or conjugated to multiple chemotherapeutic molecules. In some embodiments of any of the aspects, the ratio of a given chemotherapeutic molecule to an antibody or antigen-binding portion thereof can be from about 1:1 to about 1,000:1, e.g., a single antibody reagent molecule can be linked to, conjugated to, etc. from about 1 to about 1,000 individual chemotherapeutic molecules.

In some embodiments of any of the aspects, an antibody, or antigen-binding portion thereof, and the chemotherapeutic agent can be present in a scaffold material. Scaffold materials suitable for use in therapeutic compositions are known in the art and can include, but are not limited to, a nanoparticle; a matrix; a hydrogel; and a biomaterial, biocompatible, and/or biodegradable scaffold material. As used herein, the term "nanoparticle" refers to particles that are on the order of about $10^{-9}$ or one to several billionths of a meter. The term "nanoparticle" includes nanospheres; nanorods; nanoshells; and nanoprisms; these nanoparticles may be part of a nanonetwork.

The term "nanoparticles" also encompasses liposomes and lipid particles having the size of a nanoparticle. As used herein, the term "matrix" refers to a 3-dimensional structure comprising the components of a composition described herein (e.g., an antibody or antigen-binding portion thereof). Non-limiting examples of matrix structures include foams; hydrogels; electrospun fibers; gels; fiber mats; sponges; 3-dimensional scaffolds; non-woven mats; woven materials; knit materials; fiber bundles; and fibers and other material formats (See, e.g., Rockwood et al. Nature Protocols 2011 6:1612-1631 and US Patent Publications 2011/0167602; 2011/0009960; 2012/0296352; and U.S. Pat. No. 8,172,901; each of which is incorporated by reference herein in its entirety). The structure of the matrix can be selected by one of skill in the art depending upon the intended application of the composition, e.g., electrospun matrices can have greater surface area than foams.

In some embodiments of any of the aspects, the scaffold is a hydrogel. As used herein, the term "hydrogel" refers to a three-dimensional polymeric structure that is insoluble in water but which is capable of absorbing and retaining large quantities of water to form a stable, often soft and pliable, structure. In some embodiments of any of the aspects, water can penetrate in between the polymer chains of the polymer network, subsequently causing swelling and the formation of a hydrogel. In general, hydrogels are superabsorbent. Hydrogels have many desirable properties for biomedical applications. For example, they can be made nontoxic and compatible with tissue, and they are highly permeable to water, ions, and small molecules. Hydrogels are superabsorbent (they can contain over 99% water) and can be comprised of natural (e.g., silk) or synthetic polymers, e.g., PEG.

As used herein, "biomaterial" refers to a material that is biocompatible and biodegradable. As used herein, the term "biocompatible" refers to substances that are not toxic to cells. In some embodiments of any of the aspects, a substance is considered to be "biocompatible" if its addition to cells in vitro results in less than or equal to approximately 20% cell death. In some embodiments of any of the aspects, a substance is considered to be "biocompatible" if its addition to cells in vivo does not induce inflammation and/or other adverse effects in vivo. As used herein, the term "biodegradable" refers to substances that are degraded under physiological conditions. In some embodiments of any of the aspects, a biodegradable substance is a substance that is broken down by cellular machinery. In some embodiments of any of the aspects, a biodegradable substance is a substance that is broken down by chemical processes.

In one aspect of any of the embodiments, described herein is a composition comprising a) an inhibitor of an immune checkpoint protein and b) at least one of an inhibitor of CHI3L1, an inhibitor of β1-integrin, and inhibitor of Sema7A, and an agonist of Plexin C1. In one aspect of any of the embodiments, described herein is the combination of a composition comprising an inhibitor of an immune checkpoint protein and a composition comprising b) at least one of an inhibitor of CHI3L1, an inhibitor of β1-integrin, and inhibitor of Sema7A, and an agonist of Plexin C1 (e.g., combined into a single composition or prepared as separate compositions for use or packaging as a paired unit). In some embodiments of any of the aspects, the composition can comprise, one, two, three, or all of an inhibitor of CHI3L1, an inhibitor of β1-integrin, and inhibitor of Sema7A, and an agonist of Plexin C1.

In one aspect of any of the embodiments, described herein is a composition comprising an inhibitor of CHI3L1 and an inhibitor of an immune checkpoint protein. In one aspect of any of the embodiments, described herein is the combination of a composition comprising an inhibitor of CHI3L1 and a composition comprising an inhibitor of an immune checkpoint protein (e.g., combined into a single composition or prepared as separate compositions for use or packaging as a paired unit). In some embodiments of any of the aspects, the composition is a pharmaceutical composition. As used herein, the term "pharmaceutical composition" refers to the active agent in combination with a pharmaceutically acceptable carrier accepted for use in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The preparation of a pharmacological composition that contains active ingredients dissolved or dispersed therein is well understood in the art and need not be limited based on formulation. Typically, such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance or maintain the effectiveness of the active ingredient. The therapeutic composition as described herein can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the invention that will be effective in the treatment of a particular disorder or condition will depend on the nature of the disorder or condition, and can be determined by standard clinical techniques.

In some embodiments of any of the aspects, the composition as described herein can be a lyophilisate.

In some embodiments of any of the aspects, the technology described herein relates to a syringe or catheter, including an organ-specific catheter (e.g., renal catheter, biliary catheter, cardiac catheter, etc.), comprising a therapeutically effective amount of a composition described herein.

In one aspect, described herein is a kit comprising one or more compositions as described herein, e.g., a composition comprising an inhibitor of CHI3L1 and a composition comprising an inhibitor of an immune checkpoint protein; or a composition comprising both an inhibitor of CHI3L1 and composition comprising an inhibitor of an immune checkpoint protein. A kit is any manufacture (e.g., a package or container) comprising at least one reagent, e.g., an antibody, the manufacture being promoted, distributed, or sold as a unit for performing the methods described herein. In some embodiments of any of the aspects, the antibody, antibody reagent, antigen-binding fragment thereof as described herein is immobilized on a solid support. In some embodiments of any of the aspects, the solid support comprises a particle, a bead, a polymer, or a substrate. In some embodiments of any of the aspects, the antibody, antibody reagent or antigen-binding fragment thereof is detectably labeled.

The kits described herein can optionally comprise additional components useful for performing the methods described herein. By way of example, the kit can comprise fluids (e.g., buffers) suitable for composition the one or more reagents described herein, an instructional material which describes performance of a method as described herein, and the like. A kit can further comprise devices and/or reagents for delivery of the composition as described herein. Additionally, the kit may comprise an instruction leaflet and/or may provide information as to the relevance of the obtained results.

As used herein, the phrase "therapeutically effective amount", "effective amount" or "effective dose" refers to an amount that provides a therapeutic or aesthetic benefit in the treatment, prevention, or management of a tumor or malignancy, e.g., an amount that provides a statistically significant decrease in at least one symptom, sign, or marker of a tumor or malignancy. Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents In one aspect, the technology described herein relates to a method comprising administering a combination of agents described herein to a subject. In one aspect, the technology described herein relates to a method comprising administering an inhibitor of CHI3L1 and an inhibitor of an immune checkpoint protein to a subject. In some embodiments of any of the aspects, the subject is in need of treatment for a cancer and/or malignancy. In some embodiments of any of the aspects, the subject is in need of treatment for: prostate cancer, colon cancer, rectal cancer, ovarian cancer, kidney cancer, breast cancer, glioblastoma, melanoma, malignant melanoma, and lung cancer. In some embodiments of any of the aspects, the method is a method of treating a subject. In some embodiments of any of the aspects, the method is a method of treating a cancer in a subject.

As used herein, the term "cancer" relates generally to a class of diseases or conditions in which abnormal cells divide without control and can invade nearby tissues. Cancer cells can also spread to other parts of the body through the blood and lymph systems. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord.

In some embodiments of any of the aspects, the cancer is a primary cancer. In some embodiments of any of the aspects, the cancer is a malignant cancer. As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor.

As used herein, the term "benign" or "non-malignant" refers to tumors that may grow larger but do not spread to other parts of the body. Benign tumors are self-limited and typically do not invade or metastasize.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancer cells form tumors, but some, e.g., leukemia, do not necessarily form tumors. For those cancer cells that form tumors, the terms cancer (cell) and tumor (cell) are used interchangeably.

A subject that has a cancer or a tumor is a subject having objectively measurable cancer cells present in the subject's body. Included in this definition are malignant, actively proliferative cancers, as well as potentially dormant tumors or micrometastatses. Cancers which migrate from their original location and seed other vital organs can eventually lead to the death of the subject through the functional deterioration of the affected organs. Hemopoietic cancers, such as leukemia, are able to out-compete the normal hemopoietic compartments in a subject, thereby leading to hemopoietic failure (in the form of anemia, thrombocytopenia and neutropenia) ultimately causing death.

Examples of cancer include but are not limited to, carcinoma, lymphoma, blastoma, sarcoma, leukemia, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma (GBM); hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

A "cancer cell" is a cancerous, pre-cancerous, or transformed cell, either in vivo, ex vivo, or in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage independence, malignancy, loss of contact inhibition and density limitation of growth, growth factor or serum independence, tumor specific markers, invasiveness or metastasis, and tumor growth in suitable animal hosts such as nude mice.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patients or subjects include any subset of the foregoing, e.g., all of the above, but excluding one or more groups or species such as humans, primates or rodents. In certain embodiments, the subject is a mammal, e.g., a primate, e.g., a human. The terms, "patient", "individual" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used, for example, as subjects that represent animal models of, for example, various cancers. In addition, the methods described herein can be used to treat domesticated animals and/or pets. A subject can be male or female.

A subject can be one who has been previously diagnosed with or identified as suffering from or having a condition in need of treatment (e.g., a cancer) or one or more complications related to such a condition, and optionally, but need not have already undergone treatment for a condition or the one or more complications related to the condition. Alternatively, a subject can also be one who has not been previously diagnosed as having a condition in need of treatment or one or more complications related to such a condition. For example, a subject can be one who exhibits one or more risk factors for a condition or one or more complications related to a condition or a subject who does not exhibit risk factors. A "subject in need" of treatment for a particular condition can be a subject having that condition, diagnosed as having that condition, or at risk of developing that condition.

As used herein, the terms "treat," "treatment," "treating," or "amelioration" when used in reference to a disease, disorder or medical condition, refer to therapeutic treatments for a condition, wherein the object is to reverse, alleviate, ameliorate, inhibit, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a condition is reduced or halted. That is, "treatment" includes not just the improvement of symptoms or markers, but also a cessation or at least slowing of progress or worsening of symptoms that would be expected in the absence of treatment. Beneficial or desired clinical results include, but are not limited to, alleviation of one or more symptom(s), diminishment of extent of the deficit, stabilized (i.e., not worsening) state of a tumor or malignancy, delay or slowing of tumor growth and/or metastasis, and an increased lifespan as compared to that expected in the absence of treatment. As used herein, the term "administering," refers to the placement of an agent, including but not limited to, an antibody, antibody reagent, antigen-binding portion thereof, or CAR as described herein or a nucleic acid encoding an antibody, antibody reagent, antigen-binding portion thereof, or CAR, or a cell comprising such an agent, as described herein into a subject by a method or route which results in at least partial localization of the agents at a desired site. The pharmaceutical composition comprising an antibody, antibody reagent, antigen-binding portion thereof, or CAR as described herein or a nucleic acid encoding an antibody, antibody reagent, antigen-binding portion thereof, or CAR, or a cell comprising such an agent as described herein disclosed herein can be administered by any appropriate route which results in an effective treatment in the subject.

In some embodiments of any of the aspects, the methods described herein relate to CAR-T cell therapy. CAR-T cell and related therapies relate to adoptive cell transfer of immune cells (e.g., T cells) expressing a CAR that binds specifically to a targeted cell type (e.g., cancer cells) to treat a subject. In some embodiments of any of the aspects, the cells administered as part of the therapy can be autologous to the subject. In some embodiments of any of the aspects, the cells administered as part of the therapy are not autologous to the subject. In some embodiments of any of the aspects, the cells are engineered and/or genetically modified to express the CAR. Further discussion of CAR-T therapies can be found, e.g., in Maus et al. Blood 2014 123:2624-35; Reardon et al. Neuro-Oncology 2014 16:1441-1458; Hoyos et al. Haematologica 2012 97:1622; Byrd et al. J Clin Oncol 2014 32:3039-47; Maher et al. Cancer Res 2009 69:4559-4562; and Tamada et al. Clin Cancer Res 2012 18:6436-6445; each of which is incorporated by reference herein in its entirety.

The administration of the compositions contemplated herein may be carried out in any convenient manner, including by aerosol inhalation, injection, ingestion, transfusion, implantation or transplantation. In a preferred embodiment, compositions are administered parenterally. The phrases "parenteral administration" and "administered parenterally"

as used herein refers to modes of administration other than enteral and topical administration, usually by injection, and includes, without limitation, intravascular, intravenous, intramuscular, intraarterial, intrathecal, intracapsular, intraorbital, intratumoral, intracardiac, intradermal, intraperitoneal, transtracheal, subcutaneous, subcuticular, intraarticular, subcapsular, subarachnoid, intraspinal and intrasternal injection and infusion. In one embodiment, the compositions contemplated herein are administered to a subject by direct injection into a tumor, lymph node, or site of infection.

It can generally be stated that a pharmaceutical composition comprising the cells, e.g., T cells or immune cells, described herein may be administered at a dosage of $10^2$ to $10^{10}$ cells/kg body weight, preferably $10^5$ to $10^6$ cells/kg body weight, including all integer values within those ranges. The number of cells will depend upon the ultimate use for which the composition is intended as will the type of cells included therein. For uses provided herein, the cells are generally in a volume of a liter or less, can be 500 mLs or less, even 250 mLs or 100 mLs or less. Hence the density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells. In some aspects of the present invention, particularly since all the infused cells will be redirected to a particular target antigen, lower numbers of cells, in the range of $10^6$/kilogram ($10^6$-$10^{11}$ per patient) may be administered. CAR expressing cell compositions may be administered multiple times at dosages within these ranges. The cells may be allogeneic, syngeneic, xenogeneic, or autologous to the patient undergoing therapy. If desired, the treatment may also include administration of mitogens (e.g., PHA) or lymphokines, cytokines, and/or chemokines (e.g., IFN-γ, IL-2, IL-12, TNF-alpha, IL-18, and TNF-beta, GM-CSF, IL-4, IL-13, Flt3-L, RANTES, MIP1α, etc.) as described herein to enhance induction of the immune response. In some embodiments of any of the aspects, the dosage can be from about $1\times10^5$ cells to about $1\times10^8$ cells per kg of body weight. In some embodiments of any of the aspects, the dosage can be from about $1\times10^6$ cells to about $1\times10^7$ cells per kg of body weight. In some embodiments of any of the aspects, the dosage can be about $1\times10^6$ cells per kg of body weight. In some embodiments of any of the aspects, one dose of cells can be administered. In some embodiments of any of the aspects, the dose of cells can be repeated, e.g., once, twice, or more. In some embodiments of any of the aspects, the dose of cells can be administered on, e.g., a daily, weekly, or monthly basis.

The dosage ranges for the agent depend upon the potency, and encompass amounts large enough to produce the desired effect e.g., slowing of tumor growth or a reduction in tumor size. The dosage should not be so large as to cause unacceptable adverse side effects. Generally, the dosage will vary with the age, condition, and sex of the patient and can be determined by one of skill in the art. The dosage can also be adjusted by the individual physician in the event of any complication. In some embodiments of any of the aspects, the dosage ranges from 0.001 mg/kg body weight to 0.5 mg/kg body weight. In some embodiments of any of the aspects, the dose range is from 5 μg/kg body weight to 100 μg/kg body weight. Alternatively, the dose range can be titrated to maintain serum levels between 1 μg/mL and 1000 μg/mL. For systemic administration, subjects can be administered a therapeutic amount, such as, e.g., 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

Administration of the doses recited above can be repeated. In some embodiments of any of the aspects, the doses are given once a day, or multiple times a day, for example but not limited to three times a day. In some embodiments, the doses recited above are administered daily for several weeks or months. The duration of treatment depends upon the subject's clinical progress and responsiveness to therapy.

In some embodiments of any of the aspects, the dose can be from about 2 mg/kg to about 15 mg/kg. In some embodiments of any of the aspects, the dose can be about 2 mg/kg. In some embodiments of any of the aspects, the dose can be about 4 mg/kg. In some embodiments of any of the aspects, the dose can be about 5 mg/kg. In some embodiments of any of the aspects, the dose can be about 6 mg/kg. In some embodiments of any of the aspects, the dose can be about 8 mg/kg. In some embodiments of any of the aspects, the dose can be about 10 mg/kg. In some embodiments of any of the aspects, the dose can be about 15 mg/kg. In some embodiments of any of the aspects, the dose can be from about 100 mg/m$^2$ to about 700 mg/m$^2$. In some embodiments of any of the aspects, the dose can be about 250 mg/m$^2$. In some embodiments of any of the aspects, the dose can be about 375 mg/m$^2$. In some embodiments of any of the aspects, the dose can be about 400 mg/m$^2$. In some embodiments of any of the aspects, the dose can be about 500 mg/m$^2$.

In some embodiments of any of the aspects, the dose can be administered intravenously. In some embodiments of any of the aspects, the intravenous administration can be an infusion occurring over a period of from about 10 minute to about 3 hours. In some embodiments of any of the aspects, the intravenous administration can be an infusion occurring over a period of from about 30 minutes to about 90 minutes.

In some embodiments the dose can be administered about weekly. In some embodiments of any of the aspects, the dose can be administered weekly. In some embodiments of any of the aspects, the dose can be administered weekly for from about 12 weeks to about 18 weeks. In some embodiments the dose can be administered about every 2 weeks. In some embodiments the dose can be administered about every 3 weeks. In some embodiments of any of the aspects, the dose can be from about 2 mg/kg to about 15 mg/kg administered about every 2 weeks. In some embodiments of any of the aspects, the dose can be from about 2 mg/kg to about 15 mg/kg administered about every 3 weeks. In some embodiments of any of the aspects, the dose can be from about 2 mg/kg to about 15 mg/kg administered intravenously about every 2 weeks. In some embodiments of any of the aspects, the dose can be from about 2 mg/kg to about 15 mg/kg administered intravenously about every 3 weeks. In some embodiments of any of the aspects, the dose can be from about 200 mg/m$^2$ to about 400 mg/m$^2$ administered intravenously about every week. In some embodiments of any of the aspects, the dose can be from about 200 mg/m$^2$ to about 400 mg/m$^2$ administered intravenously about every 2 weeks. In some embodiments of any of the aspects, the dose can be from about 200 mg/m$^2$ to about 400 mg/m$^2$ administered intravenously about every 3 weeks. In some embodiments of any of the aspects, a total of from about 2 to about 10 doses are administered. In some embodiments of any of the aspects, a total of 4 doses are administered. In some embodiments of any of the aspects, a total of 5 doses are administered. In some embodiments of any of the aspects, a total of 6 doses are administered. In some embodiments of any of the aspects, a total of 7 doses are administered. In some embodiments of any of the aspects, a total of 8 doses are administered. In some embodiments of any of the aspects, the administration occurs for a total of from about 4 weeks to about 12 weeks. In some embodiments of any of the aspects, the administration occurs for a total of about 6 weeks. In some embodiments of any of the aspects, the administration occurs for a total of about 8 weeks. In some embodiments of any of the aspects, the administration occurs for a total of about 12 weeks. In some embodiments of any of the aspects, the initial dose can be from about 1.5 to about 2.5 fold greater than subsequent doses.

In some embodiments of any of the aspects, the dose can be from about 1 mg to about 2000 mg. In some embodiments of any of the aspects, the dose can be about 3 mg. In some embodiments of any of the aspects, the dose can be about 10 mg. In some embodiments of any of the aspects, the dose can be about 30 mg. In some embodiments of any of the aspects, the dose can be about 1000 mg. In some embodiments of any of the aspects, the dose can be about 2000 mg. In some embodiments of any of the aspects, the dose can be about 3 mg given by intravenous infusion daily. In some embodiments of any of the aspects, the dose can be about 10 mg given by intravenous infusion daily. In some embodiments of any of the aspects, the dose can be about 30 mg given by intravenous infusion three times per week.

A therapeutically effective amount is an amount of an agent that is sufficient to produce a statistically significant, measurable change in tumor size, tumor growth etc. (efficacy measurements are described below herein). Such effective amounts can be gauged in clinical trials as well as animal studies.

An agent can be administered intravenously by injection or by gradual infusion over time. Given an appropriate formulation for a given route, for example, agents useful in the methods and compositions described herein can be administered intravenously, intranasally, by inhalation, intraperitoneally, intramuscularly, subcutaneously, intracavity, and can be delivered by peristaltic means, if desired, or by other means known by those skilled in the art. It is preferred that the compounds used herein are administered orally, intravenously or intramuscularly to a patient having cancer. Local administration directly to a tumor mass is also specifically contemplated.

Therapeutic compositions containing at least one agent can be conventionally administered in a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired.

Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

The multiple agents of the combinations described herein can be administered concurrently or sequentially. The multiple agents of the combinations described herein can be administered in the same or separate formulations. The multiple agents of the combinations described herein can be administered by the same or different routes of administration. In some embodiments of any of the aspects, multiple agents of the combinations described herein can be administered on the same day, within 2 days of each other, within 3 days of each other, within 4 days of each other, within 5 days of each other, within 6 days of each other, or within 7 days of each other. In some embodiments of any of the aspects, for any pair-wise combination of agents, the second-administered agent is administered during the period in which the first-administered agent or its consequences are still detectable in the subject.

The inhibitor of CHI3L1 and the inhibitor of an immune checkpoint protein can be administered concurrently or sequentially. The inhibitor of CHI3L1 and the inhibitor of an immune checkpoint protein can be administered in the same or separate formulations. The inhibitor of CHI3L1 and the inhibitor of an immune checkpoint protein can be administered by the same or different routes of administration. In some embodiments of any of the aspects, the inhibitor of CHI3L1 and the inhibitor of an immune checkpoint protein can be administered on the same day, within 2 days of each other, within 3 days of each other, within 4 days of each other, within 5 days of each other, within 6 days of each other, or within 7 days of each other. In some embodiments of any of the aspects the second-administered agent is administered during the period in which the first-administered agent is still detectable in the subject.

In some embodiments of any of the aspects, the methods further comprise administering the pharmaceutical composition(s) described herein along with one or more additional chemotherapeutic agents, biologics, drugs, or treatments as part of a combinatorial therapy. In some such embodiments, the chemotherapeutic agent biologic, drug, or treatment is selected from the group consisting of: radiation therapy, surgery, antibody reagents, and/or small molecules.

In some embodiments of the methods described herein, the methods further comprise administering one or more chemotherapeutic agents to the subject being administered the pharmaceutical composition described herein. Non-limiting examples of chemotherapeutic agents can include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaII; dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any one of the above.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins, such as small molecule toxins or enzymatically active toxins of bacterial, fungal, plant or animal origin, including fragments and/or variants thereof.

As used herein, the terms "chemotherapy" or "chemotherapeutic agent" refer to any chemical agent with therapeutic usefulness in the treatment of diseases characterized by abnormal cell growth. Such diseases include tumors, neoplasms and cancer as well as diseases characterized by hyperplastic growth. Chemotherapeutic agents as used herein encompass both chemical and biological agents. These agents function to inhibit a cellular activity upon which the cancer cell depends for continued survival. Categories of chemotherapeutic agents include alkylating/alkaloid agents, antimetabolites, hormones or hormone analogs, and miscellaneous antineoplastic drugs. Most if not all of these agents are directly toxic to cancer cells and do not require immune stimulation. In one embodiment, a chemotherapeutic agent is an agent of use in treating neoplasms such as solid tumors. In one embodiment, a chemotherapeutic agent is a radioactive molecule. One of skill in the art can readily identify a chemotherapeutic agent of use (e.g., see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology $2^{nd}$ Edition, 2000 Churchill Livingstone, Inc; Baltzer L, Berkery R (eds)). The bispecific and multispecific polypeptide agents described herein can be used in conjunction with additional chemotherapeutic agents.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one time administration and typical dosages range from 10 to 200 units (Grays) per day.

In some embodiments of any of the aspects, the methods described herein can further comprise administering an additional immunotherapy to the subject. As used herein, "immunotherapy" refers to a diverse set of therapeutic strategies designed to induce the patient's own immune system to fight the tumor, and include, but are not limited to, intravesical BCG immunotherapy for superficial bladder cancer, vaccines to generate specific immune responses, such as for malignant melanoma and renal cell carcinoma, the use of Sipuleucel-T for prostate cancer, in which dendritic cells from the patient are loaded with prostatic acid phosphatase peptides to induce a specific immune response against prostate-derived cells, administration of cytokines, growth factors and/or signaling molecules that stimulate one or more immune cell type (e.g., interleukins), ex vivo expansion and/or stimulation of lymphocytes and/or dendritic cell specific for a tumor antigen prior to reintroduction to the patient, imiquimod, adoptive cell transfer, and/or the methods described, e.g., in International Patent Publication WO 2003/063792 and U.S. Pat. No. 8,329,660. In some embodiments of any of the aspects, the immunotherapy stimulates NK responses. In some embodiments of any of the aspects, the immunotherapy is an adoptive cell transfer approach, i.e., adoptive immunotherapy.

In some embodiments of any of the aspects, the methods described herein can further comprise administering an additional antibody, antibody reagent, antigen-binding portion thereof, or T cell comprising a CAR to the subject. In some embodiments of any of the aspects, the methods described herein can further comprise administering cytokine to the subject. Antibody- and cytokine-based therapies are known in the art and can include, by way of non-limiting example, alemtuzumab; bevacizumab; brentuximab vedotin; cetuximab; gemtuzumab; ibritumomab tiuxetan; ipilimumab; ofatumumab; pantibumumab; rituximab; tositumomab; trastuzumab; interleukin-2, and interferon-alpha.

The efficacy of a given treatment for, e.g., cancer, can be determined by the skilled clinician. However, a treatment is considered "effective treatment," as the term is used herein, if any one or all of the signs or symptoms of e.g., a tumor are altered in a beneficial manner or other clinically accepted symptoms are improved, or even ameliorated, e.g., by at least 10% following treatment with an agent as described herein. Efficacy can also be measured by a failure of an individual to worsen as assessed by hospitalization or need for medical interventions (i.e., progression of the disease is halted). Methods of measuring these indicators are known to those of skill in the art and/or described herein.

An effective amount for the treatment of a disease means that amount which, when administered to a mammal in need thereof, is sufficient to result in effective treatment as that term is defined herein, for that disease. Efficacy of an agent can be determined by assessing physical indicators of, for example cancer, e.g., tumor size, tumor mass, tumor density, angiogenesis, tumor growth rate, etc.

In some embodiments of any of the aspects described herein, a subject administered a composition described herein can be a subject determined to have an elevated level of CHI3L1 or a level of CHI3L1 that is increased compared to a prior assessment of the level in that subject. In some embodiments of any of the aspects, the elevated level of CHI3L1 is the level of circulating CHI3L1. In some embodiments of any of the aspects described herein, a subject administered a composition described herein can be a subject determined to have cancer cells which are CHI3L1+.

In some embodiments of any of the aspects described herein, the method comprising administering a composition as described herein can further comprise a first step of identifying a subject having an elevated level of CHI3L1. In some embodiments of any of the aspects, the elevated level of CHI3L1 is the level of circulating CHI3L1. In some embodiments of any of the aspects described herein, the method comprising administering a composition as described herein can further comprise a first step of identifying a subject having cancer cells which are CHI3L1+.

As used herein, a "CHI3L1+" cell is a cell expressing an increased level of CHI3L1+, e.g., as compared to a healthy cell of the same type or an average level of CHI3L1 found in healthy cells of the same type. In some embodiments of any of the aspects, an increased level of CHI3L1 can be a level which is at least 1.5× the level found in a reference, e.g., 1.5×, 2×, 3×, 4×, 5× or greater than the reference level.

In some embodiments of any of the aspects, the expression level of CHI3L1 can be measured by determining the level of an expression product of the CHI3L1 gene, e.g., a CHI3L1 RNA transcript or a CHI3L1 polypeptide. Such molecules can be isolated, derived, or amplified from a biological sample, such as a biofluid. In some embodiments of any of the aspects, a detectable signal is generated by the antibody or antigen-binding portion thereof when a CHI3L1 molecule is present. In some embodiments of any of the aspects, the antibody or antigen-binding portion thereof is detectably labeled or capable of generating a detectable signal. In some embodiments of any of the aspects, the level of the CHI3L1 is determined using a method selected from the group consisting of: Western blot; immunoprecipitation; enzyme-linked immunosorbent assay (ELISA); radioimmunological assay (RIA); sandwich assay; fluorescence in situ hybridization (FISH); immunohistological staining; radio-immunometric assay; immunofluoresence assay; mass spectroscopy; FACS; and immunoelectrophoresis assay. In some embodiments of any of the aspects, the antibody or antigen-binding portion thereof is detectably labeled or generates a detectable signal. In some embodiments of any of the aspects, the expression level of CHI3L1 is normalized relative to the expression level of one or more reference genes or reference proteins. In some embodiments of any of the aspects, the reference level of CHI3L1 is the expression level of CHI3L1 in a prior sample obtained from the subject.

In some embodiments of any of the aspects, the level of CHI3L1 can be the level of CHI3L1 polypeptide. Detection of CHI3L1 polypeptides can be according to any method known in the art. Immunological methods to detect CHI3L1 polypeptides in accordance with the present technology include, but are not limited to antibody techniques such as immunohistochemistry, immunocytochemistry, flow cytometry, fluorescence-activated cell sorting (FACS), immunoblotting, radioimmunoassays, western blotting, immunoprecipitation, enzyme-linked immunosorbant assays (ELISA), and derivative techniques that make use of antibody reagents as described herein.

Immunochemical methods require the use of an antibody reagent specific for the target molecule (e.g., the antigen or in the embodiments described herein, a CHI3L1 polypeptide. In some embodiments of any of the aspects, the assays, methods, and/or systems described herein can comprise: an anti-CHI3L1 antibody reagent. In some embodiments of any of the aspects, the antibody reagent can be detectably labeled. In some embodiments of any of the aspects, the antibody reagent can be attached to a solid support (e.g., bound to a solid support). In some embodiments of any of the aspects, the solid support can comprise a particle (including, but not limited to an agarose or latex bead or particle or a magnetic particle), a bead, a nanoparticle, a polymer, a substrate, a slide, a coverslip, a plate, a dish, a well, a membrane, and/or a grating. The solid support can include many different materials including, but not limited to, polymers, plastics, resins, polysaccharides, silicon or silica based materials, carbon, metals, inorganic glasses, and membranes.

In one embodiment, an assay, method, and/or system as described herein can comprise an ELISA. In an exemplary embodiment, a first antibody reagent can be immobilized on a solid support (usually a polystyrene micro titer plate). The solid support can be contacted with a sample obtained from a subject, and the antibody reagent will bind ("capture") antigens for which it is specific (e.g., CHI3L1). The solid support can then be contacted with a second labeled antibody reagent (e.g., a detection antibody reagent). The detection antibody reagent can, e.g., comprise a detectable signal, be covalently linked to an enzyme, or can itself be detected by a secondary antibody which is linked to an enzyme through bio-conjugation. The presence of a signal indicates that both the first antibody reagent immobilized on the support and the second "detection" antibody reagent have bound to an antigen, i.e., the presence of a signal indicated the presence of a CHI3L1 molecule. Between each step the plate is typically washed with a mild detergent solution to remove any proteins or antibodies that are not specifically bound. After the final wash step the plate is developed by adding an enzymatic substrate to produce a visible signal, which indicates the quantity of CHI3L1 polypeptides in the sample. Older ELISAs utilize chromogenic substrates, though newer assays employ fluorogenic substrates with much higher sensitivity. There are other different forms of ELISA, which are well known to those skilled in the art.

In one embodiment, the assays, systems, and methods described herein can comprise a lateral flow immunoassay test (LFIA), also known as the immunochromatographic assay, or strip test to measure or determine the level of CHI3L1 polypeptide in a sample. LFIAs are a simple device intended to detect the presence (or absence) of CHI3L1 in a sample. There are currently many LFIA tests used for medical diagnostics either for home testing, point of care testing, or laboratory use. LFIA tests are a form of immunoassay in which the test sample flows along a solid substrate via capillary action. After the sample is applied to the test strip it encounters a colored antibody reagent which mixes with the sample, and if bound to a portion of the sample, transits the substrate encountering lines or zones which have been pretreated with a second antibody reagent. Depending upon the level of CHI3L1 present in the sample the colored antibody reagent can become bound at the test line or zone. LFIAs are essentially immunoassays adapted to operate along a single axis to suit the test strip format or a dipstick format. Strip tests are extremely versatile and can be easily modified by one skilled in the art for detecting an enormous range of antigens from fluid samples such as urine, blood, water samples etc. Strip tests are also known as dip stick test, the name bearing from the literal action of "dipping" the test strip into a fluid sample to be tested. LFIA strip test are easy to use, require minimum training and can easily be included as components of point-of-care test (POCT) diagnostics to be used on site in the field. LFIA tests can be operated as either competitive or sandwich assays. Sandwich LFIAs are similar to sandwich ELISA. The sample first encounters colored particles which are labeled with antibody reagents specific for a target (e.g., a CHI3L1-specific antibody reagent). The test line will also contain antibody reagents (e.g., a CHI3L1-specific antibody reagent). The test line will show as a colored band in positive samples. In some embodiments of any of the aspects, the lateral flow immunoassay can be a double antibody sandwich assay, a competitive assay, a quantitative assay or variations thereof. There are a number of variations on lateral flow technology. It is also possible to apply multiple capture zones to create a multiplex test.

A typical test strip consists of the following components: (1) sample application area comprising an absorbent pad (i. e. the matrix or material) onto which the test sample is applied; (2) conjugate or reagent pad—this contains antibody reagent(s) specific to the target which can be conjugated to colored particles (usually colloidal gold particles, or latex microspheres); (3) test results area comprising a reaction membrane—typically a hydrophobic nitrocellulose or cellulose acetate membrane onto which antibody reagents are immobilized in a line across the membrane as a capture zone or test line (a control zone may also be present, containing antibodies specific for the antibody reagents conjugated to the particles or microspheres); and (4) optional wick or waste reservoir—a further absorbent pad designed to draw the sample across the reaction membrane by capillary action and collect it. The components of the strip are usually fixed to an inert backing material and may be presented in a simple dipstick format or within a plastic casing with a sample port and reaction window showing the capture and control zones. While not strictly necessary, most tests will incorporate a second line which contains an antibody that picks up free latex/gold in order to confirm the test has operated correctly.

The use of "dip sticks" or LFIA test strips and other solid supports has been described in the art in the context of an immunoassay for a number of antigen biomarkers. U.S. Pat. Nos. 4,943,522; 6,485,982; 6,187,598; 5,770,460; 5,622,871; 6,565,808, U.S. patent application Ser. No. 10/278,676; U.S. Ser. No. 09/579,673 and U.S. Ser. No. 10/717,082, which are incorporated herein by reference in their entirety, are non-limiting examples of such lateral flow test devices. Three U.S. patents (U.S. Pat. No. 4,444,880, issued to H. Tom; U.S. Pat. No. 4,305,924, issued to R. N. Piasio; and U.S. Pat. No. 4,135,884, issued to J. T. Shen) describe the use of "dip stick" technology to detect soluble antigens via immunochemical assays. The apparatuses and methods of these three patents broadly describe a first component fixed to a solid surface on a "dip stick" which is exposed to a solution containing a soluble antigen that binds to the component fixed upon the "dip stick," prior to detection of the component-antigen complex upon the stick. It is within the skill of one in the art to modify the teaching of these "dip stick" technologies as necessary for the detection of CHI3L1 polypeptides. In some embodiments of any of the aspects, the dip stick (or LFIA) can be suitable for use with urine samples. In some embodiments of any of the aspects, a dip stick can be suitable for use with blood samples.

Immunochemistry is a family of techniques based on the use of a specific antibody, wherein antibodies are used to specifically target molecules inside or on the surface of cells. In some embodiments of any of the aspects, immunohistochemistry ("IHC") and immunocytochemistry ("ICC") techniques can be used to detect or measure the levels of CHI3L1 polypeptide. IHC is the application of immunochemistry to tissue sections, whereas ICC is the application of immunochemistry to cells or tissue imprints after they have undergone specific cytological preparations such as, for example, liquid-based preparations. In some instances, signal amplification may be integrated into the particular protocol, wherein a secondary antibody, that includes a label, follows the application of an antibody reagent specific for platelets or leukocytes. Typically, for immunohistochemistry, tissue obtained from a subject and fixed by a suitable fixing agent such as alcohol, acetone, and paraformaldehyde, is sectioned and reacted with an antibody. Conventional methods for immunohistochemistry are described in Buchwalow and Bocker (Eds) "Immunohistochemistry: Basics and Methods" Springer (2010): Lin and Prichard "Handbook of Practical Immunohistochemistry" Springer (2011); which are incorporated by reference herein in their entireties. In some embodiments of any of the aspects, immunocytochemistry may be utilized where, in general, tissue or cells obtained from a subject are fixed by a suitable fixing agent such as alcohol, acetone, and paraformaldehyde, to which is reacted an antibody. Methods of immunocytological staining of human samples is known to those of skill in the art and described, for example, in Burry "Immunocytochemistry: A Practical Guide for Biomedical Research" Springer (2009); which is incorporated by reference herein in its entirety.

In some embodiments of any of the aspects, one or more of the antibody reagents described herein can comprise a detectable label and/or comprise the ability to generate a detectable signal (e.g., by catalyzing a reaction converting a compound to a detectable product). Detectable labels can comprise, for example, a light-absorbing dye, a fluorescent dye, or a radioactive label. Detectable labels, methods of detecting them, and methods of incorporating them into an antibody reagent are well known in the art.

In some embodiments of any of the aspects, detectable labels can include labels that can be detected by spectroscopic, photochemical, biochemical, immunochemical, electromagnetic, radiochemical, or chemical means, such as fluorescence, chemifluoresence, or chemiluminescence, or any other appropriate means. The detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies). The detectable label can be linked by covalent or non-covalent means to the antibody reagent. Alternatively, a detectable label can be linked such as by directly labeling a molecule that achieves binding to the antibody reagent via a ligand-receptor binding pair arrangement or other such specific recognition molecules. Detectable labels can include, but are not limited to radioisotopes, bioluminescent compounds, chromophores, antibodies, chemiluminescent compounds, fluorescent compounds, metal chelates, and enzymes.

In other embodiments, the detection antibody is labeled with a fluorescent compound. When the fluorescently labeled antibody is exposed to light of the proper wavelength, its presence can then be detected due to fluorescence. In some embodiments of any of the aspects, a detectable label can be a fluorescent dye molecule, or fluorophore including, but not limited to fluorescein, phycoerythrin, phycocyanin, o-phthaldehyde, fluorescamine, Cy3™, Cy5™, allophycocyanine, Texas Red, peridenin chlorophyll, cyanine, tandem conjugates such as phycoerythrin-Cy5™, green fluorescent protein, rhodamine, fluorescein isothiocyanate (FITC) and Oregon Green™, rhodamine and derivatives (e.g., Texas red and tetrarhodimine isothiocynate (TRITC)), biotin, phycoerythrin, AMCA, CyDyes™, 6-carboxyfhiorescein (commonly known by the abbreviations FAM and F), 6-carboxy-2',4',7',4,7-hexachlorofiuorescein (HEX), 6-carboxy-4',5'-dichloro-2',7'-dimethoxyfiuorescein (JOE or J), N,N,N',N'-tetramethyl-6carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g., Cy3, Cy5 and Cy7 dyes; coumarins, e.g umbelliferone; benzimide dyes, e.g., Hoechst 33258; phenanthridine dyes, e.g., Texas Red; ethidium dyes; acridine dyes; carbazole dyes; phenoxazine dyes; porphyrin dyes; polymethine dyes, e.g., cyanine dyes such as Cy3, Cy5, etc; BODIPY dyes and quinoline dyes.

In some embodiments of any of the aspects, a detectable label can be a radiolabel including, but not limited to $^3$H, $^{125}$I, $^{35}$S, $^{14}$C, $^{32}$P, and $^{33}$P.

In some embodiments of any of the aspects, a detectable label can be an enzyme including, but not limited to horseradish peroxidase and alkaline phosphatase. An enzymatic label can produce, for example, a chemiluminescent signal, a color signal, or a fluorescent signal. Enzymes contemplated for use to detectably label an antibody reagent include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase.

In some embodiments of any of the aspects, a detectable label is a chemiluminescent label, including, but not limited to lucigenin, luminol, luciferin, isoluminol, theromatic acridinium ester, imidazole, acridinium salt and oxalate ester.

In some embodiments of any of the aspects, a detectable label can be a spectral colorimetric label including, but not limited to colloidal gold or colored glass or plastic (e.g., polystyrene, polypropylene, and latex) beads.

In some embodiments of any of the aspects, antibodies can also be labeled with a detectable tag, such as c-Myc, HA, VSV-G, HSV, FLAG, V5, HIS, or biotin. Other detection systems can also be used, for example, a biotin-streptavidin system. In this system, the antibodies immunoreactive (i. e. specific for) with the biomarker of interest is biotinylated. Quantity of biotinylated antibody bound to the biomarker is determined using a streptavidin-peroxidase conjugate and a chromagenic substrate. Such streptavidin peroxidase detection kits are commercially available, e. g. from DAKO; Carpinteria, Calif.

An antibody reagent can also be detectably labeled using fluorescence emitting metals such as $^{152}$Eu, or others of the lanthanide series. These metals can be attached to the antibody reagent using such metal chelating groups as diethylenetriaminepentaacetic acid (DTPA) or ethylenediaminetetraacetic acid (EDTA).

The methods as described herein can relate to determining if a subject has an increased level of CHI3L1 relative to a reference level. In some embodiments of any of the aspects, the reference level of CHI3L1 can be the level of CHI3L1 in a healthy subject not having, or not diagnosed as having, e.g., cancer. In some embodiments of any of the aspects, the reference level can be the level in a sample of similar cell type, sample type, sample processing, and/or obtained from a subject of similar age, sex and other demographic parameters as the sample/subject for which the level of CHI3L1 is to be determined. In some embodiments of any of the aspects, the test sample and control reference sample are of the same type, that is, obtained from the same biological source, and comprising the same composition, e.g., the same number and type of cells and/or type of sample material. Accordingly, In some embodiments of any of the aspects, the level of CHI3L1 which is increased can vary as demographic factors such as age, gender, genotype, environmental factors, and individual medical histories vary. In some embodiments of any of the aspects, the reference level can comprise the level of CHI3L1 (e.g., CHI3L1 polypeptide) in a sample of the same type taken from a subject not exhibiting any signs or symptoms of, e.g., cancer. In some embodiments of any of the aspects, the reference expression level of CHI3L1 can be the expression level of CHI3L1 in a prior sample obtained from the subject. This permits a direct analysis of any change in levels in that individual.

In some embodiments of any of the aspects, a level of CHI3L1 can be increased relative to a reference level if the level of CHI3L1 is at least 1.25× the reference level, e.g., at least 1.25×, at least 1.5×, at least 2×, at least 3×, at least 4×, at least 5×, at least 6×, or greater of the reference level. In some embodiments of any of the aspects, the expression level of CHI3L1 can be normalized relative to the expression level of one or more reference genes or reference proteins. In some embodiments of any of the aspects, the expression level of CHI3L1 can be normalized relative to a reference value.

In some embodiments of any of the aspects, the expression level of no more than 20 other genes is determined. In some embodiments of any of the aspects, the expression level of no more than 10 other genes is determined.

The term "sample" or "test sample" as used herein denotes a sample taken or isolated from an organism, e.g., a urine sample from a subject. Exemplary biological samples include, but are not limited to, a biofluid sample; serum; plasma; urine; saliva; and/or tumor sample, etc. The term also includes a mixture of the above-mentioned samples. The term "test sample" also includes untreated or pretreated (or pre-processed) biological samples. In some embodiments of any of the aspects, a test sample can comprise cells from a subject. As used herein, the term "biofluid" refers to any fluid obtained from a biological source and includes, but is not limited to, blood, urine, and bodily secretions.

The test sample can be obtained by removing a sample from a subject, but can also be accomplished by using a previously isolated sample (e.g., isolated at a prior timepoint and isolated by the same or another person). In addition, the test sample can be freshly collected or a previously collected sample.

In some embodiments of any of the aspects, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments of any of the aspects, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments of any of the aspects, the test sample is a clarified test sample, for example, prepared by centrifugation and collection of a supernatant comprising the clarified test sample. In some embodiments of any of the aspects, a test sample can be a pre-processed test sample, for example, supernatant or filtrate resulting from a treatment selected from the group consisting of centrifugation, filtration, thawing, purification, and any combinations thereof. In some embodiments of any of the aspects, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for determination of the level of CHI3L1 as described herein.

In some embodiments of any of the aspects, the methods, assays, and systems described herein can further comprise a step of obtaining a test sample from a subject. In some embodiments of any of the aspects, the subject can be a human subject.

In some embodiments of any of the aspects, the methods, assays, and systems described herein can comprise creating a report based on the level of CHI3L1. In some embodiments of any of the aspects, the report denotes raw values for CHI3L1 in the test sample (plus, optionally, the level of CHI3L1 in a reference sample) or it indicates a percentage or fold increase in CHI3L1 as compared to a reference level, and/or provides a signal that the subject is at risk of having, or not having cancer.

As used herein "at risk of having" refers to at least a 2-fold greater likelihood of having a particular condition as compared to a subject that did not have an elevated and/or increased level of CHI3L1, e.g., a 2-fold, or 2.5-fold, or 3-fold, or 4-fold, or greater risk.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

The terms "decrease", "reduced", "reduction", or "inhibit" are all used herein to mean a decrease by a statistically significant amount. In some embodiments of any of the aspects, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments of any of the aspects, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function.

"Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

In some embodiments of any of the aspects, the polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to the assays described below herein. A functional fragment can comprise conservative substitutions of the sequences disclosed herein.

In some embodiments of any of the aspects, the polypeptide described herein can be a variant of a sequence described herein. In some embodiments of any of the aspects, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are known in the art and can be applied by the ordinarily skilled artisan.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA or cDNA. Suitable RNA can include, e.g., mRNA. In some embodiments of any of the aspects, the nucleic acid can be a cDNA, e.g., a nucleic acid lacking introns.

Nucleic acid molecules encoding amino acid sequence variants of antibodies or other polypeptides described herein are prepared by a variety of methods known in the art. These methods include, but are not limited to preparation by oligonucleotide-mediated (or site-directed) mutagenesis, PCR mutagenesis, and cassette mutagenesis of an earlier prepared variant or a non-variant version of the antibody. A nucleic acid sequence encoding at least one antibody, portion or polypeptide as described herein can be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations can be used to construct nucleic acid sequences which encode, e.g., a monoclonal antibody molecule, antibody reagent, antigen binding region thereof, or CAR.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as peptides or antibody portions in recoverable amounts. The precise nature of the regulatory regions needed for gene expression may vary from organism to organism, as is well known in the analogous art.

In some embodiments of any of the aspects, a nucleic acid encoding, e.g., an antibody, antibody reagent, antigen-binding portion thereof, CAR, ligand, or inhibitory nucleic acid as described herein, is comprised by a vector. In some of the aspects described herein, a nucleic acid sequence encoding a polypeptide or nucleic acid as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g., 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain the nucleic acid encoding a polypeptide or nucleic acid as described herein in place of non-essential viral genes. The vector and/or particle may be utilized for the purpose of transferring any nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, In some embodiments of any of the aspects, be combined with other suitable compositions and therapies. In some embodiments of any of the aspects, the vector is episomal. The use of a suitable episomal vector provides a means of maintaining the nucleotide of interest in the subject in high copy number extra chromosomal DNA thereby eliminating potential effects of chromosomal integration.

In one aspect of any of the embodiments, described herein is a cell comprising a polypeptide or nucleic acid as described herein, or a nucleic acid encoding such a polypeptide or nucleic acid.

The expression of a polypeptide or nucleci acid as described herein can occur in either prokaryotic or eukaryotic cells. Suitable hosts include bacterial or eukaryotic hosts, including yeast, insects, fungi, bird and mammalian cells either in vivo, or in situ, or host cells of mammalian, insect, bird or yeast origin. The mammalian cell or tissue can be of human, primate, hamster, rabbit, rodent, cow, pig, sheep, horse, goat, dog or cat origin, but any other mammalian cell may be used. Further, by use of, for example, the yeast ubiquitin hydrolase system, in vivo synthesis of ubiquitin-transmembrane polypeptide fusion proteins can be accomplished. The fusion proteins so produced can be processed in vivo or purified and processed in vitro, allowing synthesis of an antibody or portion thereof as described herein with a specified amino terminus sequence. Moreover, problems associated with retention of initiation codon-derived methionine residues in direct yeast (or bacterial) expression maybe avoided. Any of a series of yeast gene expression systems incorporating promoter and termination elements from the actively expressed genes coding for glycolytic enzymes produced in large quantities when yeast are grown in mediums rich in glucose can be utilized to obtain recombinant antibodies or antigen-binding portions thereof as described herein. Known glycolytic genes can also provide very efficient transcriptional control signals. For example, the promoter and terminator signals of the phosphoglycerate kinase gene can be utilized.

Production of antibodies or antigen-binding portions thereof as described herein in insects can be achieved. For example, by infecting the insect host with a baculovirus engineered to express a transmembrane polypeptide by methods known to those of ordinary skill in the art.

In some embodiments of any of the aspects, the introduced nucleotide sequence is incorporated into a plasmid or viral vector capable of autonomous replication in the recipient host. Any of a wide variety of vectors can be employed for this purpose and are known and available to those or ordinary skill in the art. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Example prokaryotic vectors known in the art include plasmids such as those capable of replication in E. coli., for example. Other gene expression elements useful for the expression of cDNA include, but are not limited to (a) viral transcription promoters and their enhancer elements, such as the SV40 early promoter, Rous sarcoma virus LTR, and Moloney murine leukemia virus; (b) splice regions and polyadenylation sites such as those derived from the SV40 late region, and (c) polyadenylation sites such as in SV40. Immunoglobulin cDNA genes can be expressed, e.g., using as expression elements the SV40 early promoter and its enhancer, the mouse immunoglobulin H chain promoter enhancers, SV40 late region mRNA splicing, rabbit S-globin intervening sequence, immunoglobulin and rabbit S-globin polyadenylation sites, and SV40 polyadenylation elements.

For immunoglobulin genes comprised of part cDNA, part genomic DNA, the transcriptional promoter can be human cytomegalovirus, the promoter enhancers can be cytomegalovirus and mouse/human immunoglobulin, and mRNA splicing and polyadenylation regions can be the native chromosomal immunoglobulin sequences.

In some embodiments of any of the aspects, for expression of cDNA genes in rodent cells, the transcriptional promoter is a viral LTR sequence, the transcriptional promoter enhancers are either or both the mouse immunoglobulin heavy chain enhancer and the viral LTR enhancer, the splice region contains an intron of greater than 31 bp, and the polyadenylation and transcription termination regions are derived from the native chromosomal sequence corresponding to the immunoglobulin chain being synthesized. In other embodiments, cDNA sequences encoding other proteins are combined with the above-recited expression elements to achieve expression of the proteins in mammalian cells.

A gene is assembled in, or inserted into, an expression vector. Recipient cells capable of expressing the chimeric immunoglobulin chain gene product are then transfected singly with an antibody, antigen-binding portion thereof, or CAR, or chimeric H or chimeric L chain-encoding gene, or are co-transfected with a chimeric H and a chimeric L chain gene. The transfected recipient cells are cultured under conditions that permit expression of the incorporated genes and the expressed immunoglobulin chains or intact antibodies or fragments are recovered from the culture.

In some embodiments of any of the aspects, the genes encoding the polypeptide or nucleic acid are assembled in separate expression vectors that are then used to co-transfect a recipient cell. Each vector can contain two selectable genes, a first selectable gene designed for selection in a bacterial system and a second selectable gene designed for selection in a eukaryotic system, wherein each vector has a different pair of genes. This strategy results in vectors which first direct the production, and permit amplification, of the genes in a bacterial system. The genes so produced and amplified in a bacterial host are subsequently used to co-transfect a eukaryotic cell, and allow selection of a co-transfected cell carrying the desired transfected genes. Non-limiting examples of selectable genes for use in a bacterial system are the gene that confers resistance to ampicillin and the gene that confers resistance to chloramphenicol. Selectable genes for use in eukaryotic transfectants include the xanthine guanine phosphoribosyl transferase gene (designated gpt) and the phosphotransferase gene from Tn5 (designated neo). Alternatively the genes can be assembled on the same expression vector.

For transfection of the expression vectors and production of the polypeptide or nucleic acids described herein, the recipient cell line can be a myeloma cell. Myeloma cells can synthesize, assemble and secrete immunoglobulins encoded by transfected immunoglobulin genes and possess the mechanism for glycosylation of the immunoglobulin. For example, In some embodiments of any of the aspects, the recipient cell is the recombinant Ig-producing myeloma cell SP2/0 (ATCC #CRL 8287). SP2/0 cells produce only immunoglobulin encoded by the transfected genes. Myeloma cells can be grown in culture or in the peritoneal cavity of a mouse, where secreted immunoglobulin can be obtained from ascites fluid. Other suitable recipient cells include lymphoid cells such as B lymphocytes of human or non-human origin, hybridoma cells of human or non-human origin, or interspecies heterohybridoma cells.

An expression vector carrying a polypeptide or nucleic acid as described herein can be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment, as known to one of ordinary skill in the art.

Traditionally, monoclonal antibodies have been produced as native molecules in murine hybridoma lines. In addition to that technology, the methods and compositions described herein provide for recombinant DNA expression of monoclonal antibodies. This allows the production of humanized antibodies as well as a spectrum of antibody derivatives and fusion proteins in a host species of choice. The production of antibodies in bacteria, yeast, transgenic animals and chicken eggs are also alternatives for hybridoma-based production systems. The main advantages of transgenic animals are potential high yields from renewable sources.

In one aspect, a cell comprising an isolated antibody, antigen-binding portion thereof, or CAR as described herein is provided. In some embodiments of any of the aspects, the isolated antibody, antigen-binding portion thereof, or CAR as described herein is expressed on the cell surface. In some embodiments of any of the aspects, the cell comprises a nucleic acid encoding an isolated antibody, antigen-binding portion thereof, or CAR as described herein.

In some embodiments of any of the aspects, the cell is an immune cell. As used herein, "immune cell" refers to a cell that plays a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes. In some embodiments of any of the aspects, the cell is a T cell; a NK cell; a NKT cell; lymphocytes, such as B cells and T cells; and myeloid cells, such as monocytes, macrophages, eosinophils, mast cells, basophils, and granulocytes.

In particular embodiments, a cell (e.g., an immune cell) is transduced with a retroviral vector, e.g., a lentiviral vector, encoding a CAR. For example, an immune effector cell is transduced with a vector encoding a CAR that comprises an anti-CHI3L1 antibody or antigen binding portion thereof that binds a CHI3L1 polypeptide, with an intracellular signaling domain of CD3ζ, CD28, 4-1BB, Ox40, or any combinations thereof. Thus, these transduced cells can elicit a CAR-mediated cytotoxic response.

Retroviruses are a common tool for gene delivery. In particular embodiments, a retrovirus is used to deliver a polynucleotide encoding a chimeric antigen receptor (CAR) to a cell. As used herein, the term "retrovirus" refers to an RNA virus that reverse transcribes its genomic RNA into a linear double-stranded DNA copy and subsequently covalently integrates its genomic DNA into a host genome. Once the virus is integrated into the host genome, it is referred to as a "provirus." The provirus serves as a template for RNA polymerase II and directs the expression of RNA molecules which encode the structural proteins and enzymes needed to produce new viral particles.

Illustrative retroviruses suitable for use in particular embodiments, include, but are not limited to: Moloney murine leukemia virus (M-MuLV), Moloney murine sarcoma virus (MoMSV), Harvey murine sarcoma virus (Ha-MuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) and lentivirus.

As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In one embodiment, HIV based vector backbones (i.e., HIV cis-acting sequence elements) are preferred. In particular embodiments, a lentivirus is used to deliver a polynucleotide comprising a CAR to a cell.

Retroviral vectors and more particularly lentiviral vectors may be used in practicing particular embodiments of the present invention. Accordingly, the term "retrovirus" or "retroviral vector", as used herein is meant to include "lentivirus" and "lentiviral vectors" respectively.

In some embodiments of any of the aspects, the agent that inhibits a given target is an inhibitory nucleic acid. In some embodiments of any of the aspects, inhibitors of the expression of a given gene can be an inhibitory nucleic acid. As used herein, "inhibitory nucleic acid" refers to a nucleic acid molecule which can inhibit the expression of a target, e.g., double-stranded RNAs (dsRNAs), inhibitory RNAs (iRNAs), miRNAs, amiRNAs, and the like.

Double-stranded RNA molecules (dsRNA) have been shown to block gene expression in a highly conserved regulatory mechanism known as RNA interference (RNAi). The inhibitory nucleic acids described herein can include an RNA strand (the antisense strand) having a region which is 30 nucleotides or less in length, i.e., 15-30 nucleotides in length, generally 19-24 nucleotides in length, which region is substantially complementary to at least part the targeted mRNA transcript. The use of these iRNAs enables the targeted degradation of mRNA transcripts, resulting in decreased expression and/or activity of the target.

As used herein, the term "iRNA" refers to an agent that contains RNA (or modified nucleic acids as described below herein) and which mediates the targeted cleavage of an RNA transcript via an RNA-induced silencing complex (RISC) pathway. In some embodiments of any of the aspects, an iRNA as described herein effects inhibition of the expression and/or translation and/or activity of a target, e.g. CHI3L1. In some embodiments of any of the aspects, contacting a cell with the inhibitor (e.g. an iRNA) results in a decrease in the target mRNA level in a cell by at least about 5%, about 10%, about 20%, about 30%, about 40%, about 50%, about 60%, about 70%, about 80%, about 90%, about 95%, about 99%, up to and including 100% of the target mRNA level found in the cell without the presence of the iRNA. In some embodiments of any of the aspects, administering an inhibitor (e.g. an iRNA) to a subject results in a decrease in the target mRNA level in the subject by at least about 5%, about 10%, about 20%, about 30%, about 40%, about 50%, about 60%, about 70%, about 80%, about 90%, about 95%, about 99%, up to and including 100% of the target mRNA level found in the subject without the presence of the iRNA.

In some embodiments of any of the aspects, the iRNA can be a dsRNA. A dsRNA includes two RNA strands that are sufficiently complementary to hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of the target, e.g., it can span one or more intron boundaries. The other strand (the sense strand) includes a region that is complementary to the antisense strand, such that the two strands hybridize and form a duplex structure when combined under suitable conditions. Generally, the duplex structure is between 15 and 30 base pairs in length inclusive, more generally between 18 and 25 base pairs in length inclusive, yet more generally between 19 and 24 base pairs in length inclusive, and most generally between 19 and 21 base pairs in length, inclusive. Similarly, the region of complementarity to the target sequence is between 15 and 30 base pairs in length inclusive, more generally between 18 and 25 base pairs in length inclusive, yet more generally between 19 and 24 base pairs in length inclusive, and most generally between 19 and 21 base pairs in length nucleotides in length, inclusive. In some embodiments of any of the aspects, the dsRNA is between 15 and 20 nucleotides in length, inclusive, and in other embodiments, the dsRNA is between 25 and 30 nucleotides in length, inclusive. As the ordinarily skilled person will recognize, the targeted region of an RNA targeted for cleavage will most often be part of a larger RNA molecule, often an mRNA molecule. Where relevant, a "part" of an mRNA target is a contiguous sequence of an mRNA target of sufficient length to be a substrate for RNAi-directed cleavage (i.e., cleavage through a RISC pathway). dsRNAs having duplexes as short as 9 base pairs can, under some circumstances, mediate RNAi-directed RNA cleavage. Most often a target will be at least 15 nucleotides in length, preferably 15-30 nucleotides in length.

Exemplary embodiments of types of inhibitory nucleic acids can include, e.g., siRNA, shRNA, miRNA, and/or amiRNA, which are well known in the art.

In some embodiments of any of the aspects, the RNA of an iRNA, e.g., a dsRNA, is chemically modified to enhance stability or other beneficial characteristics. The nucleic acids described herein may be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of RNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments of any of the aspects, the modified RNA will have a phosphorus atom in its internucleoside backbone.

Modified RNA backbones can include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included. Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; others having mixed N, O, S and CH2 component parts, and oligonucleosides with heteroatom backbones, and in particular —CH2-NH—CH2-, —CH2-N(CH3)-O—CH2-[known as a methylene (methylimino) or MMI backbone], —CH2-O—N(CH3)-CH2-, —CH2-N(CH3)-N(CH3)-CH2- and —N(CH3)-CH2-CH2- [wherein the native phosphodiester backbone is represented as —O—P—O—CH2-].

In other RNA mimetics suitable or contemplated for use in iRNAs, both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) Nucleic Acids Research 33(1):439-447; Mook, O R. et al., (2007) Mol Canc Ther 6(3):833-843; Grunweller, A. et al., (2003) Nucleic Acids Research 31(12): 3185-3193).

Modified RNAs can also contain one or more substituted sugar moieties. The iRNAs, e.g., dsRNAs, described herein can include one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Exemplary suitable modifications include O[(CH2)nO]mCH3, O(CH2).nOCH3, O(CH2) nNH2, O(CH2)nCH3, O(CH2)nONH2, and O(CH2)nON [(CH2)nCH3)]2, where n and m are from 1 to about 10. In some embodiments of any of the aspects, dsRNAs include one of the following at the 2' position: C1 to C10 lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments of any of the aspects, the modification includes a 2' methoxyethoxy (2'-O—CH2CH2OCH3, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a O(CH2)2ON(CH3)2 group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH2-O—CH2-N(CH2)2, also described in examples herein below.

Other modifications include 2'-methoxy (2'-OCH3), 2'-aminopropoxy (2'-OCH2CH2CH2NH2) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs may also have sugar mimetics such as cyclobutyl moieties in place of the pentofuranosyl sugar.

An inhibitory nucleic acid can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Certain of these nucleobases are particularly useful for increasing the binding affinity of the inhibitory nucleic acids featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

The preparation of the modified nucleic acids, backbones, and nucleobases described above are well known in the art.

Another modification of an inhibitory nucleic acid featured in the invention involves chemically linking to the inhibitory nucleic acid to one or more ligands, moieties or conjugates that enhance the activity, cellular distribution, pharmacokinetic properties, or cellular uptake of the iRNA. Such moieties include but are not limited to lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994, 4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylaminocarbonyloxycholesterol moiety (Crooke et al., J. Pharmacol. Exp. Ther., 1996, 277:923-937).

In some embodiments of any of the aspects, a polypeptide, nucleic acid, or cell as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

In some embodiments of any of the aspects, a nucleic acid encoding a polypeptide as described herein (e.g. an antibody or antibody reagent) is comprised by a vector. In some of the aspects described herein, a nucleic acid sequence encoding a given polypeptide as described herein, or any module thereof, is operably linked to a vector. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated." The terms "purified" or "substantially purified" refer to an isolated nucleic acid or polypeptide that is at least 95% by weight the subject nucleic acid or polypeptide, including, for example, at least 96%, at least 97%, at least 98%, at least 99% or more. In some embodiments of any of the aspects, the antibody, antigen-binding portion thereof, or CAR described herein is isolated. In some embodiments of any of the aspects, the antibody, antibody reagent, antigen-binding portion thereof, or CAR described herein is purified.

As used herein, "engineered" refers to the aspect of having been manipulated by the hand of man. For example, an antibody, antibody reagent, antigen-binding portion thereof, or CAR is considered to be "engineered" when the sequence of the antibody, antibody reagent, antigen-binding portion thereof, or CAR is manipulated by the hand of man to differ from the sequence of an antibody as it exists in nature. As is common practice and is understood by those in the art, progeny and copies of an engineered polynucleotide and/or polypeptide are typically still referred to as "engineered" even though the actual manipulation was performed on a prior entity.

As used herein, an "epitope" can be formed on a polypeptide both from contiguous amino acids, or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5, about 9, or about 8-10 amino acids in a unique spatial conformation. An "epitope" includes the unit of structure conventionally bound by an immunoglobulin VH/VL pair. Epitopes define the minimum binding site for an antibody, and thus represent the target of specificity of an antibody. In the case of a single domain antibody, an epitope represents the unit of structure bound by a variable domain in isolation. The terms "antigenic determinant" and "epitope" can also be used interchangeably herein. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics.

"Avidity" is the measure of the strength of binding between an antigen-binding molecule (such as an antibody or antigen-binding portion thereof described herein) and the pertinent antigen. Avidity is related to both the affinity between an antigenic determinant and its antigen binding site on the antigen-binding molecule, and the number of pertinent binding sites present on the antigen-binding molecule. Typically, antigen-binding proteins (such as an antibody or portion of an antibody as described herein) will bind to their cognate or specific antigen with a dissociation constant (KD of $10^{-5}$ to $10^{-12}$ moles/liter or less, such as $10^{-7}$ to $10^{-12}$ moles/liter or less, or $10^{-8}$ to $10^{-12}$ moles/liter (i.e., with an association constant (KA) of $10^5$ to $10^{12}$ liter/moles or more, such as $10^7$ to $10^{12}$ liter/moles or $10^8$ to $10^{12}$ liter/moles). Any KD value greater than $10^{-4}$ mol/liter (or any KA value lower than $10^4$ $M^{-1}$) is generally considered to indicate non-specific binding. The KD for biological interactions which are considered meaningful (e.g., specific) are typically in the range of $10^{-10}$ M (0.1 nM) to $10^{-5}$ M (10000 nM). The stronger an interaction, the lower is its KD. For example, a binding site on an antibody or portion thereof described herein will bind to the desired antigen with an affinity less than 500 nM, such as less than 200 nM, or less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as other techniques as mentioned herein.

Accordingly, as used herein, "selectively binds" or "specifically binds" refers to the ability of an peptide (e.g., an antibody, CAR or portion thereof) described herein to bind to a target, such as an antigen present on the cell-surface of a cancer cell, with a KD $10^{-5}$M (10000 nM) or less, e.g., $10^{-6}$M, $10^{-7}$M, $10^{-8}$ M, $10^{-9}$M, $10^{-10}$ M, $10^{-11}$M, $10^{-12}$M, or less. Specific binding can be influenced by, for example, the affinity and avidity of the polypeptide agent and the concentration of polypeptide agent. The person of ordinary skill in the art can determine appropriate conditions under which the polypeptide agents described herein selectively bind the targets using any suitable methods, such as titration of a polypeptide agent in a suitable cell binding assay. A polypeptide specifically bound to a target is not displaced by a non-similar competitor. In certain embodiments, an antibody, antigen-binding portion thereof, or CAR is said to specifically bind an antigen when it preferentially recognizes its target antigen in a complex mixture of proteins and/or macromolecules.

In some embodiments of any of the aspects, an antibody, antigen-binding portion thereof, and/or CAR as described herein binds to CHI3L1 with a dissociation constant (KD) of $10^{-5}$ M (10000 nM) or less, e.g., $10^{-6}$ M, $10^{-7}$ M, $10^{-8}$ M, $10^{-9}$ M, $10^{-10}$ M, $10^{-11}$M, $10^{-12}$ M, or less. In some embodiments of any of the aspects, an antibody, antigen-binding portion thereof, and/or CAR as described herein binds to CHI3L1 with a dissociation constant ($K_D$) of from about $10^{-5}$ M to $10^{-6}$ M. In some embodiments of any of the aspects, an antibody, antigen-binding portion thereof, and/or CAR as described herein binds to CHI3L1 with a dissociation constant ($K_D$) of from about $10^{-6}$ M to $10^{-7}$ M. In some embodiments of any of the aspects, an antibody, antigen-binding portion thereof, and/or CAR as described herein binds to CHI3L1 with a dissociation constant ($K_D$) of from about $10^{-7}$ M to $10^{-8}$ M. In some embodiments of any of the aspects, an antibody, antigen-binding portion thereof, and/or CAR as described herein binds to CHI3L1 with a dissociation constant ($K_D$) of from about $10^{-8}$ M to $10^{-9}$ M. In some embodiments of any of the aspects, an antibody, antigen-binding portion thereof, and/or CAR as described herein binds to CHI3L1 with a dissociation constant ($K_D$) of from about $10^{-9}$ M to $10^{-10}$ M. In some embodiments of any of the aspects, an antibody, antigen-binding portion thereof, and/or CAR as described herein binds to CHI3L1 with a dissociation constant (KD) of from about $10^{-10}$ M to $10^{-11}$ M. In some embodiments of any of the aspects, an antibody, antigen-binding portion thereof, and/or CAR as described herein binds to CHI3L1 with a dissociation constant (KD) of from about $10^{-11}$ M to $10^{-12}$ M. In some embodiments of any of the aspects, an antibody, antigen-binding portion thereof, and/or CAR as described herein binds to CHI3L1 with a dissociation constant (KD) of less than $10^{-12}$ M.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "agent" refers generally to any entity which is normally not present or not present at the levels being administered to a cell, tissue or subject. An agent can be selected from a group including but not limited to: polynucleotides; polypeptides; small molecules; and antibodies or antigen-binding fragments thereof. A polynucleotide can be RNA or DNA, and can be single or double stranded, and can be selected from a group including, for example, nucleic acids and nucleic acid analogues that encode a polypeptide. A polypeptide can be, but is not limited to, a naturally-occurring polypeptide, a mutated polypeptide or a fragment thereof that retains the function of interest. Further examples of agents include, but are not limited to a nucleic acid aptamer, peptide-nucleic acid (PNA), locked nucleic acid (LNA), small organic or inorganic molecules; saccharide; oligosaccharides; polysaccharides; biological macromolecules, peptidomimetics; nucleic acid analogs and derivatives; extracts made from biological materials such as bacteria, plants, fungi, or mammalian cells or tissues and naturally occurring or synthetic compositions. An agent can be applied to the media, where it contacts the cell and induces its effects. Alternatively, an agent can be intracellular as a result of introduction of a nucleic acid sequence encoding the agent into the cell and its transcription resulting in the production of the nucleic acid and/or protein environmental stimuli within the cell. In some embodiments of any of the aspects, the agent is any chemical, entity or moiety, including without limitation synthetic and naturally-occurring non-proteinaceous entities. In certain embodiments the agent is a small molecule having a chemical moiety selected, for example, from unsubstituted or substituted alkyl, aromatic, or heterocyclyl moieties including macrolides, leptomycins and related natural products or analogues thereof. Agents can be known to have a desired activity and/or property, or can be selected from a library of diverse compounds. As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight more than about 50, but less than about 5000 Daltons (5 kD). Preferably the small molecule has a molecular weight of less than 3 kD, still more preferably less than 2 kD, and most preferably less than 1 kD. In some cases it is preferred that a small molecule have a molecular mass equal to or less than 700 Daltons.

The term "aptamer" refers to a nucleic acid molecule that is capable of binding to a target molecule, such as a polypeptide. For example, an aptamer of the invention can specifically bind to a target molecule, or to a molecule in a signaling pathway that modulates the expression and/or activity of a target molecule. The generation and therapeutic use of aptamers are well established in the art. See, e.g., U.S. Pat. No. 5,475,096.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4$^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeck, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

One of skill in the art can readily identify a chemotherapeutic agent of use (e.g. see Physicians' Cancer Chemotherapy Drug Manual 2014, Edward Chu, Vincent T. DeVita Jr., Jones & Bartlett Learning; Principles of Cancer Therapy, Chapter 85 in Harrison's Principles of Internal Medicine, 18th edition; Therapeutic Targeting of Cancer Cells: Era of Molecularly Targeted Agents and Cancer Pharmacology, Chs. 28-29 in Abeloff s Clinical Oncology, 2013 Elsevier; and Fischer D S (ed): The Cancer Chemotherapy Handbook, 4th ed. St. Louis, Mosby-Year Book, 2003).

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method of treating cancer in a subject in need thereof, the method comprising administering:
   an inhibitor of CHI3L1; and
   an inhibitor of an immune checkpoint protein.
2. The method of paragraph 1, wherein the inhibitor of CHI3L1 is an antibody, antibody reagent, antigen-binding fragment thereof, or CAR that specifically binds to CHI3L1.
3. The method of paragraph 2, wherein an antibody, antibody reagent, antigen-binding fragment thereof, or CAR comprises at least one heavy or light chain complementarity determining region (CDR) selected from the group consisting of:
   (a) a light chain CDR1 having the amino acid sequence of SEQ ID NO: 4;
   (b) a light chain CDR2 having the amino acid sequence of SEQ ID NO: 5;
   (c) a light chain CDR3 having the amino acid sequence of SEQ ID NO: 6;
   (d) a heavy chain CDR1 having the amino acid sequence of SEQ ID NO: 1;
   (e) a heavy chain CDR2 having the amino acid sequence of SEQ ID NO: 2; and (f) a heavy chain CDR3 having the amino acid sequence of SEQ ID NO: 3; or
a conservative substitution variant of one or more of (a)-(f).
4. The method of paragraph 3, wherein the antibody, antibody reagent, antigen-binding portion thereof, or CAR of comprises heavy chain CDRs having the amino acid sequences of SEQ ID NOs: 1-3 or a conservative substitution variant of such amino acid sequence.
5. The method of any of paragraphs 3-4, wherein the antibody, antibody reagent, antigen-binding portion thereof or CAR comprises light chain CDRs having the amino acid sequences of SEQ ID NOs: 4-6 or a conservative substitution variant of such amino acid sequence.
6. The method of any of paragraphs 3-5, wherein the antibody, antibody reagent, antigen-binding portion thereof or CAR comprises light chain CDRs having the amino acid sequences of SEQ ID NOs: 4-6 and heavy chain CDRs having the amino acid sequences of SEQ ID NOs: 1-3 or a conservative substitution variant of such amino acid sequence.
7. The method of paragraph 2, wherein the inhibitor of CHI3L1 is antibody, antibody reagent, antigen-binding portion thereof or CAR that competes for binding to CHI3L1 with an antibody comprising light chain CDRs having the amino acid sequences of SEQ ID NOs: 4-6 and heavy chain CDRs having the amino acid sequences of SEQ ID NOs: 1-3.
8. The method of any of paragraphs 1-7, wherein the inhibitor of CHI3L1 binds a CHI3L1 polypeptide at an epitope selected from SEQ ID NOs: 13-24.
9. The method of paragraph 1, wherein the inhibitor of CHI3L1 is an inhibitor of a CHI3L1 receptor.
10. The method of paragraph 9, wherein the CHI3L1 receptor is IL13Rα2, TMEM219, or CRTH2.
11. The method of any of paragraphs 9-10, wherein the inhibitor is an inhibitory antibody or nucleic acid molecule.
12. The method of any of paragraph 1-11, wherein the cancer is a primary cancer or a metastatic cancer.
13. The method of any of paragraphs 1-12, wherein the cancer is malignant cancer.
14. The method of any of paragraphs 1-13, wherein the cancer is selected from the group consisting of:
prostate cancer, colon cancer, rectal cancer, ovarian cancer, kidney cancer, breast cancer, glioblastoma, melanoma, malignant melanoma, and lung cancer.
15. The method of any of paragraphs 1-14, wherein the inhibitor of an immune checkpoint protein is an antibody, antibody reagent, antigen-binding fragment thereof, or CAR that specifically binds to at least one immune checkpoint protein.
16. The method of any of paragraphs 1-15, wherein the inhibitor of an immune checkpoint protein is a natural ligand thereof
17. The method of paragraph 16, wherein the natural ligand comprises PD-L1 or B7.
18. The method of any of paragraphs 1-17, wherein the immune checkpoint protein is selected from the group consisting of:
PD-1; PD-L1; PD-L2; TIM-3; CTLA4; TIGTT; DD1-α; A2AR; B7-H3; B7-H4; BTLA; IDO; TDO; KIR; and LAG3.
19. The method of paragraph 18, wherein the inhibitor of an immune checkpoint protein is selected from the group consisting of:
MGA271; ipilimumab; pembrolizumab; nivolumab; atezolizumab; galiximab; IMP321; BMS-986016; SMB-663513; PF-05082566; IPH2101; KW-0761; CDX-1127; MEDI-6769; CP-870,893; tremelimumab; pidilizumab; MPDL3280A; MEDI4736; MSB0010718C; AUNP12; avelumab; and durvalumab.
20. The method of any of paragraphs 1-19, wherein the inhibitor of CHI3L1 and the inhibitor of an immune checkpoint protein are present in the same bivalent antibody reagent.
21. The method of paragraph 20, wherein the immune checkpoint protein is PD-1 or CTLA4.
22. The method of any of paragraphs 1-21, wherein the subject is a subject determined to have an elevated level of CHI3L1.
23. The method of paragraph 22, wherein the CHI3L1 is circulating CHI3L1.
24. A pharmaceutical composition comprising
an inhibitor of CHI3L1; and
an inhibitor of an immune checkpoint protein.
25. A kit comprising
a pharmaceutical composition comprising an inhibitor of CHI3L1; and
a pharmaceutical composition comprising an inhibitor of an immune checkpoint protein.
26. The kit or composition of any of paragraphs 24-25, wherein the inhibitor of CHI3L1 is an antibody, antibody reagent, antigen-binding fragment thereof, or CAR that specifically binds to CHI3L1.
27. The kit or composition of paragraph 26, wherein an antibody, antibody reagent, antigen-binding fragment thereof, or CAR comprises at least one heavy or light chain complementarity determining region (CDR) selected from the group consisting of:
(a) a light chain CDR1 having the amino acid sequence of SEQ ID NO: 4;
(b) a light chain CDR2 having the amino acid sequence of SEQ ID NO: 5;
(c) a light chain CDR3 having the amino acid sequence of SEQ ID NO: 6;
(d) a heavy chain CDR1 having the amino acid sequence of SEQ ID NO: 1;
(e) a heavy chain CDR2 having the amino acid sequence of SEQ ID NO: 2; and
(f) a heavy chain CDR3 having the amino acid sequence of SEQ ID NO: 3; or
a conservative substitution variant of one or more of (a)-(f).
28. The kit or composition of any of paragraphs 26-27, wherein the antibody, antibody reagent, antigen-binding portion thereof, or CAR of comprises heavy chain CDRs having the amino acid sequences of SEQ ID NOs: 1-3 or a conservative substitution variant of such amino acid sequence.
29. The kit or composition of any of paragraphs 26-28, wherein the antibody, antibody reagent, antigen-binding portion thereof or CAR comprises light chain CDRs having the amino acid sequences of SEQ ID NOs: 4-6 or a conservative substitution variant of such amino acid sequence.
30. The kit or composition of any of paragraphs 26-29, wherein the antibody, antibody reagent, antigen-binding portion thereof or CAR comprises light chain CDRs having the amino acid sequences of SEQ ID NOs: 4-6 and heavy chain CDRs having the amino acid sequences of SEQ ID NOs: 1-3 or a conservative substitution variant of such amino acid sequence.

31. The kit or composition of any of paragraphs 24-25, wherein the inhibitor of CHI3L1 is antibody, antibody reagent, antigen-binding portion thereof or CAR that competes for binding to CHI3L1 with an antibody comprising light chain CDRs having the amino acid sequences of SEQ ID NOs: 4-6 and heavy chain CDRs having the amino acid sequences of SEQ ID NOs: 1-3.

32. The kit or composition of any of paragraphs 24-31, wherein the inhibitor of CHI3L1 binds a CHI3L1 polypeptide at an epitope selected from SEQ ID NOs: 13-24.

33. The kit or composition of any of paragraphs 24-25, wherein the inhibitor of CHI3L1 is an inhibitor of a CHI3L1 receptor.

34. The kit or composition of paragraph 33, wherein the CHI3L1 receptor is IL13Rα2, TMEM219, or CRTH2.

35. The kit or composition of any of paragraphs 33-34, wherein the inhibitor is an inhibitory antibody or nucleic acid molecule.

36. The kit or composition of any of paragraphs 24-35, wherein the inhibitor of an immune checkpoint protein is an antibody, antibody reagent, antigen-binding fragment thereof, or CAR that specifically binds to at least one immune checkpoint protein.

37. The kit or composition of any of paragraphs 24-36, wherein the inhibitor of an immune checkpoint protein is a natural ligand thereof.

38. The kit or composition of paragraph 37, wherein the natural ligand comprises PD-L1 or B7.

39. The kit or composition of any of paragraphs 24-38, wherein the immune checkpoint protein is selected from the group consisting of:
PD-1; PD-L1; PD-L2; TIM-3; CTLA4; TIGIT; DD1-α; A2AR; B7-H3; B7-H4; BTLA; IDO; TDO; KIR; and LAG3.

40. The kit or composition of paragraph 39, wherein the inhibitor of an immune checkpoint protein is selected from the group consisting of:
MGA271; ipilimumab; pembrolizumab; nivolumab; atezolizumab; galiximab; IMP321; BMS-986016; SMB-663513; PF-05082566; IPH2101; KW-0761; CDX-1127; MEDI-6769; CP-870,893; tremelimumab; pidilizumab; MPDL3280A; MEDI4736; MSB0010718C; AUNP12; avelumab; and durvalumab.

41. The kit or composition of any of paragraphs 24-40, wherein the inhibitor of CHI3L1 and the inhibitor of an immune checkpoint protein are present in the same bivalent antibody reagent.

42. The kit or composition of paragraph 41, wherein the immune checkpoint protein is PD-1 or CTLA4.

43. A therapeutically effective amount of an inhibitor of CHI3L1 and an inhibitor of an immune checkpoint protein for use in the treatment of cancer.

44. The inhibitors of paragraph 43, wherein the inhibitor of CHI3L1 and the inhibitor of an immune checkpoint protein are present in the same composition.

45. The inhibitors of paragraph 43, wherein the inhibitor of CHI3L1 and the inhibitor of an immune checkpoint protein are present in separate compositions.

46. The inhibitors of any of paragraphs 43-45, wherein the inhibitor of CHI3L1 is an antibody, antibody reagent, antigen-binding fragment thereof, or CAR that specifically binds to CHI3L1.

47. The inhibitors of paragraph 46, wherein an antibody, antibody reagent, antigen-binding fragment thereof, or CAR comprises at least one heavy or light chain complementarity determining region (CDR) selected from the group consisting of:

(a) a light chain CDR1 having the amino acid sequence of SEQ ID NO: 4;
(b) a light chain CDR2 having the amino acid sequence of SEQ ID NO: 5;
(c) a light chain CDR3 having the amino acid sequence of SEQ ID NO: 6;
(d) a heavy chain CDR1 having the amino acid sequence of SEQ ID NO: 1;
(c) a heavy chain CDR2 having the amino acid sequence of SEQ ID NO: 2; and
(f) a heavy chain CDR3 having the amino acid sequence of SEQ ID NO: 3; or
a conservative substitution variant of one or more of (a)-(f).

48. The inhibitors of any of paragraphs 46-48, wherein the antibody, antibody reagent, antigen-binding portion thereof, or CAR of comprises heavy chain CDRs having the amino acid sequences of SEQ ID NOs: 1-3 or a conservative substitution variant of such amino acid sequence.

49. The inhibitors of any of paragraphs 46-48, wherein the antibody, antibody reagent, antigen-binding portion thereof or CAR comprises light chain CDRs having the amino acid sequences of SEQ ID NOs: 4-6 or a conservative substitution variant of such amino acid sequence.

50. The inhibitors of any of paragraphs 46-49, wherein the antibody, antibody reagent, antigen-binding portion thereof or CAR comprises light chain CDRs having the amino acid sequences of SEQ ID NOs: 4-6 and heavy chain CDRs having the amino acid sequences of SEQ ID NOs: 1-3 or a conservative substitution variant of such amino acid sequence.

51. The inhibitors of any of paragraphs 43-45, wherein the inhibitor of CHI3L1 is antibody, antibody reagent, antigen-binding portion thereof or CAR that competes for binding to CHI3L1 with an antibody comprising light chain CDRs having the amino acid sequences of SEQ ID NOs: 4-6 and heavy chain CDRs having the amino acid sequences of SEQ ID NOs: 1-3.

52. The inhibitors of any of paragraphs 43-51, wherein the inhibitor of CHI3L1 binds a CHI3L1 polypeptide at an epitope selected from SEQ ID NOs: 13-24.

53. The inhibitors of any of paragraphs 43-52, wherein the inhibitor of CHI3L1 is an inhibitor of a CHI3L1 receptor.

54. The inhibitors of paragraph 53, wherein the CHI3L1 receptor is IL13Rα2, TMEM219, or CRTH2.

55. The inhibitors of any of paragraphs 43-54, wherein the inhibitor is an inhibitory antibody or nucleic acid molecule.

56. The inhibitors of any of paragraphs 43-55, wherein the cancer is a primary cancer or a metastatic cancer.

57. The inhibitors of any of paragraphs 43-56, wherein the cancer is malignant cancer.

58. The inhibitors of any of paragraphs 43-57, wherein the cancer is selected from the group consisting of:
prostate cancer, colon cancer, rectal cancer, ovarian cancer, kidney cancer, breast cancer, glioblastoma, melanoma, malignant melanoma, and lung cancer.

59. The inhibitors of any of paragraphs 43-58, wherein the inhibitor of an immune checkpoint protein is an antibody, antibody reagent, antigen-binding fragment thereof, or CAR that specifically binds to at least one immune checkpoint protein.

60. The inhibitors of any of paragraphs 43-59, wherein the inhibitor of an immune checkpoint protein is a natural ligand thereof 61. The inhibitors of paragraph 60, wherein the natural ligand comprises PD-L1 or B7.
62. The inhibitors of any of paragraphs 43-61, wherein the immune checkpoint protein is selected from the group consisting of:
PD-1; PD-L1; PD-L2; TIM-3; CTLA4; TIGIT; DD1-α; A2AR; B7-H3; B7-H4; BTLA; IDO; TDO; KIR; and LAG3.
63. The inhibitors of paragraph 62, wherein the inhibitor of an immune checkpoint protein is selected from the group consisting of:
MGA271; ipilimumab; pembrolizumab; nivolumab; atezolizumab; galiximab; IMP321; BMS-986016; SMB-663513; PF-05082566; IPH2101; KW-0761; CDX-1127; MEDI-6769; CP-870,893; tremelimumab; pidilizumab; MPDL3280A; MEDI4736; MSB0010718C; AUNP12; avelumab; and durvalumab.
64. The inhibitors of any of paragraphs 43-63, wherein the inhibitor of CHI3L1 and the inhibitor of an immune checkpoint protein are present in the same bivalent antibody reagent.
65. The inhibitors of paragraph 64, wherein the immune checkpoint protein is PD-1 or CTLA4.
66. The inhibitors of any of paragraphs 43-64, wherein the inhibitors are administered to a subject determined to have an elevated level of CHI3L1.
67. The inhibitors of 66, wherein the CHI3L1 is circulating CHI3L1.

Some embodiments of the technology described herein can be defined according to any of the following numbered paragraphs:
1. A method of treating cancer in a subject in need thereof, the method comprising administering:
a) an inhibitor of an immune checkpoint protein; and.
b) at least one agent selected from:
i) an inhibitor of Sema7A;
ii) an inhibitor of β1-integrin;
iii) an agonist of PlexinC1; and
iv) an inhibitor of CHI3L1.
2. The method of paragraph 1, wherein the inhibitor of CHI3L1 is an antibody, antibody reagent, antigen-binding fragment thereof, or CAR that specifically binds to CHI3L1.
3. The method of paragraph 2, wherein an antibody, antibody reagent, antigen-binding fragment thereof, or CAR comprises at least one heavy or light chain complementarity determining region (CDR) selected from the group consisting of:
(a) a light chain CDR1 having the amino acid sequence of SEQ ID NO: 4;
(b) a light chain CDR2 having the amino acid sequence of SEQ ID NO: 5;
(c) a light chain CDR3 having the amino acid sequence of SEQ ID NO: 6;
(d) a heavy chain CDR1 having the amino acid sequence of SEQ ID NO: 1;
(e) a heavy chain CDR2 having the amino acid sequence of SEQ ID NO: 2; and
(f) a heavy chain CDR3 having the amino acid sequence of SEQ ID NO: 3; or
a conservative substitution variant of one or more of (a)-(f).
4. The method of paragraph 3, wherein the antibody, antibody reagent, antigen-binding portion thereof, or CAR of comprises heavy chain CDRs having the amino acid sequences of SEQ ID NOs: 1-3 or a conservative substitution variant of such amino acid sequence.
5. The method of any of paragraphs 3-4, wherein the antibody, antibody reagent, antigen-binding portion thereof or CAR comprises light chain CDRs having the amino acid sequences of SEQ ID NOs: 4-6 or a conservative substitution variant of such amino acid sequence.
6. The method of any of paragraphs 3-5, wherein the antibody, antibody reagent, antigen-binding portion thereof or CAR comprises light chain CDRs having the amino acid sequences of SEQ ID NOs: 4-6 and heavy chain CDRs having the amino acid sequences of SEQ ID NOs: 1-3 or a conservative substitution variant of such amino acid sequence.
7. The method of paragraph 2, wherein the inhibitor of CHI3L1 is antibody, antibody reagent, antigen-binding portion thereof or CAR that competes for binding to CHI3L1 with an antibody comprising light chain CDRs having the amino acid sequences of SEQ ID NOs: 4-6 and heavy chain CDRs having the amino acid sequences of SEQ ID NOs: 1-3.
8. The method of any of paragraphs 1-7, wherein the inhibitor of CHI3L1 binds a CHI3L1 polypeptide at an epitope selected from SEQ ID NOs: 13-24.
9. The method of paragraph 1, wherein the inhibitor of CHI3L1 is an inhibitor of a CHI3L1 receptor.
10. The method of paragraph 9, wherein the CHI3L1 receptor is IL13Rα2, TMEM219, or CRTH2.
11. The method of any of paragraphs 9-10, wherein the inhibitor of Chi3L1 or the immune checkpoint protein is an inhibitory antibody or nucleic acid molecule.
12. The method of any of paragraphs 1-11, wherein the inhibitor of Sema7A or β1-integrin is an inhibitory antibody reagent or nucleic acid molecule.
13. The method of any of paragraph 1-12, comprising administering at least the inhibitor of Sema7A and the inhibitor of β1-integrin.
14. The method of paragraph 13, wherein a bivalent antibody reagent comprises the inhibitor of Sema7A and the inhibitor of β1-integrin.
15. The method of any of paragraphs 1-14, wherein the agonist of PlexinC1 is a nucleic acid encoding Growth Arrest Specific 5 (GAS5).
16. The method of any of paragraphs 1-15, wherein the cancer is a primary cancer or a metastatic cancer.
17. The method of any of paragraphs 1-16, wherein the cancer is malignant cancer.
18. The method of any of paragraphs 1-17, wherein the cancer is selected from the group consisting of:
prostate cancer, colon cancer, rectal cancer, ovarian cancer, kidney cancer, breast cancer, glioblastoma, melanoma, malignant melanoma, and lung cancer.
19. The method of any of paragraphs 1-18, wherein the inhibitor of an immune checkpoint protein is an antibody, antibody reagent, antigen-binding fragment thereof, or CAR that specifically binds to at least one immune checkpoint protein.
20. The method of any of paragraphs 1-19, wherein the inhibitor of an immune checkpoint protein is a natural ligand thereof.
21. The method of paragraph 20, wherein the natural ligand comprises PD-L1 or B7.
22. The method of any of paragraphs 1-21, wherein the immune checkpoint protein is selected from the group consisting of:
PD-1; PD-L1; PD-L2; TIM-3; CTLA4; TIGIT; DD1-α; A2AR; B7-H3; B7-H4; BTLA; IDO; TDO; KIR; and LAG3.

23. The method of paragraph 22, wherein the inhibitor of an immune checkpoint protein is selected from the group consisting of:
MGA271; ipilimumab; pembrolizumab; nivolumab; atezolizumab; galiximab; IMP321; BMS-986016; SMB-663513; PF-05082566; IPH2101; KW-0761; CDX-1127; MEDI-6769; CP-870,893; tremelimumab; pidilizumab; MPDL3280A; MEDI4736; MSB0010718C; AUNP12; avelumab; and durvalumab.

24. The method of any of paragraphs 1-23, wherein a) the inhibitor of CHI3L1, the inhibitor of Sema7A, the inhibitor of β1-integrin, and/or the agonist of PlexinC1 and b) the inhibitor of an immune checkpoint protein are present in the same bivalent antibody reagent.

25. The method of paragraph 24, wherein the immune checkpoint protein is PD-1 or CTLA4.

26. The method of any of paragraphs 1-25, wherein the subject is a subject determined to have an elevated level of CHI3L1.

27. The method of paragraph 26, wherein the CHI3L1 is circulating CHI3L1.

28. A bi-specific antibody reagent comprising
    a) an inhibitor of CHI3L1, an inhibitor of Sema7A, an inhibitor of β1-integrin, and/or an agonist of PlexinC1; and
    b) an inhibitor of an immune checkpoint protein.

29. A bi-specific antibody reagent comprising
    an inhibitor of Sema7A; and
    an inhibitor of β1-integrin.

30. A pharmaceutical composition comprising
    a) an inhibitor of an immune checkpoint protein; and.
    b) at least one agent selected from:
       i) an inhibitor of Sema7A;
       ii) an inhibitor of β1-integrin;
       iii) an agonist of PlexinC1; and
       iv) an inhibitor of CHI3L1.

31. A kit comprising
    a) a pharmaceutical composition comprising an inhibitor of an immune checkpoint protein; and.
    b) at least one pharmaceutical composition comprising at least one agent selected from:
       i) an inhibitor of Sema7A;
       ii) an inhibitor of β1-integrin;
       iii) an agonist of PlexinC1; and
       iv) an inhibitor of CHI3L1.

32. The kit or composition of any of paragraphs 30-32, wherein the inhibitor of CHI3L1 is an antibody, antibody reagent, antigen-binding fragment thereof, or CAR that specifically binds to CHI3L1.

33. The kit or composition of paragraph 32, wherein an antibody, antibody reagent, antigen-binding fragment thereof, or CAR comprises at least one heavy or light chain complementarity determining region (CDR) selected from the group consisting of:
    (a) a light chain CDR1 having the amino acid sequence of SEQ ID NO: 4;
    (b) a light chain CDR2 having the amino acid sequence of SEQ ID NO: 5;
    (c) a light chain CDR3 having the amino acid sequence of SEQ ID NO: 6;
    (d) a heavy chain CDR1 having the amino acid sequence of SEQ ID NO: 1;
    (e) a heavy chain CDR2 having the amino acid sequence of SEQ ID NO: 2; and
    (f) a heavy chain CDR3 having the amino acid sequence of SEQ ID NO: 3; or
    a conservative substitution variant of one or more of (a)-(f).

34. The kit or composition of any of paragraphs 32-33, wherein the antibody, antibody reagent, antigen-binding portion thereof, or CAR of comprises heavy chain CDRs having the amino acid sequences of SEQ ID NOs: 1-3 or a conservative substitution variant of such amino acid sequence.

35. The kit or composition of any of paragraphs 32-34, wherein the antibody, antibody reagent, antigen-binding portion thereof or CAR comprises light chain CDRs having the amino acid sequences of SEQ ID NOs: 4-6 or a conservative substitution variant of such amino acid sequence.

36. The kit or composition of any of paragraphs 32-35, wherein the antibody, antibody reagent, antigen-binding portion thereof or CAR comprises light chain CDRs having the amino acid sequences of SEQ ID NOs: 4-6 and heavy chain CDRs having the amino acid sequences of SEQ ID NOs: 1-3 or a conservative substitution variant of such amino acid sequence.

37. The kit or composition of any of paragraphs 32-36, wherein the inhibitor of CHI3L1 is antibody, antibody reagent, antigen-binding portion thereof or CAR that competes for binding to CHI3L1 with an antibody comprising light chain CDRs having the amino acid sequences of SEQ ID NOs: 4-6 and heavy chain CDRs having the amino acid sequences of SEQ ID NOs: 1-3.

38. The kit or composition of any of paragraphs 32-37, wherein the inhibitor of CHI3L1 binds a CHI3L1 polypeptide at an epitope selected from SEQ ID NOs: 13-24.

39. The kit or composition of any of paragraphs 32-38, wherein the inhibitor of CHI3L1 is an inhibitor of a CHI3L1 receptor.

40. The kit or composition of paragraph 39, wherein the CHI3L1 receptor is IL13Rα2, TMEM219, or CRTH2.

41. The kit or composition of any of paragraphs 30-31, wherein the inhibitor of Chi3L1 or the immune checkpoint inhibitor is an inhibitory antibody or nucleic acid molecule.

42. The kit or composition of any of paragraphs 30-41, wherein the inhibitor of Sema7A or β1-integrin is an inhibitory antibody reagent or nucleic acid molecule.

43. The kit or composition of any of paragraph 30-42, comprising administering at least the inhibitor of Sema7A and the inhibitor of β1-integrin.

44. The kit or composition of paragraph 43, wherein a bivalent antibody reagent comprises the inhibitor of Sema7A and the inhibitor of β1-integrin.

45. The kit or composition of any of paragraphs 30-44, wherein the agonist of PlexinC1 is a nucleic acid encoding Growth Arrest Specific 5 (GASS).

46. The kit or composition of any of paragraphs 30-45, wherein the inhibitor of an immune checkpoint protein is an antibody, antibody reagent, antigen-binding fragment thereof, or CAR that specifically binds to at least one immune checkpoint protein.

47. The kit or composition of any of paragraphs 30-45, wherein the inhibitor of an immune checkpoint protein is a natural ligand thereof.

48. The kit or composition of paragraph 47, wherein the natural ligand comprises PD-L1 or B7.

49. The kit or composition of any of paragraphs 30-48 wherein the immune checkpoint protein is selected from the group consisting of:

PD-1; PD-L1; PD-L2; TIM-3; CTLA4; TIGIT; DD1-α; A2AR; B7-H3; B7-H4; BTLA; IDO; TDO; KIR; and LAG3.

50. The kit or composition of paragraph 49, wherein the inhibitor of an immune checkpoint protein is, or comprises the CDRs of an agent, selected from the group consisting of:
MGA271; ipilimumab; pembrolizumab; nivolumab; atezolizumab; galiximab; IMP321; BMS-986016; SMB-663513; PF-05082566; IPH2101; KW-0761; CDX-1127; MEDI-6769; CP-870,893; tremelimumab; pidilizumab; MPDL3280A; MEDI4736; MSB0010718C; AUNP12; avelumab; and durvalumab.

51. The kit or composition of any of paragraphs 30-50 wherein the inhibitor of CHI3L1 and the inhibitor of an immune checkpoint protein are present in the same bivalent antibody reagent.

52. The kit or composition of paragraph 51, wherein the immune checkpoint protein is PD-1 or CTLA4.

53. A therapeutically effective amount of
a) an inhibitor of an immune checkpoint protein; and.
b) at least one agent selected from:
  i) an inhibitor of Sema7A;
  ii) an inhibitor of β1-integrin;
  iii) an agonist of PlexinC1; and
  iv) an inhibitor of CHI3L1.
for use in the treatment of cancer.

54. The agents of paragraph 53, wherein the at least one agent of b) and the inhibitor of an immune checkpoint protein are present in the same composition.

55. The agents of paragraph 53, wherein the at least one agent of b) and the inhibitor of an immune checkpoint protein are present in separate compositions.

56. The agents of any of paragraphs 53-55, wherein the inhibitor of CHI3L1 is an antibody, antibody reagent, antigen-binding fragment thereof, or CAR that specifically binds to CHI3L1.

57. The agents of paragraph 56, wherein an antibody, antibody reagent, antigen-binding fragment thereof, or CAR comprises at least one heavy or light chain complementarity determining region (CDR) selected from the group consisting of:
(a) a light chain CDR1 having the amino acid sequence of SEQ ID NO: 4;
(b) a light chain CDR2 having the amino acid sequence of SEQ ID NO: 5;
(c) a light chain CDR3 having the amino acid sequence of SEQ ID NO: 6;
(d) a heavy chain CDR1 having the amino acid sequence of SEQ ID NO: 1;
(e) a heavy chain CDR2 having the amino acid sequence of SEQ ID NO: 2; and
(f) a heavy chain CDR3 having the amino acid sequence of SEQ ID NO: 3; or
a conservative substitution variant of one or more of (a)-(f).

58. The agents of any of paragraphs 53-57, wherein the antibody, antibody reagent, antigen-binding portion thereof, or CAR of comprises heavy chain CDRs having the amino acid sequences of SEQ ID NOs: 1-3 or a conservative substitution variant of such amino acid sequence.

59. The agents of any of paragraphs 53-58, wherein the antibody, antibody reagent, antigen-binding portion thereof or CAR comprises light chain CDRs having the amino acid sequences of SEQ ID NOs: 4-6 or a conservative substitution variant of such amino acid sequence.

60. The agents of any of paragraphs 53-59, wherein the antibody, antibody reagent, antigen-binding portion thereof or CAR comprises light chain CDRs having the amino acid sequences of SEQ ID NOs: 4-6 and heavy chain CDRs having the amino acid sequences of SEQ ID NOs: 1-3 or a conservative substitution variant of such amino acid sequence.

61. The agents of any of paragraphs 53-60, wherein the inhibitor of CHI3L1 is antibody, antibody reagent, antigen-binding portion thereof or CAR that competes for binding to CHI3L1 with an antibody comprising light chain CDRs having the amino acid sequences of SEQ ID NOs: 4-6 and heavy chain CDRs having the amino acid sequences of SEQ ID NOs: 1-3.

62. The agents of any of paragraphs 53-61, wherein the inhibitor of CHI3L1 binds a CHI3L1 polypeptide at an epitope selected from SEQ ID NOs: 13-24.

63. The agents of any of paragraphs 53-62, wherein the inhibitor of CHI3L1 is an inhibitor of a CHI3L1 receptor.

64. The agents of paragraph 63, wherein the CHI3L1 receptor is IL13Rα2, TMEM219, or CRTH2.

65. The agents of any of paragraphs 53-64, wherein the inhibitor of Chi3L1 or the immune checkpoint protein is an inhibitory antibody or nucleic acid molecule.

66. The agents of any of paragraphs 53-65, wherein the inhibitor of Sema7A or β1-integrin is an inhibitory antibody reagent or nucleic acid molecule.

67. The agents of any of paragraphs 53-66, comprising both the inhibitor of Sema7A and the inhibitor of β1-integrin.

68. The agents of paragraph 67, wherein a bivalent antibody reagent comprises the inhibitor of Sema7A and the inhibitor of β1-integrin.

69. The agents of any of paragraphs 53-68, wherein the agonist of PlexinC1 is a nucleic acid encoding Growth Arrest Specific 5 (GASS).

70. The agents of any of paragraphs 53-69, wherein the cancer is a primary cancer or a metastatic cancer.

71. The agents of any of paragraphs 53-70, wherein the cancer is malignant cancer.

72. The agents of any of paragraphs 53-71, wherein the cancer is selected from the group consisting of:
prostate cancer, colon cancer, rectal cancer, ovarian cancer, kidney cancer, breast cancer, glioblastoma, melanoma, malignant melanoma, and lung cancer.

73. The agents of any of paragraphs 53-72, wherein the inhibitor of an immune checkpoint protein is an antibody, antibody reagent, antigen-binding fragment thereof, or CAR that specifically binds to at least one immune checkpoint protein.

74. The agents of any of paragraphs 53-73, wherein the inhibitor of an immune checkpoint protein is a natural ligand thereof 75. The agents of paragraph 74, wherein the natural ligand comprises PD-L1 or B7.

76. The agents of any of paragraphs 53-75, wherein the immune checkpoint protein is selected from the group consisting of:
PD-1; PD-L1; PD-L2; TIM-3; CTLA4; TIGIT; DD1-α; A2AR; B7-H3; B7-H4; BTLA; IDO; TDO; KIR; and LAG3.

77. The agents of paragraph 76, wherein the inhibitor of an immune checkpoint protein is selected from the group consisting of:
MGA271; ipilimumab; pembrolizumab; nivolumab; atezolizumab; galiximab; IMP321; BMS-986016; SMB-663513; PF-05082566; IPH2101; KW-0761; CDX-1127; MEDI-6769; CP-870,893; tremelimumab;

pidilizumab; MPDL3280A; MEDI4736; MSB0010718C; AUNP12; avelumab; and durvalumab.
78. The agents of any of paragraphs 53-77, wherein the inhibitor of CHI3L1 and the inhibitor of an immune checkpoint protein are present in the same bivalent antibody reagent.
79. The agents of paragraph 78, wherein the immune checkpoint protein is PD-1 or CTLA4.
80. The agents of any of paragraphs 53-79, wherein the agents are administered to a subject determined to have an elevated level of CHI3L1.
81. The agents of 80, wherein the CHI3L1 is circulating CHI3L1.

EXAMPLES

Example 1: Chitinase 3-Like-1 (Chi3l1) Neutralizing Antibodies as Therapeutics in Asthma and Lung Cancer Members of the 18 glycosyl hydrolase (GH) gene family are dysregulated in and play an important role in the pathogenesis of a variety of diseases. This is particularly striking for the chitinase-like protein called chitinase 3-like-1 (Chi3l1; also called Chil1 in mice and YKL-40 in man) in asthma and lung cancer.

It has been demonstrated that the levels of circulating Chi3l1 are increased in human asthma where they correlate with disease severity (1-4). Single nucleotide polymorphisms of Chi3l1 that correlate with increased levels of circulating Chi3l1, asthma prevalence and poor lung function have been identified (2, 3, 5). In accord with the items noted above, it was also demonstrated that null mutations of Chi3l1 markedly decreased Th2 inflammation and eosinophil accumulation in aeroallergen murine asthma models (6).

The levels of circulating YKL-40 are increased in many malignancies including cancers of the prostate, colon, rectum, ovary, kidney, breast, glioblastomas and malignant melanoma (7-19). In these diseases, the levels of YKL-40 frequently correlate directly with disease progression and inversely with disease-free interval and survival (7-19). This is particularly striking in lung cancer where the serum and tissue levels of YKL-40 are impressively increased and correlate with adverse outcomes (20-23). To address the roles of Chi3l1 in these responses, the roles of Chi3l1 in primary and metastatic lung cancer were evaluated. These studies demonstrate that (1) YKL-40 is expressed in an exaggerated manner in human lung cancer where it correlates inversely with survival; (2) in murine models, Chi3l1 is sequentially induced in normal peritumor and tumor tissues during the early and later stages, respectively, of lung cancer development; (3) Chi3l1 induction via a semaphorin 7a-dependent mechanism plays a critical role in the generation of a metastasis permissive pulmonary microenvironment; (4) in metastatic models, Chi3l1 production and metastatic spread can be inhibited via RIG-like helicase (RLH) innate immunity (24, 25). These studies demonstrate that Chi3l1 is induced in selective tissue compartments during lung cancer initiation and progression and define the essential role that it plays in disease progression.

Generation and Characterization of Antibody-Based Anti-Chi3l1 Based Therapeutics.

Because Chi3l1 is induced in patients with asthma and lung cancer and plays a critical role in the pathogenesis of murine models of both diseases studies were undertaken to develop and assess the efficacy of Chi3l1 neutralizing antibodies. Epitopes of Chi3l1 were selected (see Tables 1 and 2 for epitope design and selection) and monoclonal antibodies were generated.

Figure 2A:
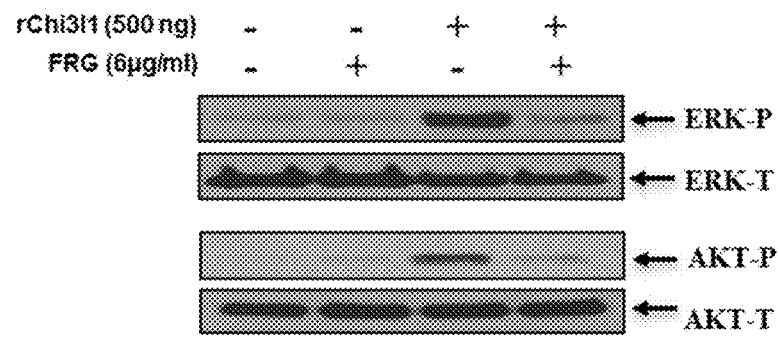
FIGS. 2A-2B demonstrate the neutralizing effects of FRG on Chi3l1-stimulated signaling.
Figure 2B:
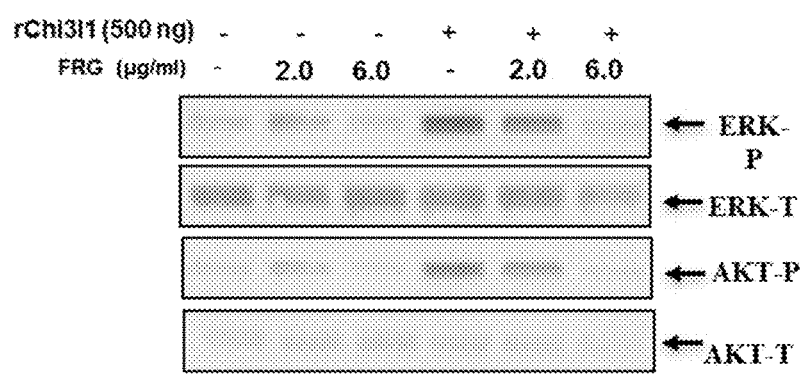

The antibodies were then assessed for their (a) sensitivity, and specificity of detection of Chi3l1 in human and murine systems using denatured and non-denatured Chi3l1; (b) binding affinity; (c) ability to neutralize the effects of rChi3l1 in cell based assays; and (d) ability to neutralize Chi3l1 in vivo. Among the antibodies that were generated one, called FRG, had the most exciting characteristics. It is an IgG2b Kappa antibody that powerfully detects human and murine Chi3l1 under denaturing and non-denaturing conditions with high specificity (FIGS. 1A-1D). It also blocks rChi3l1 induced MAPK and AKT signaling in vitro (FIGS. 2A-2B).

Figure 3:
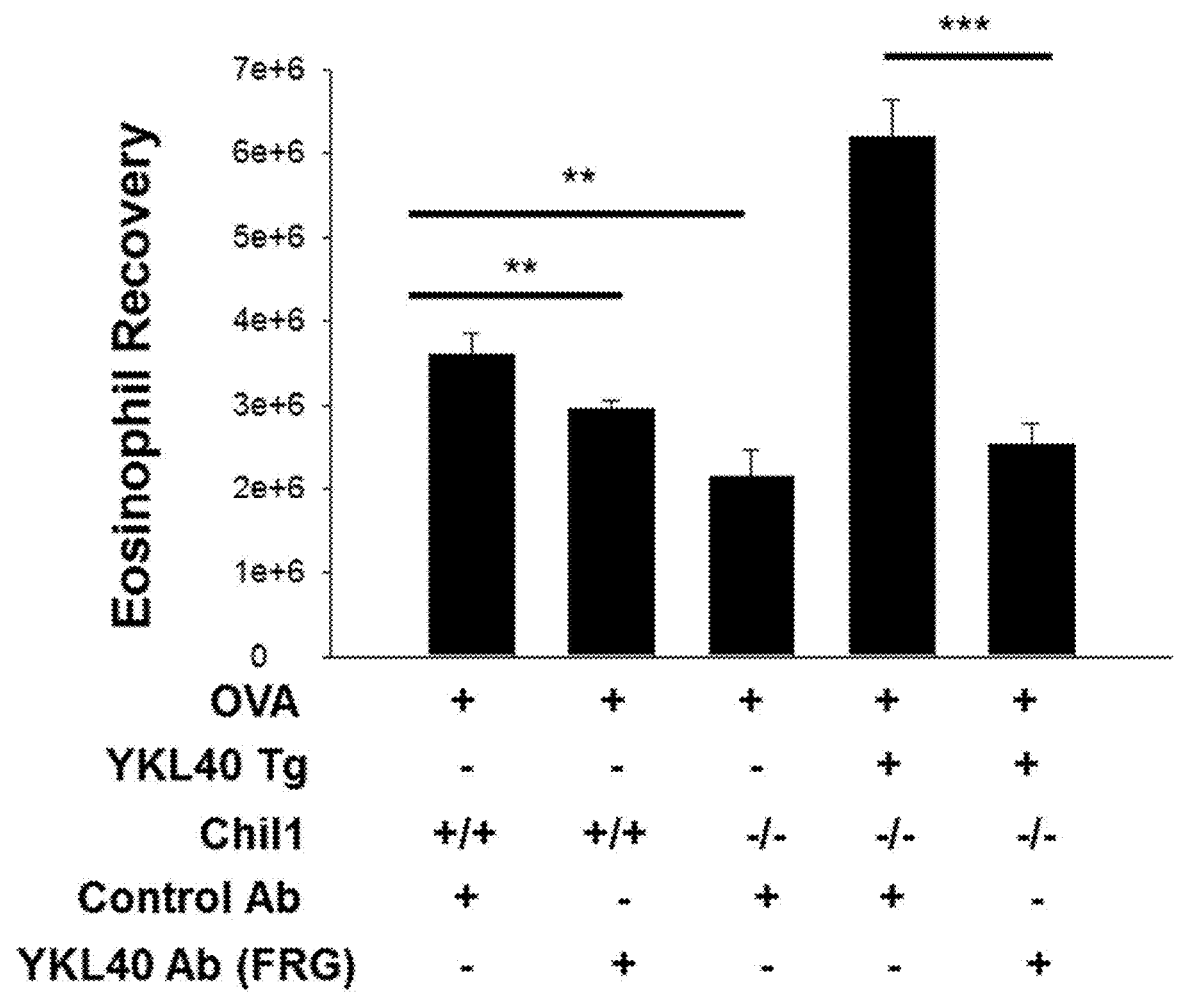
FIG. 3 depicts graphs of the effects of FRG on aeroallergen-stimulated type 2 lung inflammation.

To determine if FRG blocked asthma-like inflammation, the ovalbumin sensitization and challenge murine model was utilized. Wild type mice and mice in which murine Chi3l1 (Chil1) was overexpressed in the airway using the CC10 (also called CCSP) promoter were employed. The effects on airway eosinophilic inflammation were assessed in mice that received an IgG2b control antibody or FRG at a dose of 200 µg/mouse every other day. As can be seen in FIG. 3, the overexpression of Chil1 (Chi3l1) under the influence of the CC10 promoter augmented ovalbumin sensitization and challenge-induced eosinophil recovery as seen in FIG. 3. As can also be seen in FIG. 3, FRG was a potent inhibitor of aeroallergen-induced eosinophilic inflammation and BAL eosinophil accumulation.

To determine if FRG blocked metastatic cancer B16-F10 malignant melanocytes were used as described previously (24, 25). Varying numbers of these cells were administered by tail vein to wild type mice and pulmonary metastasis were quantitated. Melanoma metastasis were assessed in mice that received an IgG2b control antibody or FRG at a dose of 200m/mouse every other day. As can be seen in FIG. 4, FRG was a potent inhibitor of melanoma metastasis. Importantly, these effects were not restricted to melanoma because similar results were seen with breast cancer cells.

Studies were next undertaken to determine if FRG ameliorated the generation of primary lung cancer. In these studies, primary lung cancers were induced in mice with $KRAS^{G12D}$ mutations and p53 mutations (26, 27) and tumor generation was characterized. In this model a discrete mass of tumor cells and a macrophage-rich inflammatory response can be seen 6 weeks after Adeno-Cre recombinase challenge that gradually increases over time (FIG. 5). The generation of primary lung cancers were assessed in mice that received an IgG2b control antibody or FRG at a dose of 200m/mouse every other day. As can be seen in FIGS. 5A-5B, FRG was a potent inhibitor of the generation of primary lung cancers in this model.

Figure 6:
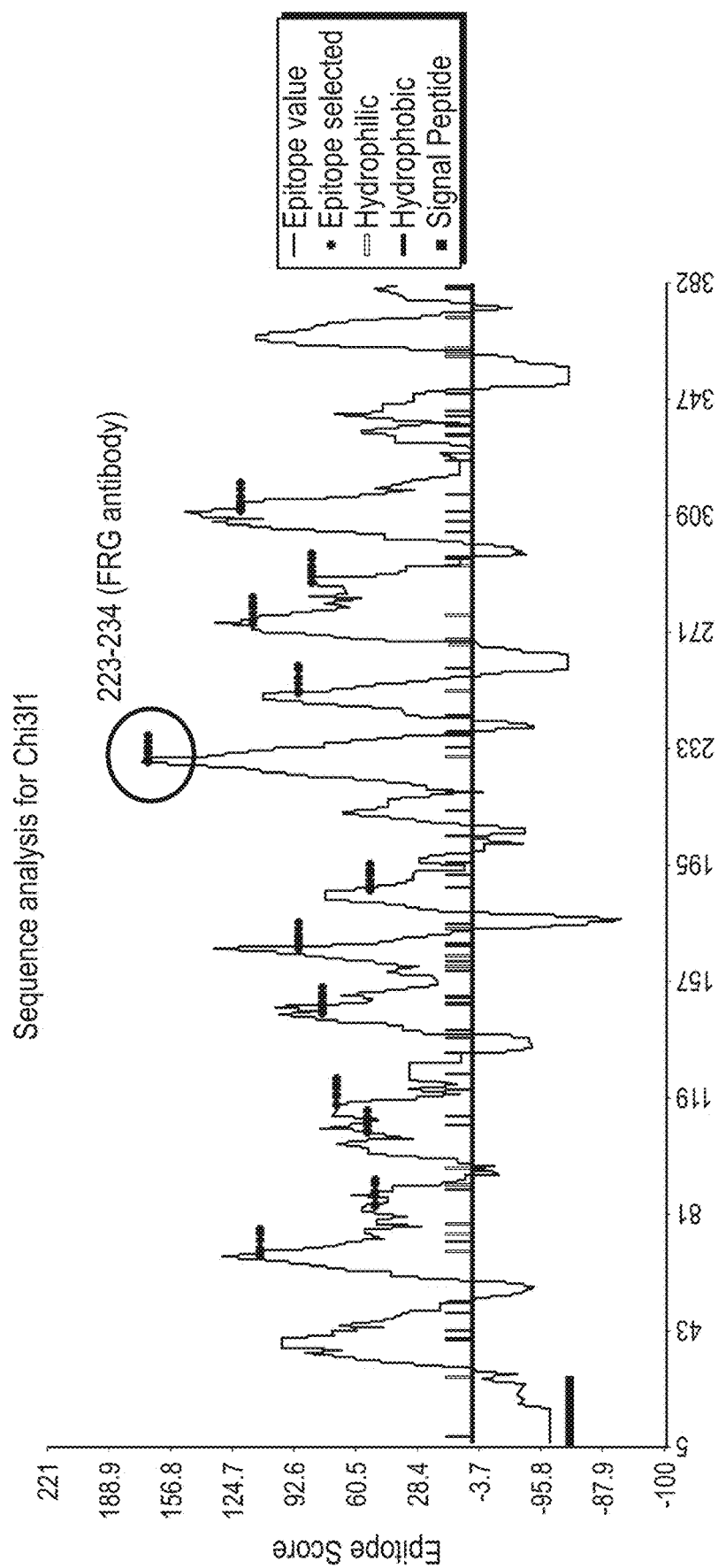
FIG. 6 depicts the location of selected epitopes including FRG in human Chi3l1.

Because of the impressive results of FRG in these in vivo models its variable regions were sequenced. The sequences are noted in Table 3 and the heavy and light chain CDRs are depicted in FIGS. 7 and 8. The location of selected epitopes including that recognized by FRG in human Chi3l1 are depicted in FIG. 6.

Figure 9:
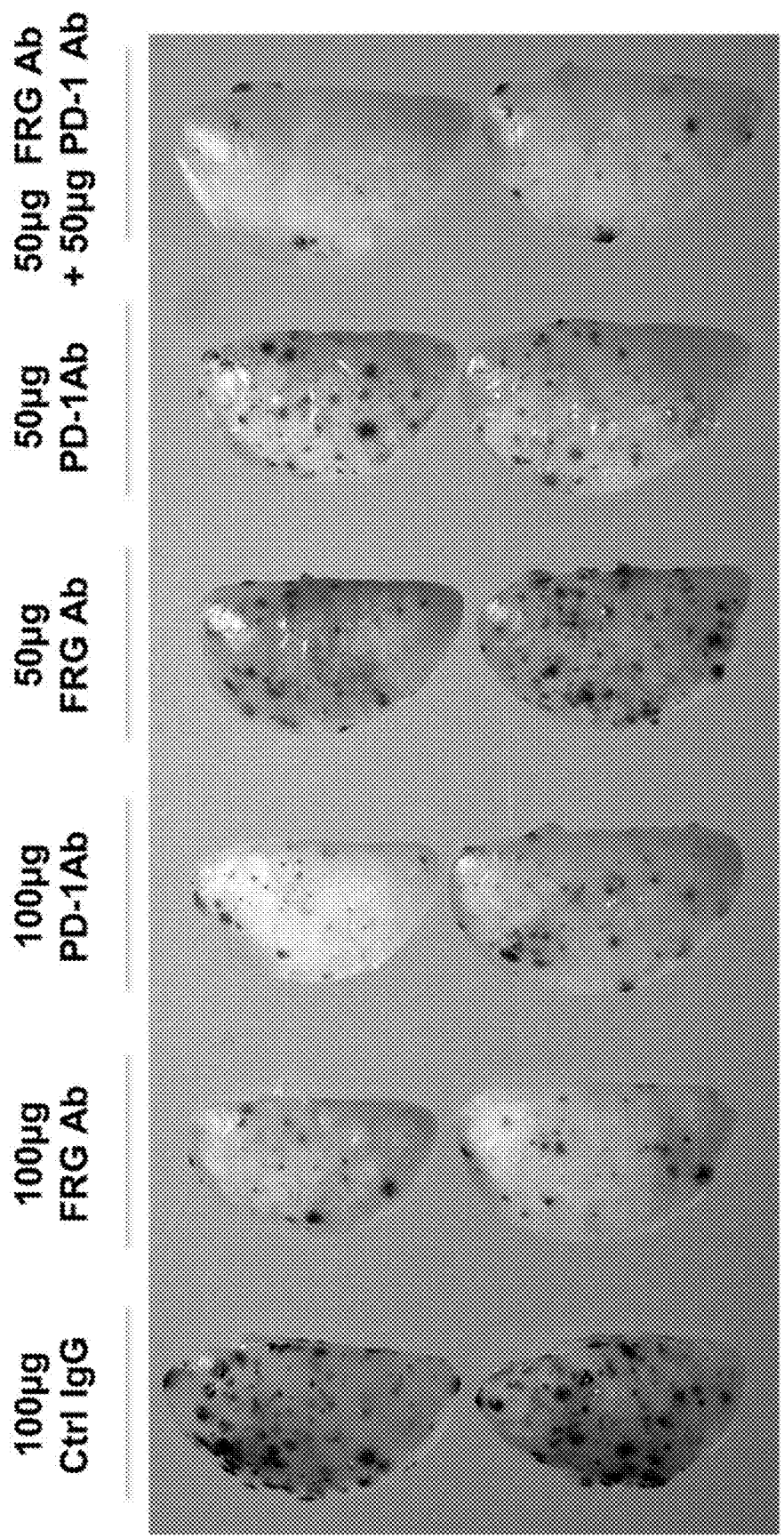
FIG. 9 depicts B16F10 melanoma metastasis in mice treated with the FRG antibody described herein in combination with Anti-PD-1. Images shown were obtained on Day 14. In these experiments malignant melanocytes were administered by tail vein to wild type (WT) mice that were treated every other day with the noted dosages of FRG and or anti-PD-1, alone and in combination, via an intraperitoneal route. Fourteen days later the lungs were removed and the levels of metastasis (black dots on pleural surface) were assessed. The beneficial interactions of FRG and anti-PD-1 in combination can be seen.
Figure 10:
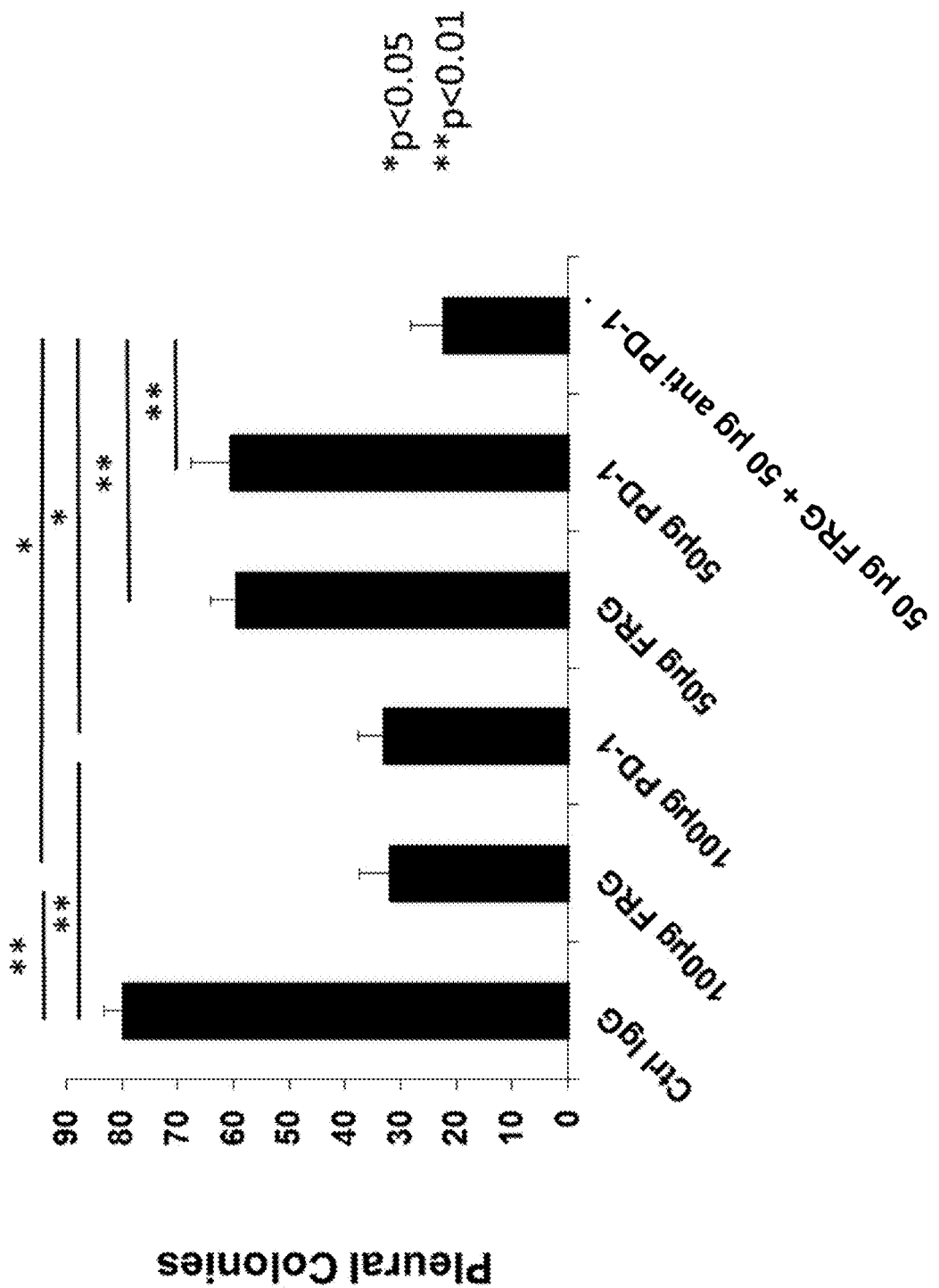
FIG. 10 depicts a graph of the quantitation of the data shown in FIG. 9.

B16F10 melanoma metastasis in mice was treated with the FRG antibody described herein in combination with Anti-PD-1 (FIG. 9). In these experiments malignant melanocytes were administered by tail vein to wild type (WT) mice that were treated every other day with the noted dosages of FRG and or anti-PD-1, alone and in combination, via an intraperitoneal route. Fourteen days later the lungs were removed and the levels of metastasis (black dots on pleural surface) were assessed. The beneficial interactions of FRG and anti-PD-1 in combination can be seen in FIG. 9 and are quantified in FIG. 10.

REFERENCES CITED

1. Chupp G L, Lee C G, Jarjour N, Shim Y M, Holm C T, He S, Dziura J D, Reed J, Coyle A J, Kiener P, Cullen M, Grandsaigne M, Dombret M C, Aubier M, Pretolani M, Elias J A. A chitinase-like protein in the lung and circulation of patients with severe asthma. N Engl J Med. 2007; 357(20):2016-27. doi: 10.1056/NEJMoa073600. PubMed PMID: 18003958.
2. Konradsen J R, James A, Nordlund B, Reinius L E, Soderhall C, Melen E, Wheelock A M, Lodrup Carlsen K C, Lidegran M, Verhoek M, Boot R G, Dahlen B, Dahlen S E, Hedlin G. The chitinase-like protein YKL-40: a possible biomarker of inflammation and airway remodeling in severe pediatric asthma. J Allergy Clin Immunol. 2013; 132(2):328-35 e5. doi: 10.1016/j.jaci.2013.03.003. PubMed PMID: 23628340.
3. Gomez J L, Crisafi G M, Holm C T, Meyers D A, Hawkins G A, Bleecker E R, Jarjour N, Severe Asthma Research Program I, Cohn L, Chupp G L. Genetic variation in chitinase 3-like 1 (CHI3L1) contributes to asthma severity and airway expression of YKL-40. J Allergy Clin Immunol. 2015; 136(1):51-8 e10. doi: 10.1016/j.jaci.2014.11.027. PubMed PMID: 25592985; PMCID: PMC4494869.
4. James A J, Reinius L E, Verhoek M, Gomes A, Kupczyk M, Hammar U, Ono J, Ohta S, Izuhara K, Bel E, Kere J, Soderhall C, Dahlen B, Boot R G, Dahlen S E, Consortium B. Increased YKL-40 and Chitotriosidase in Asthma and Chronic Obstructive Pulmonary Disease. Am J Respir Crit Care Med. 2016; 193(2):131-42. doi: 10.1164/reem.201504-07600C. PubMed PMID: 26372680.
5. Ober C, Tan Z, Sun Y, Possick J D, Pan L, Nicolae R, Radford S, Parry R R, Heinzmann A, Deichmann K A, Lester L A, Gem J E, Lemanske R F, Jr., Nicolae D L, Elias J A, Chupp G L. Effect of variation in CHI3L1 on serum YKL-40 level, risk of asthma, and lung function. N Engl J Med. 2008; 358(16):1682-91. doi: 10.1056/NEJMoa0708801. PubMed PMID: 18403759; PMCID: PMC2629486.
6. Lee C G, Hartl D, Lee G R, Koller B, Matsuura H, Da Silva C A, Sohn M H, Cohn L, Homer R I, Kozhich A A, Humbles A, Kearley J, Coyle A, Chupp G, Reed J, Flavell R A, Elias J A. Role of breast regression protein 39 (BRP-39)/chitinase 3-like-1 in Th2 and IL-13-induced tissue responses and apoptosis. J Exp Med. 2009; 206(5): 1149-66. doi: 10.1084/jem.20081271. PubMed PMID: 19414556; PMCID: PMC2715037.
7. Choi I K, Kim Y H, Kim J S, Seo J H. High serum YKL-40 is a poor prognostic marker in patients with advanced non-small cell lung cancer. Act Oncol. 2010; 49(6):861-4. PubMed PMID: 20553098.
8. Coffman F D. Chitinase 3-Like-1 (CHI3L1): a putative disease marker at the interface of proteomics and glycomics. Crit Rev Clin Lab Sci. 2008; 45(6):531-62. Epub 2008/11/13. doi: 905315713 [pii] 10.1080/10408360802334743. PubMed PMID: 19003601.
9. Iwamoto F M, Hottinger A F, Karimi S, Riedel E, Dantis J, Jandi M, Panageas K S, Lassman A B, Abrey L E, Fleisher M, Deangelis L M, Holland E C, Hormigo A. Serum YKL-40 is a marker of prognosis and disease status in high-grade gliomas. Neuro Oncol. 2011; 13(11): 1244-51. doi: 10.1093/neuonc/nor117. PubMed PMID: 21831900; PMCID: PMC3199155.
10. Johansen J S, Cintin C, Jorgensen M, Kamby C, Price P A. Serum YKL-40: a new potential marker of prognosis and location of metastases of patients with recurrent breast cancer. Eur J Cancer. 1995; 31A(9):1437-42. PubMed PMID: 7577068.
11. Johansen J S, Jensen B V, Roslind A, Nielsen D, Price P A. Serum YKL-40, a new prognostic biomarker in cancer patients? Cancer Epidemiol Biomarkers Prev. 2006; 15(2):194-202. Epub 2006/02/24. doi: 15/2/194 [pii] 10.1158/1055-9965. EPI-05-0011. PubMed PMID: 16492905.
12. Johansen J S, Schultz N A, Jensen B V. Plasma YKL-40: A potential new cancer biomarker? Future Oncol. 2009; 5(7):1065-82. PubMed PMID: 19792974.
13. Peng C, Peng J, Jiang L, You Q, Zheng J, Ning X. YKL-40 protein levels and clinical outcome of human endometrial cancer. J Int Med Res. 2010; 38(4):1448-57. PubMed PMID: 20926018.
14. Schmidt H, Johansen J S, Gehl J, Geertsen P F, Fode K, von der Maase H. Elevated serum level of YKL-40 is an independent prognostic factor for poor survival in patients with metastatic melanoma. Cancer. 2006; 106(5):1130-9. Epub 2006/02/04. doi: 10.1002/cncr.21678. PubMed PMID: 16456816.
15. Schmidt H, Johansen J S, Sjoegren P, Christensen I J, Sorensen B S, Fode K, Larsen J, von der Maase H. Scrum YKL-40 predicts relapse-free and overall survival in patients with American Joint Committee on Cancer stage I and II melanoma. J Clin Oncol. 2006; 24(5):798-804. Epub 2006/01/05. doi: JCO.2005.03.7960 [pii] 10.1200/JCO.2005.03.7960. PubMed PMID: 16391295.
16. Shao R, Cao Q J, Arenas R B, Bigelow C, Bentley B, Yan W. Breast cancer expression of YKL-40 correlates with tumour grade, poor differentiation, and other cancer markers. Br J Cancer. 2011; 105(8):1203-9. doi: 10.1038/bjc.2011.347. PubMed PMID: 21934681; PMCID: PMC3208489.
17. Shao R, Hamel K, Petersen L, Cao Q J, Arenas R B, Bigelow C, Bentley B, Yan W. YKL-40, a secreted glycoprotein, promotes tumor angiogenesis. Oncogene. 2009; 28(50):4456-68. Epub 2009/09/22. doi: onc2009292 [pii] 10.1038/onc.2009.292. PubMed PMID: 19767768; PMCID: 2795793.
18. Hottinger A F, Iwamoto F M, Karimi S, Riedel E, Dantis J, Park J, Panageas K S, Lassman A B, Abrey L E, Fleisher M, Holland E C, DeAngelis L M, Hormigo A. YKL-40 and MMP-9 as serum markers for patients with primary central nervous system lymphoma. Ann Neurol. 2011; 70(1):163-9. doi: 10.1002/ana.22360. PubMed PMID: 21391238.
19. Chen C C, Pekow J, Llado V, Kanneganti M, Lau C W, Mizoguchi A, Mino-Kenudson M, Bissonnette M, Mizoguchi E. Chitinase 3-like-1 expression in colonic epithelial cells as a potentially novel marker for colitis-associated neoplasia. Am J Pathol. 2011; 179(3):1494-503. doi: 10.1016/j.ajpath.2011.05.038. PubMed PMID: 21763261; PMCID: PMC3157229.
20. Thom I, Andritzky B, Schuch G, Burkholder I, Edler L, Johansen J S, Bokemeyer C, Schumacher U, Laack E. Elevated pretreatment serum concentration of YKL-40-An independent prognostic biomarker for poor survival in patients with metastatic nonsmall cell lung cancer. Cancer. 2010; 116(17):4114-21. Epub 2010/06/22. doi: 10.1002/cncr.25196. PubMed PMID: 20564116.
21. Choi I K, Kim Y H, Kim J S, Seo J H. High serum YKL-40 is a poor prognostic marker in patients with advanced non-small cell lung cancer. Acta Oncol. 2010; 49(6):861-4. Epub 2010/06/18. doi: 10.3109/02841861003631503. PubMed PMID: 20553098.
22. Junker N, Johansen J S, Andersen C B, Kristjansen P E. Expression of YKL-40 by peritumoral macrophages in human small cell lung cancer. Lung Cancer. 2005; 48(2): 223-31. Epub 2005/04/15. doi: 10.1016/j.lungcan.2004.11.011. PubMed PMID: 15829322.

23. Johansen J S, Drivsholm L, Price P A, Christensen U. High serum YKL-40 level in patients with small cell lung cancer is related to early death. Lung Cancer. 2004; 46(3):333-40. Epub 2004/11/16. doi: 10.1016/j.lungcan.2004.05.010. PubMed PMID: 15541818.
24. Ma B, Herzog E L, Moore M, Lee C M, Na S H, Lee C G, Elias J A. RIG-like Helicase Regulation of Chitinase 3-like 1 Axis and Pulmonary Metastasis. Sci Rep. 2016; 6:26299. doi: 10.1038/srep26299. PubMed PMID: 27198666; PMCID: PMC4873814.
25. Ma B, Herzog E L, Lee C G, Peng X, Lee C M, Chen X, Rockwell S, Koo J S, Kluger H, Herbst R S, Sznol M, Elias J A. Role of chitinase 3-like-1 and semaphorin 7a in pulmonary melanoma metastasis. Cancer Res. 2015; 75(3):487-96. doi: 10.1158/0008-5472.CAN-13-3339. PubMed PMID: 25511377; PMCID: PMC4321965.
26. Johnson L, Mercer K, Greenbaum D, Bronson R T, Crowley D, Tuveson D A, Jacks T. Somatic activation of the K-ras oncogene causes early onset lung cancer in mice. Nature. 2001; 410(6832):1111-6. Epub 2001/04/27. doi: 10.1038/35074129. PubMed PMID: 11323676.
27. Jackson E L, Olive K P, Tuveson D A, Bronson R, Crowley D, Brown M, Jacks T. The differential effects of mutant p53 alleles on advanced murine lung cancer. Cancer Res. 2005; 65(22):10280-8. Epub 2005/11/17. doi: 10.1158/0008-5472.CAN-05-2193. PubMed PMID: 16288016.

TABLE 1

Parameters considered in epitope selection algorithms.

| | |
|---|---|
| Secondary Structure | Amino Acid property |
| Loop/helix/sheet | Antigenic enhancement amino acid |
| Special region | Flexibility |
| N-terminal, C-terminal | Evolution |
| Signal peptide | Positive selection |
| Trans-membran | Discrimination |
| Disordered region | Customer requests |
| Solvent accessibility | Protein specificity |
| Blast | Region specificity |
| Query species and Mouse | Others |

TABLE 2

List of selected epitopes including FRG (ID Number 0)

| ID number | Start | End | Peptide | SEQ ID NO |
|---|---|---|---|---|
| 0 | 223 | 234 | FRGQEDASPDRF | 13 |
| 1 | 304 | 315 | RGATVHRILGQQ | 14 |
| 2 | 268 | 279 | ASSETGVGAPIS | 15 |
| 3 | 162 | 173 | IKEAQPGKKQLL | 16 |
| 4 | 62 | 73 | SNDHIDTWEWND | 17 |
| 5 | 141 | 152 | YPGRRDKQHFTT | 18 |
| 6 | 245 | 256 | LRLGAPASKLVM | 19 |
| 7 | 281 | 292 | PGIPGRFTKEAG | 20 |
| 8 | 102 | 113 | GSQRFSKIASNT | 21 |
| 9 | 181 | 192 | GKVTIDSSYDIA | 22 |
| 10 | 78 | 89 | GMLNTLKNRNPN | 23 |
| 11 | 111 | 122 | SNTQSRRTFIKS | 24 |

Location of selected epitopes including FRG in human Chi3I1 (italics)

(SEQ ID NO: 25)
MGVKASQTGFVVLVLLQCCSAYKLVCYYTSWSQYREGDGSCFPDALDRFL

CTHIIYSFANISNDHIDTWEWNDVTLYGMLNTLKNRNPNLKTLLSVGGWN

FGSQRFSKIASNTQSRRTFIKSVPPFLRTFIGFDGLDLAWLYPGRRDKQH

FTTLIKEMKAEFIKEAQPGKKQLLLSAALSAGKVTIDSSYDIAKISQHLD

FISIMTYDFHGAWRGTTGHHSPL*PQEDASPDRF*SNTDYAVGYMLRLGAP

ASKLVMGIPTFGRSFTLASSETGVGAPISGPGIPGRFTKEAGTLAYYEIC

DFLRGATVHRILGQQVPYATKGNQWVGYDDQESVKSKVQYLKDRQLAGAM

VWALDLDDFQGSFCGQDLRFPLTNAIKDALAAT

TABLE 3

Sequences of variable complementarity determining regions (CDRs) of FRG antibody

| | | | SEQ ID NO: |
|---|---|---|---|
| Heavy chain (IgG2b) | CDR1 | GYTFTNYG | 1 |
| | (DNA) | (GGGTATACCTTCACAAACTATGGA) | 7 |
| | CDR2 | I N T Y T G E P | 2 |
| | (DNA) | (ATAAATACCTACACTGGAGAGCCA) | 8 |
| | CDR3 | ARLGYGKFYVMDY | 3 |
| | (DNA) | (GCAAGATTGGGATATGGTAAATTCTAT GTTATGGACTAC) | 9 |
| Light chain (IgG K) | CDR1 | QSLVHSNGNTY | 4 |
| | (DNA) | (CAGAGCCTTGTACACAGTAATGGAAAC ACCTAT) | 10 |
| | CDR2 | K V S | 5 |
| | (DNA) | (AAAGTTTCC) | 11 |
| | CDR3 | S Q S T H V T W T | 6 |
| | (DNA) | (TCTCAAAGTACACATGTTACGTGGACG) | 12 |

Example 2

When the FRG antibody was administered in combination with a checkpoint inhibitor (e.g., anti-PD-1), synergism was observed (FIGS. 9, 10), with the combination displaying improved efficacy in reducing B16F10 metastasis. Accordingly, it is contemplated herein that the combination of CHI3L1 inhibition and inhibition of a checkpoint protein provides synergistic efficacy in the treatment of cancer.

It is specifically contemplated herein that CHI3L1 functions as a regulator of immune checkpoint proteins and costimulatory molecules on T cells. Accordingly, targeting both CHI3L1 and a checkpoint protein provides a synergistic effect.

What is claimed herein is:

1. A method of treating cancer in a subject in need thereof, the method comprising administering bispecific antibody that detects and neutralizes chitinase 3-like-1 (CHI3L1) and programed death receptor 1 (PD 1) comprising:
  (a) an antigen-binding portion of an anti-human PD 1 antibody; and
  (b) an antigen-binding portion of an anti-human CHI3L1 antibody comprising light chain complementarity determining regions (CDRs) having the amino acid sequences of SEQ ID NOs: 4-6 and heavy chain CDRs having the amino acid sequences of SEQ ID NOs: 1-3, wherein the cancer expresses PD-L1 and CHI3L1.

2. The method of claim 1, wherein the bispecific antibody comprises an anti-human CHI3L1 single chain variable fragment (ScFv CHI3L1) attached to a backbone of an anti-human PD-1 antibody.

3. The method of claim 1, wherein the bispecific antibody comprises an anti-human PD-1 single chain variable fragment (ScFv PD1) attached to a backbone of an anti-human CHI3L1 antibody.

4. The method of claim 3, wherein the ScFv PD1 is attached to the heavy chain of the CHI3L1 antibody backbone.

5. The method of claim 3, wherein the ScFv PD1 is attached to the light chain of the CHI3L1 antibody backbone.

6. The method of claim 3, wherein the anti-human CHI3L1 antibody comprises a heavy chain sequence having the amino acid sequence of SEQ ID NO: 36 or a light chain sequence having the amino acid sequence of SEQ ID NO: 38.

7. The method of claim 3, wherein the anti-human CHI3L1 antibody comprises a heavy chain sequence having the amino acid sequence of SEQ ID NO: 36 and a light chain sequence having the amino acid sequence of SEQ ID NO: 38.

8. The method of claim 3, wherein the anti-human CHI3L1 antibody comprises a conservative substitution relative to the heavy chain sequence having the amino acid sequence of SEQ ID NO: 36 or the light chain sequence having the amino acid sequence of SEQ ID NO: 38, wherein the conservative substitution is in a sequence not comprised by a CDR.

9. The method of claim 1, wherein the antigen-binding portion of the anti-human CHI3L1 antibody binds a CHI3L1 polypeptide at an epitope having the amino acid sequences of SEQ ID NO: 13.

10. The method of claim 1, wherein the cancer is a primary cancer or a metastatic cancer.

11. The method of claim 1, wherein the cancer is malignant cancer.

12. The method of claim 1, wherein the cancer is selected from the group consisting of: prostate cancer, colon cancer, rectal cancer, ovarian cancer, kidney cancer, breast cancer, glioblastoma, melanoma, malignant melanoma, and lung cancer.

13. The method of claim 1, wherein the subject is a subject determined to have an elevated level of CHI3L1 compared to a reference level.

14. The method of claim 13, wherein the CHI3L1 is circulating CHI3L1.

15. The method of claim 1, wherein the subject is a subject determined to have a level of CHI3L1 that is increased compared to a prior assessment of the level in that subject.

16. The method of claim 15, wherein the CHI3L1 is circulating CHI3L1.

* * * * *